US005885577A

United States Patent [19]
Alvarez

[11] Patent Number: 5,885,577
[45] Date of Patent: Mar. 23, 1999

[54] ANTIGEN BINDING PEPTIDES (ABTIDES) FROM PEPTIDE LIBRARIES

[75] Inventor: Vernon L. Alvarez, Morrisville, Pa.

[73] Assignee: Cytogen Corporation, Princeton, N.J.

[21] Appl. No.: 488,161

[22] Filed: Jun. 7, 1995

Related U.S. Application Data

[63] Continuation-in-part of Ser. No. 310,192, Sep. 21, 1994.
[51] Int. Cl.$^6$ ..................... A61K 39/395; C07K 16/30; C07K 7/00
[52] U.S. Cl. .................................. 424/155.1; 424/143.1; 424/141.1; 514/12; 530/324; 530/388.8
[58] Field of Search .................................. 436/518, 517; 530/324, 388.8; 514/12; 424/143.1, 141.1, 155.1

[56] References Cited

U.S. PATENT DOCUMENTS

| | | |
|---|---|---|
| 5,096,815 | 3/1992 | Ladner et al. . |
| 5,162,504 | 11/1992 | Horoszewicz . |
| 5,198,346 | 3/1993 | Ladner et al. . |
| 5,223,409 | 6/1993 | Ladner et al. . |
| 5,270,170 | 12/1993 | Schatz et al. . |
| 5,458,538 | 10/1995 | Kay et al. . |
| 5,625,033 | 4/1997 | Kay et al. ............................... 530/324 |

FOREIGN PATENT DOCUMENTS

| | | |
|---|---|---|
| 590 689 A2 | 4/1994 | European Pat. Off. . |
| 2 183 661 | 6/1987 | United Kingdom . |
| WO 86/05806 | 10/1986 | WIPO . |
| WO 91/05058 | 4/1991 | WIPO . |
| WO 91/12328 | 8/1991 | WIPO . |
| WO 91/18980 | 12/1991 | WIPO . |
| WO 91/19818 | 12/1991 | WIPO . |
| WO 92/06191 | 4/1992 | WIPO . |
| WO 92/15605 | 9/1992 | WIPO . |
| WO 92/15677 | 9/1992 | WIPO . |
| WO 92/15679 | 9/1992 | WIPO . |
| WO 94/11496 | 5/1994 | WIPO . |
| WO 94/18318 | 8/1994 | WIPO . |
| WO 96/09411 | 3/1996 | WIPO . |

OTHER PUBLICATIONS

Medynski et al., 1994, "Synthetic peptide combinatorial libraries", Bio/Technology 12:709–710.
Gallop et al., 1994, "Applications of combinatorial technologies to drug discoveries. 1. Background and peptide combinatorial libraries", J Med Chem 37(9):1233–1251.
Yu et al., 1994, "Structural basis for the binding of proline–rich peptides to SH3 domains", Cell 76:933–945.
Rebar and Pabo, 1994, "Zinc finger phage: Affinity selection of fingers with new DNA–binding specificities", Science 263:671–673.
Yayon et al., 1993, "Isolation of peptides that inhibit binding of basic fibroblast growth factor to its receptor from a random phage–epitope library", Proc Natl Acad Sci 90:10643–10647.
Balass et al., 1993, "Identification of a hexapeptide that mimics a conformation–dependant binding site of acetylcholine receptor by use of a phage–epitope library", Proc Natl Acad Sci 90:10638–10642.
Bock et al., 1992, "Selection of single–stranded DNA molecules that bind and inhibit human thrombin", Nature 355:564–566.
Tuerk et al., 1992, "RNA pseudoknots that inhibit human immunodeficiency virus type 1 reverse transcriptase", Proc Natl Acad Sci 89:6988–6992.
Christian et al., 1992, "Simplified methods for construction, assessment and rapid screening of peptide libraries in bacteriophage", J Mol Biol 227:711–718.
Lenstra et al., 1992, "Isolation of sequences from a random–sequence expression library that mimic viral epitopes", J Immunol Methods 152:149–157.
Cull et al., 1992, "Screening for receptor ligands using large libraries of peptides linked to the C terminus of the lac repressor", Proc Natl Acad Sci 89:1865–1869.
Oldenberg et al., 1992, "Peptide libraries for a sugar–binding protein isolated from a random peptide library", Proc Natl Acad Sci 89:5393–5397.
Caesareni, 1992, "Peptide display on filamentous phage capsids: A new powerful tool to study protein–ligand interaction", FEBS 307(1):66–70.
O'Neil et al., 1992, "Identification of novel peptide antagonists for GPIIb/IIIa from a confromationally constrained phage peptide library", Proteins: Struct Func Genet 14:509–515.
Ellington and Szostak, 1992, "Selection in vitro of single–stranded DNA molecules that fold into specific ligand–binding structures", Nature 355:850–852.
Fowlkes et al., 1992, "Multipurpose vectors for peptide expression on the M13 viral surface", BioTechniques 13(3):422–427.

(List continued on next page.)

Primary Examiner—Ponnathapura Achutamurthy
Assistant Examiner—T. D. Wessendorf
Attorney, Agent, or Firm—Pennie & Edmonds LLP

[57] ABSTRACT

Abtides are provided. Abtides are peptides identified by a two-step process of screening random peptide libraries. In the first step, the target ligand is an antibody or receptor (or derivative thereof). The peptides identified in the first screening step are used as target ligands in the second screening step. The peptides identified in the second screening step are abtides. Abtides possess binding specificities that are similar to the binding specificities of the antibodies or receptors that are used in the first screening step. Abtides may be used in place of antibodies in many assays or therapeutic applications.

Abtides binding to polymorphic epithelial mucin (PEM) are provided.

Also provided are methods of obtaining abtides as well as diagnostic and therapeutic compounds containing abtides.

2 Claims, 9 Drawing Sheets

OTHER PUBLICATIONS

Lowman et al., 1991, "Selecting high–affinity binding proteins by monovalent phage display", Biochemistry 30:10832–10838.

Lam et al., 1991, "A new type of synthetic peptide library for identifying ligand–binding activity", Nature 354:82–84.

Houghten et al., 1991, "Generation and use of synthetic peptide combinatorial libraries for basic research and drug discoveries", Nature 354:84–86.

Fodor et al., 1991, "Light–directed, spatially addressable parallel chemical synthesis", Science 251:767–773.

Marks et al., 1991, "By–passing immunization: Human antibodies from V–gene libraries displayed on phage", J Mol Biol 222:581–597.

Greenwood et al., 1991, "Multiple display of foreign peptides on a filamentous bacteriophage", J Mol Biol 220:821–827.

Hoogenboom et al., 1991, "Multi–subunit proteins on the surface of filamentous phage: Methodologies for displaying antibody (Fab) heavy and light chains", Nucleic Acid Res 19(15):4133–4137.

Kang et al., 1991, "Linkage of recognition and replication functions by assembling combinatorial antibody Fab libraries along phage surfaces", Proc Natl Acad Sci 88:4363–4366.

Scott and Smith, 1990, "Search for peptides ligands with an epitope library", Science 249:386–390.

Bass et al., 1990, "Hormone phage: An enrichment method for variant proteins with altered binding properties", Proteins: Struct Func Genet 8:309–314.

Cwirla et al., 1990, "Peptides on phage: A vast library of peptides for identifying ligands", Proc Natl Acad Sci 87:6378–6382.

McCafferty et al., 1990, "Phage antibodies: Filamentous phage displaying antibody variable domains", Nature 348:552–554.

Devlin et al., 1990, "Random peptide libraries: A source of specific protein binding molecules", Science 249:404–406.

Parmley and Smith, 1989, "Filamentous fusion phage cloning vectors for the study of eptiopes and design of vaccines", Adv Exp Med Biol 251:215–218.

Parmley and Smith, 1988, "Antibody–selectable filamentous fd phage vectors: Affinity purification of target genes", Gene 73:305–318.

Staudt et al., 1988, "Cloning of a lymphoid–specific cDNA encoding a protein binding the regulatory octamer DNA motif", Science 241:577–580.

de la Cruz et al., 1988, "Immunogenicity and epitope mapping of foreign sequences via genetically engineered filamentous phage", J Biol Chem 263(9):4318–4322.

Horoszewicz et al., 1987, "Monoclonal antibodies to a new antigenic marker in epithelial prostatic cells and serum of prostatic cancer patients", Anticancer Res 7:927–936.

Smith, 1985, "Filamentous fusion phage: Novel expression vectors that display cloned antigens on the virion surface", Science 228:1315–1317.

Nishimori et al., 1994, "N–acetylgalactosamine glycosylation of MUC1 tandem repeat peptides by pancreatic tumor cell extracts," Cancer Res. 54:3738–3744.

Bruchell et al., 1989, "A short sequence, within the amino acid tandem repeat of a cancer–associated mucin, contains immunodominant epitopes", Int. J. Cancer 44:691–696.

CLONE 14    GIINANDPLPFWFMS--PYTPGPAPIDINASRALVS-NESG
                    WQGTHFPYT            LVSKNDSG
                     CDR3L                CDR2L
                  (5/9 = 55.5 %)       (7/8 = 87.5 %)

CLONE 17    DL-SRNLDFGRFLLYNA--YVPGFTPTFISLTAEHLSSPKG
              LVSKN-DSG      WQGTHF-P-YT
                CDR2L           CDR3L
             (6/8 = 75 %)    (6/9 = 66.6 %)

CLONE 15    CGRAYCL-SGNYNIFGALFPGVS--TPYADVGHDDAQSWRR
              LVSKN-DS-G   WQG-THFPYT
                CDR2L        CDR3L
            (4/8 = 50 %) (6/9 = 66.6 %)

CLONE 13    RCSPIW-GIS-YPFGLLSSNPGVCHSSDAET-NIRNDILTT
                 WQG-THFPYT           GSDN-K-SVL
                   CDR3L              CDR2L(REV)
                (6/9 = 66.6 %)        (4/8 = 50 %)

CLONE 16    GHSNYCFVSTLGMPIVGFP-SINARGLIHYGGSDPR--LAA
                    WQGTHFPYT           GSDNKSVL
                     CDR3L             CDR2L(REV)
                  (3/9 = 33.3 %)      (5/8 = 62.5 %)

FIG.3

```
                                    Sac II
c.tgt.gcc.tcg.agB.(NNB)₁₂.Ncc.gcg.g
─────────────────────────────────────
```

```
                              gg.cgc.cNV.(NNV)₁₂.aga.tct.cgt.gtc
N=A,G,T,C                     │
B=G,T,C                       │    FILL IN WITH DNA POLYMERASE
V=G,A,C                       ▼
```

```
    Xho I                        Ala
c.tgt.gcc.tcg.agB.(NNB)₁₂.Ncc.gcg.g
─────────────────────────────────────////////////////////////////
//////////////////////////////──────────────────────────────────
                              gg.cgc.cNV.(NNV)₁₂.aga.tct.cgt.gtc
                                                      Xba I
                              │    CLEAVE WITH Xho I + Xba I
                              ▼
```

```
    tcg.agB.(NNB)₁₂.Ncc.gcg.g
    ─────────────────────────────//////////////////
    //////////////////───────────────────────────
                    gg.cgc.cNV.(NNV)₁₂.tga.tc │    LIGATE WITH Xho I + Xba I-
                    │    CLEAVED M13 m663 VECTOR
                    │
                    ▼    ELECTROPORATE INTO XL1-BLUE
```

LIBRARY OF pIII-RANDOM SEQUENCE FUSION PROTEINS

. . . S H S | S (S/R) X₁₂ π A ∂ X₁₂ S R | P S R T . . .

⬆
SIGNAL PEPTIDASE CLEAVAGE SITE

G TGT GTC TCG AGN (NNB)$_{20}$NAC GCC AN

NTG CGG TNV (NNV)$_{15}$AGA TCT GTG TTG

N=A,C,G,T
B=C,G,T
V=A,C,G

FILL IN WITH SEQUENASE

Xho I
G TGT GTC TCG AGN (NNB)$_{20}$NAC GCC AN

NTG CGG TNV (NNV)$_{15}$AGA TCT GTG TTG
Xba I

RESTRICT WITH Xho I AND Xba I

TCG AGN (NNB)$_{20}$ NAC GCC AN

NTG CGG TNV (NNV)$_{15}$AGA TC

LIGATE WITH Xho I + Xba I-CLEAVED M13mp18Xa

ELECTROTRANSFORM
E. coli JS5

D38 GENETIC DIVERSITY LIBRARY DISPLAYED AS RANDOM N-TERMINAL pIII FUSIONS

. . H S↑S (S/R) X$_{20}$ (Y/H/N/D) A (I/M/T/N/K/S/R) X$_{15}$ S R

SIGNAL PEPTIDASE CLEAVAGE SITE

FIG.11

G TGT GTC TCG AGN (NNB)$_{20}$ GGT TGT GGT
_____

CCA ACA CCA (NNV)$_{20}$ AGA TCT GTG TTG

N=A,C,G,T
B=C,G,T                 ↓ FILL IN WITH SEQUENASE
V=A,C,G

<u>Xho I</u>
G TGT GTC TCG AGN (NNB)$_{20}$ GGT TGT GGT
_____

CCA ACA CCA (NNV)$_{20}$ <u>AGA TCT</u> GTG TTG
                                                                    Xba I

↓ RESTRICT WITH Xho I AND Xba I

TCG AGN (NNB)$_{20}$ GGT TGT GGT
_____

CCA ACA CCA (NNV)$_{20}$ AGA TC

↓ LIGATE WITH Xho I + Xba I-
                  CLEAVED M13mp18Xa

↓ ELECTROTRANSFORM
                  <u>E. coli JS5</u>

DC43 GENETIC DIVERSITY LIBRARY DISPLAYED AS RANDOM
N-TERMINAL pIII FUSIONS

. . H S↑S (S/R) X$_{20}$ G C G X$_{20}$ S R

↑SIGNAL PEPTIDASE CLEAVAGE SITE

5' ggs-gcs-ccs-gts-tgs-ags-ggs-aas-ccs-cgs-tgs-ags-ggs-ccs-ggs-ggs-tts-aas-tgs-ccs-GGC-TGC-GGG 3'

MP-1 oligo 1

3' CCG-ACG-CCC-tts-ccs-ggs-tas-acs-tis-tgs-aas-tgs-ggs-cgs-gcs-ccs-ccs-ags-gcs-tts-tts-ccs-ggs 5'

MP-1 oligo 2

FIG.13

SEQUENCE LISTING ( 1 ) GENERAL INFORMATION:

( i i i ) NUMBER OF SEQUENCES: 103

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Ile  Ile  Asn  Ala  Asn  Asp  Pro  Leu  Pro  Phe  Trp  Phe  Met  Ser  Pro
 1                  5                        10                       15
Tyr  Thr  Pro  Gly  Pro  Ala  Pro  Ile  Asp  Ile  Asn  Ala  Ser  Arg  Ala  Leu
               20                       25                       30
Val  Ser  Asn  Glu  Ser  Gly
               35
```

( 2 ) INFORMATION FOR SEQ ID NO:2:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp  Leu  Ser  Arg  Asn  Leu  Asp  Phe  Gly  Arg  Phe  Leu  Leu  Tyr  Asn  Ala
 1                  5                        10                       15
Tyr  Val  Pro  Gly  Phe  Thr  Pro  Thr  Phe  Ile  Ser  Leu  Thr  Ala  Glu  His
               20                       25                       30
Leu  Ser  Ser  Pro  Lys  Gly
               35
```

( 2 ) INFORMATION FOR SEQ ID NO:3:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Cys  Gly  Arg  Ala  Tyr  Cys  Leu  Ser  Gly  Asn  Tyr  Asn  Ile  Phe  Gly  Ala
 1                  5                        10                       15
Leu  Phe  Pro  Gly  Val  Ser  Thr  Pro  Tyr  Ala  Asp  Val  Gly  His  Asp  Asp
               20                       25                       30
Ala  Gln  Ser  Trp  Arg  Arg
               35
```

( 2 ) INFORMATION FOR SEQ ID NO:4:

( i ) SEQUENCE CHARACTERISTICS:
        ( A ) LENGTH: 38 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:4:

Arg Cys Ser Pro Ile Trp Gly Ile Ser Tyr Pro Phe Gly Leu Leu Ser
1               5                   10                  15

Ser Asn Pro Gly Val Cys His Ser Ser Asp Ala Glu Thr Asn Ile Arg
            20              25                  30

Asn Asp Ile Leu Thr Thr
            35

(2) INFORMATION FOR SEQ ID NO:5:

(i) SEQUENCE CHARACTERISTICS:
    (A) LENGTH: 38 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:5:

Gly His Ser Asn Tyr Cys Phe Val Ser Thr Leu Gly Met Pro Ile Val
1               5                   10                  15

Gly Phe Pro Ser Ile Asn Ala Arg Gly Leu Ile His Tyr Gly Gly Ser
            20              25                  30

Asp Pro Arg Leu Ala Ala
            35

(2) INFORMATION FOR SEQ ID NO:6:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:6:

Trp Gln Gly Thr His Phe Pro Tyr Thr
1               5

(2) INFORMATION FOR SEQ ID NO:7:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:7:

Leu Val Ser Lys Asn Asp Ser Gly
1               5

(2) INFORMATION FOR SEQ ID NO:8:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide ( x i ) SEQUENCE DESCRIPTION: SEQ ID NO:8:

Gly Ser Asp Asn Lys Ser Val Leu
1               5

( 2 ) INFORMATION FOR SEQ ID NO:9:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

Val Thr Ser Ala Pro Asp Thr Arg Pro Ala Pro Gly Ser Thr Ala Pro
1               5                              10                             15

Pro Ala His Gly Val Thr Ser Ala Pro Asp Thr Arg
                20                              25

( 2 ) INFORMATION FOR SEQ ID NO:10:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Met Tyr Xaa Xaa Leu His
1               5

( 2 ) INFORMATION FOR SEQ ID NO:11:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Ser Cys Val Ser His Met Leu Asp Thr Ser Arg Val Tyr Thr Ala Tyr
1               5                              10                             15

Ala Asn Pro Gly Met Tyr Ser Arg Leu His Ser Pro Ala Val Arg Pro
                20                              25                             30

Leu Thr Gln Ser Ser Ala
                35

( 2 ) INFORMATION FOR SEQ ID NO:12:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Ser Val Gln Phe Lys Ser Ile Ser Ser Arg Ser Met Asp Asp Val Val
1               5                              10                             15

Lys Asp Pro Gly Pro Lys Pro Ala Met Tyr Asn Arg Leu His Ser Lys
                20                              25                             30

Asn Pro Phe Thr Leu Ser
35

( 2 ) INFORMATION FOR SEQ ID NO:13:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Tyr Phe Asp His Thr Tyr Ser Gly Pro Val Val Lys Asn Gly Gly Leu
1               5                   10                  15
Val Ser Pro Gly Val Leu Ser Met Tyr Asn Arg Leu His Ser Asp Gly
            20                  25                  30
Gly Pro Ser Leu Ala Ser
35

( 2 ) INFORMATION FOR SEQ ID NO:14:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Thr Val Ala Thr Met His Asp Arg Leu His Ser Ala Pro Gly Ser Gly
1               5                   10                  15
Asn Leu Pro Gly Ser Tyr Asp Ile Lys Pro Ile Phe Lys Ala Gln Ser
            20                  25                  30
Gly Ala Leu His Ser Thr
35

( 2 ) INFORMATION FOR SEQ ID NO:15:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Ile Asp Met Pro Gln Thr Ala Ser Thr Met Tyr Asn Met Leu His Arg
1               5                   10                  15
Asn Glu Pro Gly Gly Arg Lys Leu Ser Pro Ala Asn Asp Met Pro
            20                  25                  30
Pro Ala Leu Leu Lys Arg
35

( 2 ) INFORMATION FOR SEQ ID NO:16:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Arg Leu Gly Asn His Val Trp Arg Glu Gly Gly Gly Met Tyr Gln Gln
1               5                   10                  15

Leu His His Asn Phe Pro
            20

( 2 ) INFORMATION FOR SEQ ID NO:17:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Arg Asp Ser Ala Val Glu Asn Pro Ser Val Gly Gly Glu Ile Pro Met
1               5                   10                  15

Tyr Arg Tyr Leu His Gln Arg
            20

( 2 ) INFORMATION FOR SEQ ID NO:18:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Pro Val Gln Lys Glu Tyr Gly Phe Gly Met Ser Gly Ala Ser Met Ile
1               5                   10                  15

Arg Leu Leu Arg Glu Thr Pro
            20

( 2 ) INFORMATION FOR SEQ ID NO:19:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Gln Lys Gly Gly Pro Gly Leu Leu Leu Tyr Gly Gly Asp Ser Met Tyr
1               5                   10                  15

Ile Thr Leu His Glu Pro Gly
            20

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Leu Tyr Ala Asn Pro Gly Met Tyr Ser Arg Leu His Ser Pro Ala

```
        1               5                  1 0                1 5
```

( 2 ) INFORMATION FOR SEQ ID NO:21:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

```
Gly  Met  Tyr  Ser  Arg  Leu  His  Ser  Pro  Ala
 1               5                        1 0
```

( 2 ) INFORMATION FOR SEQ ID NO:22:

( i ) SEQUENCE CHARACTERISTICS:
      ( A ) LENGTH: 35 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

```
His  Cys  Pro  Pro  Thr  Pro  Glu  Thr  Ser  Cys  Ala  Thr  Gln  Thr  Ile  Thr
 1               5                        1 0                          1 5
Phe  Glu  Ser  Phe  Lys  Glu  Asn  Leu  Lys  Asp  Phe  Leu  Leu  Val  Ile  Pro
              2 0                        2 5                     3 0
Phe  Asp  Cys
          3 5
```

( 2 ) INFORMATION FOR SEQ ID NO:23:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

```
Arg  Glu  Pro  Val  Val  Gly  Gly  Lys  Pro  Trp  Cys  Arg  Gly  Pro  Gly  Gly
 1               5                        1 0                          1 5
Leu  Arg  Trp  Arg  Gly  Cys  Gly  Lys  Ser  Gln  Phe  Asp  Lys  Ile  Ile  Thr
              2 0                        2 5                     3 0
Leu  Ser  Arg  Asp  Asn  Arg  Arg  Asp  Lys  Arg  Pro
              3 5                        4 0
```

( 2 ) INFORMATION FOR SEQ ID NO:24:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /label=Xaa
             / note= "Xaa = Gly, Cys, Glu, or Val"

( i x ) FEATURE:

-continued (A) NAME/KEY: Modified-site
(B) LOCATION: 2
(D) OTHER INFORMATION: /label=Xaa
  / note= "Xaa = Ala, Ser, Pro or Leu"

(ix) FEATURE:
(A) NAME/KEY: Modified-site
(B) LOCATION: 3
(D) OTHER INFORMATION: /label=Xaa
  / note= "Xaa = Pro, Thr, His or Leu"

(ix) FEATURE:
(A) NAME/KEY: Modified-site
(B) LOCATION: 4
(D) OTHER INFORMATION: /label=Xaa
  / note= "Xaa = Leu, Met, Gln, Gly, Ala, or Ser"

(ix) FEATURE:
(A) NAME/KEY: Modified-site
(B) LOCATION: 5
(D) OTHER INFORMATION: /label=Xaa
  / note= "Xaa = Trp or Tyr"

(ix) FEATURE:
(A) NAME/KEY: Modified-site
(B) LOCATION: 6
(D) OTHER INFORMATION: /label=Xaa
  / note= "Xaa = Ser, Cys, Lys or Thr"

(ix) FEATURE:
(A) NAME/KEY: Modified-site
(B) LOCATION: 7
(D) OTHER INFORMATION: /label=Xaa
  / note= "Xaa = Glu, Ser, Cys, Asp, Val, or Arg"

(ix) FEATURE:
(A) NAME/KEY: Modified-site
(B) LOCATION: 8
(D) OTHER INFORMATION: /label=Xaa
  / note= "Xaa = Asn, His, Lys, Ser or Glu"

(ix) FEATURE:
(A) NAME/KEY: Modified-site
(B) LOCATION: 9
(D) OTHER INFORMATION: /label=Xaa
  / note= "Xaa = Leu, His, Arg, Asn, Gln, Thr or Gly"

(ix) FEATURE:
(A) NAME/KEY: Modified-site
(B) LOCATION: 10
(D) OTHER INFORMATION: /label=Xaa
  / note= "Xaa = Trp, Pro, Arg, Thr, or Asp"

(ix) FEATURE:
(A) NAME/KEY: Modified-site
(B) LOCATION: 11
(D) OTHER INFORMATION: /label=Xaa
  / note= "Xaa = Trp, Cys, Val, Leu, or Gly"

(ix) FEATURE:
(A) NAME/KEY: Modified-site
(B) LOCATION: 12
(D) OTHER INFORMATION: /label=Xaa
  / note= "Xaa = Ser, Thr, Met, or His"

(ix) FEATURE:
(A) NAME/KEY: Modified-site
(B) LOCATION: 13
(D) OTHER INFORMATION: /label=Xaa
  / note= "Xaa = Gly"

(ix) FEATURE:
(A) NAME/KEY: Modified-site
(B) LOCATION: 14
(D) OTHER INFORMATION: /label=Xaa
  / note= "Xaa = Ser, Ala, Gly, Asn, Gln, or His"

(ix) FEATURE:
(A) NAME/KEY: Modified-site
(B) LOCATION: 15

-continued ( D ) OTHER INFORMATION: /label=Xaa
/ note= "Xaa = Trp, His, Gly, Ala, or Arg"

( i x ) FEATURE:
    ( A ) NAME/KEY: Modified-site
    ( B ) LOCATION: 16
    ( D ) OTHER INFORMATION: /label=Xaa
        / note= "Xaa = Gly, Thr, Glu, Pro, Val, or Trp"

( i x ) FEATURE:
    ( A ) NAME/KEY: Modified-site
    ( B ) LOCATION: 17
    ( D ) OTHER INFORMATION: /label=Xaa
        / note= "Xaa = Val, Phe, Trp, Lys, or Ala"

( i x ) FEATURE:
    ( A ) NAME/KEY: Modified-site
    ( B ) LOCATION: 18
    ( D ) OTHER INFORMATION: /label=Xaa
        / note= "Xaa = Lys, Gln, Asp, Glu, Arg, and Leu"

( i x ) FEATURE:
    ( A ) NAME/KEY: Modified-site
    ( B ) LOCATION: 19
    ( D ) OTHER INFORMATION: /label=Xaa
        / note= "Xaa = Arg, Phe, or Ser"

( i x ) FEATURE:
    ( A ) NAME/KEY: Modified-site
    ( B ) LOCATION: 20
    ( D ) OTHER INFORMATION: /label=Xaa
        / note= "Xaa = Pro, Ser, Ile, or His"

( i x ) FEATURE:
    ( A ) NAME/KEY: Modified-site
    ( B ) LOCATION: 21
    ( D ) OTHER INFORMATION: /label=Xaa
        / note= "Xaa = Gly"

( i x ) FEATURE:
    ( A ) NAME/KEY: Modified-site
    ( B ) LOCATION: 22
    ( D ) OTHER INFORMATION: /label=Xaa
        / note= "Xaa = Cys"

( i x ) FEATURE:
    ( A ) NAME/KEY: Modified-site
    ( B ) LOCATION: 23
    ( D ) OTHER INFORMATION: /label=Xaa
        / note= "Xaa = Gly"

( i x ) FEATURE:
    ( A ) NAME/KEY: Modified-site
    ( B ) LOCATION: 24
    ( D ) OTHER INFORMATION: /label=Xaa
        / note= "Xaa = Asp, Ser, Thr, or Asn"

( i x ) FEATURE:
    ( A ) NAME/KEY: Modified-site
    ( B ) LOCATION: 25
    ( D ) OTHER INFORMATION: /label=Xaa
        / note= "Xaa = Gly, Asp, or Leu"

( i x ) FEATURE:
    ( A ) NAME/KEY: Modified-site
    ( B ) LOCATION: 26
    ( D ) OTHER INFORMATION: /label=Xaa
        / note= "Xaa = Pro or Ser"

( i x ) FEATURE:
    ( A ) NAME/KEY: Modified-site
    ( B ) LOCATION: 27
    ( D ) OTHER INFORMATION: /label=Xaa
        / note= "Xaa = Met, Ser, Asp, Ile, Leu, or Arg"

( i x ) FEATURE:
    ( A ) NAME/KEY: Modified-site
    ( B ) LOCATION: 28
    ( D ) OTHER INFORMATION: /label=Xaa
        / note= "Xaa = Gly, Trp, Cys, Leu, Phe, Tyr, or Thr"

( i x ) FEATURE:
    ( A ) NAME/KEY: Modified-site
    ( B ) LOCATION: 29
    ( D ) OTHER INFORMATION: /label=Xaa
        / note= "Xaa = Ser, Asn, Val, Phe, His or Arg"

( i x ) FEATURE:
    ( A ) NAME/KEY: Modified-site
    ( B ) LOCATION: 30
    ( D ) OTHER INFORMATION: /label=Xaa
        / note= "Xaa = Asn, Arg, Ser, Met, or Arg"

( i x ) FEATURE:
    ( A ) NAME/KEY: Modified-site
    ( B ) LOCATION: 31
    ( D ) OTHER INFORMATION: /label=Xaa
        / note= "Xaa = Phe, Gln, Pro, or Val"

( i x ) FEATURE:
    ( A ) NAME/KEY: Modified-site
    ( B ) LOCATION: 32
    ( D ) OTHER INFORMATION: /label=Xaa
        / note= "Xaa = Ser, Val, Ile, Lys, Ala or Ser"

( i x ) FEATURE:
    ( A ) NAME/KEY: Modified-site
    ( B ) LOCATION: 33
    ( D ) OTHER INFORMATION: /label=Xaa
        / note= "Xaa = Pro, Ala, Asn, or Tyr"

( i x ) FEATURE:
    ( A ) NAME/KEY: Modified-site
    ( B ) LOCATION: 34
    ( D ) OTHER INFORMATION: /label=Xaa
        / note= "Xaa = Gly, Asn, or Leu"

( i x ) FEATURE:
    ( A ) NAME/KEY: Modified-site
    ( B ) LOCATION: 35
    ( D ) OTHER INFORMATION: /label=Xaa
        / note= "Xaa = Lys, Arg, Cys, Gln, or Leu"

( i x ) FEATURE:
    ( A ) NAME/KEY: Modified-site
    ( B ) LOCATION: 36
    ( D ) OTHER INFORMATION: /label=Xaa
        / note= "Xaa = Val, Lys, Arg, or Ala"

( i x ) FEATURE:
    ( A ) NAME/KEY: Modified-site
    ( B ) LOCATION: 37
    ( D ) OTHER INFORMATION: /label=Xaa
        / note= "Xaa = Gly, Asp, Ala, or Glu"

( i x ) FEATURE:
    ( A ) NAME/KEY: Modified-site
    ( B ) LOCATION: 38
    ( D ) OTHER INFORMATION: /label=Xaa
        / note= "Xaa = Ser, Thr, Pro, Tyr, or Trp"

( i x ) FEATURE:
    ( A ) NAME/KEY: Modified-site
    ( B ) LOCATION: 39
    ( D ) OTHER INFORMATION: /label=Xaa
        / note= "Xaa = Arg, Ile, Leu, Pro, Ala, or Ser"

( i x ) FEATURE:
    ( A ) NAME/KEY: Modified-site
    ( B ) LOCATION: 40
    ( D ) OTHER INFORMATION: /label=Xaa
        / note= "Xaa = Asn, Lys, or Met"

( i x ) FEATURE:
    ( A ) NAME/KEY: Modified-site
    ( B ) LOCATION: 41
    ( D ) OTHER INFORMATION: /label=Xaa
        / note= "Xaa = Ser, Arg, Thr, Glu, Gln, Pro, Tyr, or His"

( i x ) FEATURE:

(A) NAME/KEY: Modified-site
(B) LOCATION: 42
(D) OTHER INFORMATION: /label=Xaa
                      /note= "Xaa = Gly, Ala, Ser, Asp, Asn, Pro, Tyr, or Lys"

(ix) FEATURE:
(A) NAME/KEY: Modified-site
(B) LOCATION: 43
(D) OTHER INFORMATION: /label=Xaa
                      /note= "Xaa = Pro, His, or Ala"

(xi) SEQUENCE DESCRIPTION: SEQ ID NO:24:

Xaa Xaa Xaa Xaa Xaa Xaa Xaa Xaa Xaa Xaa Xaa Xaa Xaa Xaa Xaa Xaa
1               5                       10                      15

Xaa Xaa Xaa Xaa Xaa Xaa Xaa Xaa Xaa Xaa Xaa Xaa Xaa Xaa Xaa
                20                      25                      30

Xaa Xaa Xaa Xaa Xaa Xaa Xaa Xaa Xaa Xaa Xaa
                35                      40

(2) INFORMATION FOR SEQ ID NO:25:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: peptide (ix) FEATURE:
(A) NAME/KEY: Modified-site
(B) LOCATION: 2
(D) OTHER INFORMATION: /label=Xaa
                      /note= "Xaa = Ser or Arg"

(ix) FEATURE:
(A) NAME/KEY: Modified-site
(B) LOCATION: 15
(D) OTHER INFORMATION: /label=Xaa
                      /note= "Xaa = Ser, Pro, Thr, or Ala"

(ix) FEATURE:
(A) NAME/KEY: Modified-site
(B) LOCATION: 17
(D) OTHER INFORMATION: /label=Xaa
                      /note= "Xaa = Val, Ala, Asp, Glu, or Gly"

(xi) SEQUENCE DESCRIPTION: SEQ ID NO:25:

Ser Xaa Xaa Xaa Xaa Xaa Xaa Xaa Xaa Xaa Xaa Xaa Xaa Xaa Xaa Ala
1               5                       10                      15

Xaa Xaa Xaa Xaa Xaa Xaa Xaa Xaa Xaa Xaa Xaa Xaa Xaa Ser Arg
                20                      25                      30

(2) INFORMATION FOR SEQ ID NO:26:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:26:

Ser Phe Met Asp Tyr Phe Phe His Thr Pro Glu Pro Lys Pro Ala Gly
1               5                       10                      15

Tyr Pro Asn Ala Tyr Thr Asp Pro Lys His Pro Ala
                20                      25

(2) INFORMATION FOR SEQ ID NO:27:

( i ) SEQUENCE CHARACTERISTICS:
 ( A ) LENGTH: 28 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:27:

```
Ser  Ser  Ser  Ile  Phe  Asp  Tyr  Ala  Pro  Phe  Ser  Trp  Gly  Ser  Ala  Gly
1                   5                        10                            15

Leu  Ser  Asn  Ser  Ser  Ile  Asn  Val  Phe  Glu  Arg  Ser
                20                       25
```

( 2 ) INFORMATION FOR SEQ ID NO:28:

( i ) SEQUENCE CHARACTERISTICS:
  ( A ) LENGTH: 28 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:28:

```
Ser  Ala  Ser  Leu  Trp  Asp  Ala  Leu  Gly  Gly  Trp  Thr  Thr  Ser  Ala  Val
1                   5                        10                            15

Pro  Ser  Tyr  Pro  Arg  Pro  His  Gln  Thr  Pro  Gly  Arg
                20                       25
```

( 2 ) INFORMATION FOR SEQ ID NO:29:

( i ) SEQUENCE CHARACTERISTICS:
  ( A ) LENGTH: 28 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:29:

```
Ser  Leu  Gly  Leu  Pro  Trp  Ile  Asp  Val  Phe  Gly  Arg  Ser  Ser  Ala  Glu
1                   5                        10                            15

Pro  Trp  Pro  Phe  Gly  Arg  Thr  Asn  Leu  Pro  Arg  Ser
                20                       25
```

( 2 ) INFORMATION FOR SEQ ID NO:30:

( i ) SEQUENCE CHARACTERISTICS:
  ( A ) LENGTH: 27 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:30:

```
Ser  Val  His  Gly  Ala  Phe  Leu  Asp  Ser  Phe  Phe  Pro  Trp  Ala  Ala  Asp
1                   5                        10                            15

Gly  Pro  His  Gly  Arg  Gly  Arg  Leu  Thr  Ser  Phe
                20                       25
```

( 2 ) INFORMATION FOR SEQ ID NO:31:

( i ) SEQUENCE CHARACTERISTICS:
  ( A ) LENGTH: 43 amino acids
  ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:31:

Glu Glu Lys Gln Gly Gly Arg Trp Ser Thr Met Met Pro Arg Pro Trp
1               5                   10                  15

Cys His Glu Gly Gly Cys Gly Phe Leu Tyr Tyr Asp Ala Met Thr Lys
            20                  25                  30

Pro Lys Thr Pro Pro Ile Met Arg Thr Ala Ala
            35              40

( 2 ) INFORMATION FOR SEQ ID NO:32:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:32:

Leu Pro Arg Pro Phe Asp Asp Ala Ser Trp Lys Leu Arg Ala Val Lys
1               5                   10                  15

Glu Ser Pro Asp Gly Cys Gly Phe Gly Ser Pro Leu Leu Phe Pro Pro
            20                  25                  30

Tyr Ser Gly Leu Pro Thr Phe Ser Ser Cys Asp
            35              40

( 2 ) INFORMATION FOR SEQ ID NO:33:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Gly Ser Phe Glu Ser Ala Arg Gly Val Thr Cys Ile Gly Asn His Ser
1               5                   10                  15

Ile Gly Ala His Gly Cys Gly Pro Leu Arg Ser Tyr Ala Ser Phe Asn
            20                  25                  30

Arg Gly Ser Gly Arg Arg His
            35

( 2 ) INFORMATION FOR SEQ ID NO:34:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

Asp Gln Ile Gly Ser Arg Pro Gln Thr Thr Ser Arg Ser Ile Ser Gly
1               5                   10                  15

Ser Trp Trp Glu Asn Ala Lys Thr Leu Trp Gln Gln Asp Tyr Ala Phe
            20                  25                  30

Ser Ala Pro Asn Ala Ala 3 5

(2) INFORMATION FOR SEQ ID NO:35:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Leu Ser Asp Ala Trp Gly Asn Phe Thr Thr Ser Tyr Arg Asp Ser Ala
1               5                   10                  15

Gly Phe Pro Ser His Ala Met Thr Thr Ser Gln Gly Gly Lys Arg Asn
            20                  25                  30

His Ala Ser Arg Phe Pro
            35

(2) INFORMATION FOR SEQ ID NO:36:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Val Gln Leu Asp Asp Thr Ser Pro Arg Ala Ser Gly Gln Glu Thr Ser
1               5                   10                  15

Gln Ser Glu Tyr Asp Ala Arg Pro Leu Leu Ser Lys Phe Ala Ile Pro
            20                  25                  30

Arg Pro Trp Ser Arg
            35

(2) INFORMATION FOR SEQ ID NO:37:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Ile Asp Ser Ser Lys Asn Arg Ile Ser Gly Thr Gly Tyr Leu Ser Phe
1               5                   10                  15

Pro His Ile Arg His Ala Asn Arg Arg His Met Ala Asp Asp Ser Asn
            20                  25                  30

Leu Ala Pro Gly Pro Ser
            35

(2) INFORMATION FOR SEQ ID NO:38:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
          Trp  Ser  Ile  Gly  Thr  His  Thr  Gly  Pro  Glu  Gly  Lys  Phe  Arg  Ile  Pro
          1              5                        10                       15

Cys  Asp  Arg  Ser  Gly  Cys  Gly  Gly  Thr  Thr  Leu  Thr  His  Gly  Gly  Leu
                         20                       25                       30

Asn  Ser  Ser  Pro  Thr  Gly  Gln  His  Glu  Arg  Pro
                         35                       40
```

( 2 ) INFORMATION FOR SEQ ID NO:39:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
          Asp  Pro  Cys  Glu  Asp  Gly  Tyr  Trp  Leu  Ser  Ser  Val  Gly  Arg  Ala  Gly
          1              5                        10                       15

Ala  Ser  Ile  Arg  Gly  Cys  Gly  Ala  Ile  Arg  Arg  Ser  Ser  Arg  Thr  Leu
                         20                       25                       30

Thr  Ala  Glu  Tyr  Ser  Thr  Arg  Ala  Ser  Asn  His
                         35                       40
```

( 2 ) INFORMATION FOR SEQ ID NO:40:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
          Gly  Ser  Lys  Arg  Ser  Cys  Trp  Gly  Thr  Thr  Ile  Ser  Asn  Tyr  Phe  Arg
          1              5                        10                       15

Pro  Val  Pro  Glu  Gly  Cys  Gly  Ser  Ala  Ser  Ser  Ile  Asn  Pro  Asn  Thr
                         20                       25                       30

Asn  Thr  Gly  Arg  Leu  Pro  Ser  Leu  His  Arg  Gln
                         35                       40
```

( 2 ) INFORMATION FOR SEQ ID NO:41:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
          Ser  Ser  Ala  Ser  Ser  Gly  Cys  Leu  Gly  Arg  Ala  Glu  His  Leu  Asp  Leu
          1              5                        10                       15

Asp  Ser  Val  Trp  Gly  Cys  Gly  Ser  Gln  Ala  Asp  Met  Ser  Arg  Arg  Tyr
                         20                       25                       30

Ser  Pro  Trp  Tyr  Gly  Arg  Pro  Arg  Thr  Gly  Val
                         35                       40
```

( 2 ) INFORMATION FOR SEQ ID NO:42:

( i ) SEQUENCE CHARACTERISTICS:

(A) LENGTH: 43 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

Asn Val Met Trp Ser Ser Ser Lys Ala Gly Ile Arg Asp Cys Ser Gln
1               5                   10                  15

Val Pro Pro Gly Gly Cys Gly Pro Val Asn Arg His Arg Ala Ser Pro
            20                  25                  30

Pro Leu Thr Pro Phe Arg His Gly Ser Ile Arg
            35                  40

(2) INFORMATION FOR SEQ ID NO:43:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:43:

Pro Leu Thr Ser Gly Ser Ser Ser Glu Tyr Arg Asn Arg Asp Asp Cys
1               5                   10                  15

Pro Val Tyr Lys Tyr Ala Thr Asn Cys Pro Arg Leu Asn Phe Ser Pro
            20                  25                  30

Ser Arg Tyr Ser Pro Phe
            35

(2) INFORMATION FOR SEQ ID NO:44:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:44:

Gly Asp Ala Tyr Gly Gly Ile Phe Ser Arg Pro Arg Gln Gly Leu Ala
1               5                   10                  15

Asp Ser Tyr Ile His Ala Ser Tyr Thr Gly Lys His Phe Phe Arg Gly
            20                  25                  30

Pro Arg Pro Pro Thr Arg
            35

(2) INFORMATION FOR SEQ ID NO:45:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:45:

Ser Thr Cys Ile Gly Ala Glu Gly Glu Trp Lys Ser Phe His Asn Phe
1               5                   10                  15

Leu Gln Cys Arg Asp Ala Thr Ser Thr Ser Ser Thr Leu Asp Pro
            20                  25                  30

Thr Ala Leu Arg Phe Gly
            35

( 2 ) INFORMATION FOR SEQ ID NO:46:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

Tyr Ser Ala Thr Leu Trp Asp Gln Phe Gly Ser Arg Gln Val Glu Leu
1                     5                         10                        15
Trp Ser Asn Arg His Ala Ser Ser Ala Leu Pro Phe Ala Ser Arg Ala
                 20                        25                        30
Ser Val Leu Gly Ser Arg
            35

( 2 ) INFORMATION FOR SEQ ID NO:47:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

Ile Leu Gly Trp Pro Phe Leu Thr Gly Leu Gly Asp Ser Thr Val His
1                     5                         10                        15
Pro Arg Gly Arg Lys Gly Thr Asp Pro Ser
                 20                        25

( 2 ) INFORMATION FOR SEQ ID NO:48:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

Ser Ile Pro Ser Phe Ser Met Trp Leu Asn Gln Leu Gly Ser Ala Ala
1                     5                         10                        15
Leu Pro Ser Lys Gly Asn Ser Gln Asp Arg Ser Asp
                 20                        25

( 2 ) INFORMATION FOR SEQ ID NO:49:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

Ser Arg Asp Asp Ile Phe Thr Gly Gly Pro Leu Val Leu Phe Arg Gly
1                     5                         10                        15

Ser Lys Thr Ser Asn His Asp Val His Ser Met Arg
                20                  25

(2) INFORMATION FOR SEQ ID NO:50:

(i) SEQUENCE CHARACTERISTICS:
       (A) LENGTH: 28 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:50:

Arg Ala Glu Leu Val Asn Trp Tyr Glu Trp Phe His Val Thr Ala Glu
1               5                   10                  15

Ala Glu Thr Pro Val Ile Asn Ser His Asn Met Thr
                20                  25

(2) INFORMATION FOR SEQ ID NO:51:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:51:

Gly Ala Pro Val Trp Arg Gly Asn Pro Arg Trp Arg Gly Pro Gly Gly
1               5                   10                  15

Phe Lys Trp Pro Gly Cys Gly Asn Gly Pro Met Cys Asn Thr Phe Thr
                20                  25                  30

Pro Ala Arg Gly Gly Ser Arg Asn Asn Gly Pro
                35                  40

(2) INFORMATION FOR SEQ ID NO:52:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:52:

Gly Ser Ala Ser Ser Cys Phe Pro Asn Phe Thr Ala Arg Gly Val Thr
1               5                   10                  15

Val Gly Phe Phe Gly Cys Gly Ser Pro Ala His Pro Ala Ala Pro Arg
                20                  25                  30

Val Leu Asn Pro Ala Thr Asp Phe Pro Ala Pro
                35                  40

(2) INFORMATION FOR SEQ ID NO:53:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:53:

Val Phe Arg Arg Thr Ala Arg Ser Ser Arg Pro Ile Gly Ala Thr Val

|     | 1       |       |       |       | 5     |       |       |       |       | 10    |       |       |       |       | 15    |
| --- | ---     | ---   | ---   | ---   | ---   | ---   | ---   | ---   | ---   | ---   | ---   | ---   | ---   | ---   | ---   |
|     | Phe     | Pro   | Trp   | Tyr   | Gly   | Cys   | Gly   | Asn   | Ser   | Asn   | Asp   | Glu   | Thr   | Leu   | Pro   | His |
|     |         |       |       | 20    |       |       |       |       | 25    |       |       |       |       | 30    |
|     | His     | Asp   | Ser   | Pro   | Pro   | Ser   | Phe   | Phe   | Leu   | Gly   | Ala   |
|     |         |       | 35    |       |       |       | 40    |

( 2 ) INFORMATION FOR SEQ ID NO:54:

( i ) SEQUENCE CHARACTERISTICS:
    ( A ) LENGTH: 42 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:54:

| Asn | Thr | Cys | Trp | Thr | Asp | Leu | Phe | Trp | His | Gly | Leu | Pro | Gly | Gly | Asp |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |
| Leu | Pro | Arg | Asp | Gly | Cys | Gly | Leu | Pro | Ser | Glu | Leu | Thr | Thr | His | Pro |
|     |     |     | 20  |     |     |     |     | 25  |     |     |     |     | 30  |
| Ser | Arg | Glu | Arg | Arg | Asp | Ala | Ser | Glu | Asn |
|     |     |     | 35  |     |     |     |     | 40  |

( 2 ) INFORMATION FOR SEQ ID NO:55:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:55:

| Ile | Asp | Trp | Asn | Trp | Leu | Glu | Arg | Gly | Gln | His | Asn | Arg | Gly | Tyr | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |
| His | Ser | Phe | Pro | Asp | Ala | Lys | Ser | Gln | Pro | Thr | Arg | Gly | Pro | Arg | Val |
|     |     |     | 20  |     |     |     |     | 25  |     |     |     |     | 30  |
| Ala | Pro | Asn | Gly | Asn | Asp |
|     |     |     | 35  |

( 2 ) INFORMATION FOR SEQ ID NO:56:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:56:

| Gly | Arg | Gly | Ser | Asp | Met | Arg | Glu | His | Trp | Pro | Trp | Ser | Met | Pro | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |
| Ile | Leu | Asp | Gln | His | Ala | Asn | Asp | Pro | Ser | Pro | Arg | Ala | Gln | Ser | His |
|     |     |     | 20  |     |     |     |     | 25  |     |     |     |     | 30  |
| Tyr | Tyr | Ser | His | Pro | Phe |
|     |     |     | 35  |

( 2 ) INFORMATION FOR SEQ ID NO:57:

( i ) SEQUENCE CHARACTERISTICS:
    ( A ) LENGTH: 43 amino acids
    ( B ) TYPE: amino acid (C) STRANDEDNESS: single
            (D) TOPOLOGY: linear (ii) MOLECULE TYPE: peptide (xi) SEQUENCE DESCRIPTION: SEQ ID NO:57:

Val  Ser  Thr  Gly  Trp  Ser  Gly  Thr  Pro  Arg  Trp  Cys  Ala  Pro  Gly  Gly
    1                   5                        10                       15

Lys  Gln  Gly  Ser  Gly  Cys  Gly  Asn  Gly  Pro  Arg  Trp  Thr  Thr  Leu  Thr
                   20                       25                       30

Pro  Asp  Leu  Gly  Gly  Thr  Arg  Lys  Tyr  Gly  Pro
                   35                       40

(2) INFORMATION FOR SEQ ID NO:58:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:58:

Gly  Ala  Pro  Leu  Trp  Cys  Glu  Lys  Leu  Ser  Gly  Thr  Gly  Ser  Gly  Gly
    1                   5                        10                       15

Phe  Lys  Trp  Pro  Gly  Cys  Gly  Ser  Gly  Pro  Thr  Tyr  Asn  Thr  Phe  Thr
                   20                       25                       30

Pro  Ala  Arg  Val  Gly  Ser  Asp  Asn  Lys  Trp  Pro
                   35                       40

(2) INFORMATION FOR SEQ ID NO:59:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:59:

Gly  Pro  Pro  Val  Trp  Ser  Ala  Lys  Ser  Arg  Trp  Thr  Gly  Thr  Gly  Val
    1                   5                        10                       15

Leu  Asn  Trp  Pro  Gly  Cys  Gly  Lys  Val  Pro  Ser  Cys  Ser  Thr  Tyr  Thr
                   20                       25                       30

Pro  Ser  Arg  Asp  Arg  Ser  Arg  Lys  Ser  Asp  Pro
                   35                       40

(2) INFORMATION FOR SEQ ID NO:60:

(i) SEQUENCE CHARACTERISTICS:
            (A) LENGTH: 43 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:60:

Gly  Ser  Ala  Leu  Leu  Thr  Ser  Lys  Gly  Cys  Val  Arg  Gly  Pro  Gly  Gly
    1                   5                        10                       15

Leu  Met  Arg  Pro  Gly  Cys  Gly  Asn  Asp  Arg  Leu  Gly  Lys  Ser  Ser  Thr
                   20                       25                       30

Tyr  Ala  His  Gly  Gly  Trp  Ile  Lys  Thr  Gly  Pro 3 5                                         4 0

( 2 ) INFORMATION FOR SEQ ID NO:61:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

Gly   Ser   Pro   Val   Trp   Ser   Gly   Asp   Asn   Arg   Trp   Arg   Gly   Ser   Ser   Pro
1                        5                             10                             1 5

Leu   Lys   Arg   Pro   Gly   Cys   Gly   Asn   Gly   Ala   Lys   Cys   Asn   Thr   Leu   Lys
                  2 0                           2 5                           3 0

Asp   Asn   Arg   Lys   Asp   Ser   Arg   Lys   Thr   Lys   His
                  3 5                           4 0

( 2 ) INFORMATION FOR SEQ ID NO:62:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

Gly   Pro   Leu   Leu   Pro   Gly   Glu   Ala   Ala   Val   His   Gly   Ala   Arg   Gly   Leu
1                        5                             10                             1 5

Met   Arg   Ser   Gly   Cys   Gly   Asn   Gly   Pro   Thr   Trp   Asn   Arg   Leu   Thr   Ala
                  2 0                           2 5                           3 0

Ala   Cys   Arg   Asp   Ser   Arg   Asn   Lys   Gly   Pro
                  3 5                           4 0

( 2 ) INFORMATION FOR SEQ ID NO:63:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

Gly   Ser   Pro   Val   Trp   Met   Gly   Ser   Thr   Arg   Trp   Thr   Gly   His   Gly   Trp
1                        5                             10                             1 5

Phe   Arg   Ser   Gln   Gly   Cys   Gly   Asn   Val   Pro   Arg   Thr   Asn   Ser   Cys   Ala
                  2 0                           2 5                           3 0

Pro   Ala   Gly   Lys   Asp   Ser   Gln   Asn   Lys   Gly   Pro
                  3 5                           4 0

( 2 ) INFORMATION FOR SEQ ID NO:64:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

```
Gly  Ala  Pro  Val  Trp  Arg  Gly  Asn  Arg  Trp  Cys  Ser  Asp  Asn  Gly  Glu
 1              5                        10                        15

Leu  Glu  Arg  Pro  Gly  Cys  Gly  Tyr  Gly  Pro  Arg  Phe  Asn  Ile  Leu  Pro
               20                       25                       30

Pro  Gly  Arg  Gly  Asn  Ser  Arg  Lys  Pro  Ser  Pro
               35                  40
```

(2) INFORMATION FOR SEQ ID NO:65:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:65:

```
Gly  Ser  Ser  Gly  Trp  Lys  Val  Lys  His  Arg  Cys  Gly  Gly  Pro  Gly  Thr
 1              5                        10                        15

Leu  Gln  Arg  Pro  Gly  Cys  Gly  Asn  Leu  Pro  Leu  Gly  His  Thr  Phe  Pro
               20                       25                       30

Pro  Thr  Arg  Gly  Gly  Ser  His  Met  Glu  Gly  Ala
               35                  40
```

(2) INFORMATION FOR SEQ ID NO:66:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:66:

```
Gly  Pro  Arg  Ser  Trp  Met  Gly  Gln  Pro  Arg  Gly  Ser  Asp  Ala  Gly  Ser
 1              5                        10                        15

Cys  Lys  Trp  Ala  Gly  Cys  Gly  Asp  Ala  Pro  Met  Trp  Arg  Ala  Ser  Thr
               20                       25                       30

Pro  Gly  His  Gly  Gly  Pro  Pro  Asn  Arg  Gly  Ser
               35                  40
```

(2) INFORMATION FOR SEQ ID NO:67:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:67:

```
Glu  Ala  Leu  Val  Cys  Arg  Gly  Lys  Pro  Pro  Trp  Ser  Gly  Pro  Ala  Gly
 1              5                        10                        15

Leu  Leu  Trp  Gln  Gly  Cys  Gly  Thr  Gly  Pro  Val  Ser  Arg  Thr  Phe  Thr
               20                       25                       30

Ser  Ala  Gln  Gly  Arg  Ser  Arg  Asn  Lys  Thr  Ser
               35                  40
```

(2) INFORMATION FOR SEQ ID NO:68:

(i) SEQUENCE CHARACTERISTICS:

(A) LENGTH: 43 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:68:

Gly Ala Pro Val Val Gly Asp Ile Leu Trp Cys Ser Gly Ala Arg Gly
1               5                   10                  15

Ala Lys Trp Pro Gly Cys Gly Lys Gly Pro Thr Asn Lys Thr Phe Ser
            20                  25                  30

His Ser Arg Gly Gly Thr Gln Lys Ser Gly Leu
        35                  40

(2) INFORMATION FOR SEQ ID NO:69:

(i) SEQUENCE CHARACTERISTICS:
    (A) LENGTH: 43 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:69:

Gly Ala Pro Val Ser Arg Cys Lys Pro Ala Cys Gly Gly Phe Trp Gly
1               5                   10                  15

Val Asn Trp Pro Gly Cys Gly Asn Ala Ser Met Cys Lys Thr Phe Thr
            20                  25                  30

Asn Gly His Gly Val Ser Ser Asp Asn Gly His
        35                  40

(2) INFORMATION FOR SEQ ID NO:70:

(i) SEQUENCE CHARACTERISTICS:
    (A) LENGTH: 43 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:70:

Gly Ala His Gly Tyr Lys Asn Gly Ser Thr Cys Thr Gly Leu Gly Gly
1               5                   10                  15

Trp Arg Cys Arg Gly Cys Gly Lys Gly Ala Met Cys Asn Asn Pro Ser
            20                  25                  30

Pro Ala Gly Gly Ala Tyr His Asn Gln Gly Pro
        35                  40

(2) INFORMATION FOR SEQ ID NO:71:

(i) SEQUENCE CHARACTERISTICS:
    (A) LENGTH: 42 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:71:

Gly Pro Gln Gly Ser Glu His Gln Cys Cys Ser Gly His Trp Gly Leu
1               5                   10                  15

Lys Phe Pro Gly Cys Gly Asn Gly Pro Ile Cys Asn Asn Phe Thr Ala
            20                  25                  30

```
        Leu  Arg  Gly  Ala  Ser  Arg  Lys  Asn  Gly  Pro
                  35                  40
```

( 2 ) INFORMATION FOR SEQ ID NO:72:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

```
Gly  Glu  Pro  Val  Trp  Cys  Arg  His  Ser  Gly  Gly  Arg  Val  Gln  Gly  Gly
1              5                        10                            15
Leu  Asp  Trp  Leu  Gly  Cys  Gly  Asp  Gly  Pro  Leu  Arg  Tyr  Thr  Val  Thr
               20                      25                       30
Pro  Ala  Arg  Gly  Gly  Pro  Ser  Lys  His  Gly  Pro
               35                  40
```

( 2 ) INFORMATION FOR SEQ ID NO:73:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

```
Gly  Leu  Ser  Leu  Val  Arg  Gly  Asp  Ser  Trp  Gly  Ser  Gly  Ala  Gly  Gly
1              5                        10                            15
Trp  Lys  Arg  His  Gly  Cys  Gly  His  Gly  Pro  Met  Tyr  Asn  Pro  Gln  Thr
               20                      25                       30
Pro  Ala  Arg  Gly  Gly  Ser  Cys  Thr  Arg  Asn  Thr
               35                  40
```

( 2 ) INFORMATION FOR SEQ ID NO:74:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

```
Val  Ser  Arg  Ala  Trp  Ser  Gly  Lys  Pro  Arg  Leu  Met  Gly  Ser  His  Gly
1              5                        10                            15
Leu  Asn  Cys  Pro  Gly  Cys  Gly  Lys  Gly  His  Ser  Gly  Ile  Met  Phe  Ile
               20                      25                       30
Pro  Asp  Pro  Ala  Gly  Ser  Ala  Asn  Thr  Pro  Pro
               35                  40
```

( 2 ) INFORMATION FOR SEQ ID NO:75:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

Cys Ala Pro Met Trp Ser Gly Lys Pro Pro Trp Cys Val Gly Gly Gly
1               5                   10                  15

Val Lys Phe Arg Gly Cys Gly Asn Arg Pro Asp Cys Asn Ile Ile Thr
            20                  25                  30

Pro Arg Leu Val Glu Ser Arg Asp Lys Ala Leu
            35              40

( 2 ) INFORMATION FOR SEQ ID NO:76:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:76:

Ala Asp Pro Val Cys Ser Arg Lys Pro Asp Gly Gly Leu Arg Gly
1               5                   10                  15

Leu Arg Trp Pro Gly Cys Gly Lys Gly Pro Ile Leu Tyr Asn Val Thr
            20                  25                  30

Ala Ala Arg Gly Gly Ser Arg Asn Asn Gly Pro
            35              40

( 2 ) INFORMATION FOR SEQ ID NO:77:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:77:

Gly Thr Arg Val Pro Pro Gly Phe Ala Leu Arg Gly Gly Arg Asp Gly
1               5                   10                  15

Leu Ser Trp Ala Gly Cys Gly Lys Ala Pro Ile Ser Lys Thr Tyr Thr
            20                  25                  30

Ser Ala Arg Gly Arg Ser Arg Lys Lys Gly Ser
            35              40

( 2 ) INFORMATION FOR SEQ ID NO:78:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:78:

Arg Ser Ala Val Ser Glu Gly Lys Pro Arg Glu Ile Val Pro Gly Gly
1               5                   10                  15

Cys Met Trp Pro Gly Cys Gly Asn Gly Arg Lys Ser Asn Thr Leu Thr
            20                  25                  30

His Gly Pro Glu Gln Phe Gln Glu Ile Glu Pro
            35              40

( 2 ) INFORMATION FOR SEQ ID NO:79:

( i ) SEQUENCE CHARACTERISTICS:
  ( A ) LENGTH: 42 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:79:

| Ser | Ser | Gly | Val | Gly | Asn | Gly | Lys | Pro | Arg | Ser | Trp | Ala | Pro | Asp | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Asn | Gly | Gly | Cys | Gly | Asn | Ile | Gln | Phe | Ala | Asn | Thr | Ile | Thr | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Arg | Gly | Gly | Ser | Cys | Asn | Gln | Thr | Leu |
|-----|-----|-----|-----|-----|-----|-----|-----|-----|-----|
|     |     | 35  |     |     |     |     | 40  |     |     |

( 2 ) INFORMATION FOR SEQ ID NO:80:

( i ) SEQUENCE CHARACTERISTICS:
  ( A ) LENGTH: 43 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:80:

| Gly | Ser | Ser | Val | Cys | Gly | Gly | Gln | Pro | Ser | Gly | Arg | Gly | Phe | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Pro | Gly | Pro | Gly | Cys | Gly | Asn | Gly | Pro | Thr | Ser | Asn | Thr | Leu | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Ala | Arg | Gly | Gly | Phe | Pro | Asn | Lys | Gly | Leu |
|-----|-----|-----|-----|-----|-----|-----|-----|-----|-----|-----|
|     |     | 35  |     |     |     |     | 40  |     |     |     |

( 2 ) INFORMATION FOR SEQ ID NO:81:

( i ) SEQUENCE CHARACTERISTICS:
  ( A ) LENGTH: 43 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:81:

| Gly | Ala | Pro | Leu | Trp | Gln | Gly | Asp | Pro | Ala | Asp | Glu | Val | Leu | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Met | Ile | Pro | Gly | Cys | Gly | Ile | Gly | Ala | Leu | Ser | Gln | Thr | Phe | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Thr | Pro | Gly | Gly | Ser | Arg | Lys | Asn | Val | Thr |
|-----|-----|-----|-----|-----|-----|-----|-----|-----|-----|-----|
|     |     | 35  |     |     |     |     | 40  |     |     |     |

( 2 ) INFORMATION FOR SEQ ID NO:82:

( i ) SEQUENCE CHARACTERISTICS:
  ( A ) LENGTH: 42 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:82:

| Ala | Gly | Arg | Glu | Leu | Arg | Gln | Asp | Glu | Gly | Glu | Gly | Gly | Ala | Gly | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asp Val Ala Arg Leu Arg Glu Gly Pro Ile Cys Ser Thr Phe Thr Pro
                20                  25                  30

Ala Arg Gly Gly Ser Cys Pro Ser Gly Leu
        35                  40

( 2 ) INFORMATION FOR SEQ ID NO:83:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

Gln Ala Arg Val Ser Met Ala Ile Ser Cys Arg Ser Gly Pro Ser Asp
1                   5                   10                  15

Leu Met His Gln Gly Cys Gly Tyr Gly Pro Arg Cys Asn Pro Asp Thr
                20                  25                  30

Thr Asp Ser Gly Gly Ser His Thr Asn Thr Pro
            35                  40

( 2 ) INFORMATION FOR SEQ ID NO:84:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

Gly Asp Pro Glu Cys Arg Gly Lys Pro Arg Gly Arg Trp Thr Gly Ser
1                   5                   10                  15

Leu Ala Cys Thr Gly Cys Gly Asn Gly Pro Asn Ser Lys Ile Cys Thr
                20                  25                  30

Arg Ala Arg Gly Val Ser Arg Asn Lys Gly Pro
            35                  40

( 2 ) INFORMATION FOR SEQ ID NO:85:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

Ser Thr Pro Gly Cys Ser Gly Tyr Ser Gly Ser Gly Asp Pro Arg Cys
1                   5                   10                  15

Leu Thr Cys Thr Ala Cys Gly Asn Gly His Thr Arg Lys Thr Leu Thr
                20                  25                  30

Pro Ala His Gly Arg Ser Thr His Lys Glu Pro
            35                  40

( 2 ) INFORMATION FOR SEQ ID NO:86:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:86:

Gly Gln Pro Glu Cys Arg Ile Thr Ser Gly Cys Cys Gly Thr Asp Gly
1               5                   10                  15

Asn Lys Trp Leu Gly Cys Gly Lys Val Asp Met Cys Asn Thr Leu Asn
            20                  25                  30

Pro Ala Val Gly Cys His Gly Thr Asn Gly Ser
            35                  40

(2) INFORMATION FOR SEQ ID NO:87:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:87:

CTGTGCCTCG AGBNNBNNBN NBNNBNNBNN BNNBNNBNNB NNBNNBNNBN CCGCGG    56

(2) INFORMATION FOR SEQ ID NO:88:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:88:

CTGTGCTCTA GAVNNVNNVN NVNNVNNVNN VNNVNNVNNV NNVNNVNNVN CCGCGG    56

(2) INFORMATION FOR SEQ ID NO:89:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:89:

TCGAGBNNBN NBNNBNNBNN BNNBNNBNNB NNBNNBNNBN NBNCCGCGG    49

(2) INFORMATION FOR SEQ ID NO:90:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:90:

CTAGTVNNVN NVNNVNNVNN VNNVNNVNNV NNVNNVNNVN NVNCCGCGG    49

(2) INFORMATION FOR SEQ ID NO:91:

(i) SEQUENCE CHARACTERISTICS:
        (A) LENGTH: 38 amino acids
        (B) TYPE: amino acid ( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Xaa
/ note= "Xaa = Ser or Arg"

( i x ) FEATURE:
( A ) NAME/KEY: Modified-site
( B ) LOCATION: 18
( D ) OTHER INFORMATION: /label=Xaa
/ note= "Xaa = Ser, Pro, Thr, or Ala"

( i x ) FEATURE:
( A ) NAME/KEY: Modified-site
( B ) LOCATION: 20
( D ) OTHER INFORMATION: /label=Xaa
/ note= "Xaa = Val, Ala, Asp, Glu, or Gly"

( x i ) SEQUENCE DESCRIPTION: SEQ ID NO:91:

Ser His Ser Ser Xaa Xaa Xaa Xaa Xaa Xaa Xaa Xaa Xaa Xaa Xaa Xaa
1               5                       10                      15

Xaa Xaa Ala Xaa Xaa Xaa Xaa Xaa Xaa Xaa Xaa Xaa Xaa Xaa Xaa Xaa
            20                      25                      30

Ser Arg Pro Ser Arg Thr
            35

( 2 ) INFORMATION FOR SEQ ID NO:92:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:92:

GTGTGTCTCG AGNNNBNNBN NBNNBNNBNN BNNBNNBNNB NNBNNBNNBN NBNNBNNBNN    60

BNNBNNBNNB NNBNACGCCA N    81

( 2 ) INFORMATION FOR SEQ ID NO:93:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:93:

GTTGTGTCTA GAVNNVNNVN NVNNVNNVNN VNNVNNVNNV NNVNNVNNVN NVNNVNNVNT    60

GGCGTN    66

( 2 ) INFORMATION FOR SEQ ID NO:94:

( i ) SEQUENCE CHARACTERISTICS:
( A ) LENGTH: 74 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:94:

TCGAGNNNBN NBNNBNNBNN BNNBNNBNNB NNBNNBNNBN NBNNBNNBNN BNNBNNBNNB 60

NNBNNBNACG CCAN 74

(2) INFORMATION FOR SEQ ID NO:95:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:95:

CTAGAVNNVN NVNNVNNVNN VNNVNNVNNV NNVNNVNNVN NVNNVNNVNN VNTGGCGTN 59

(2) INFORMATION FOR SEQ ID NO:96:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /label=Xaa
           / note= "Xaa = Ser or Arg"

(ix) FEATURE:
        (A) NAME/KEY: Modified-site
        (B) LOCATION: 25
        (D) OTHER INFORMATION: /label=Xaa
           / note= "Xaa = Tyr, His, Asn or Asp"

(ix) FEATURE:
        (A) NAME/KEY: Modified-site
        (B) LOCATION: 27
        (D) OTHER INFORMATION: /label=Xaa
           / note= "Xaa = Ile, Met, Thr, Asn, Lys, Ser, or Arg"

(xi) SEQUENCE DESCRIPTION: SEQ ID NO:96:

His Ser Ser Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Ala Xaa Xaa Xaa Xaa Xaa Xaa
            20                  25                  30

Xaa Xaa Xaa Xaa Xaa Xaa Xaa Xaa Xaa Xaa Ser Arg
            35                  40

(2) INFORMATION FOR SEQ ID NO:97:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

GTGTGTCTCG AGNNNBNNBN NBNNBNNBNN BNNBNNBNNB NNBNNBNNBN NBNNBNNBNN 60

BNNBNNBNNB NNBGGTTGTG GT 82

(2) INFORMATION FOR SEQ ID NO:98:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:98:

GTTGTGTCTA GAVNNVNNVN NVNNVNNVNN VNNVNNVNNV NNVNNVNNVN NVNNVNNVNN 60

VNNVNNVNNV NNACCACAAC C 81

( 2 ) INFORMATION FOR SEQ ID NO:99:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:99:

TCGAGNNNBN NBNNBNNBNN BNNBNNBNNB NNBNNBNNBN NBNNBNNBNN BNNBNNBNNB 60

NNBNNBGGTT GTGGT 75

( 2 ) INFORMATION FOR SEQ ID NO:100:

( i ) SEQUENCE CHARACTERISTICS:
( A ) LENGTH: 74 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:100:

CTAGAVNNVN NVNNVNNVNN VNNVNNVNNV NNVNNVNNVN NVNNVNNVNN VNNVNNVNNV 60

NNVNNACCAC AACC 74

( 2 ) INFORMATION FOR SEQ ID NO:101:

( i ) SEQUENCE CHARACTERISTICS:
( A ) LENGTH: 49 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 4
( D ) OTHER INFORMATION: /label=Xaa
/ note= "Xaa = Ser or Arg"

( x i ) SEQUENCE DESCRIPTION: SEQ ID NO:101:

His Ser Ser Xaa Xaa Xaa Xaa Xaa Xaa Xaa Xaa Xaa Xaa Xaa Xaa
1               5                       10                      15

Xaa Xaa Xaa Xaa Xaa Xaa Xaa Xaa Gly Cys Gly Xaa Xaa Xaa Xaa
                20                      25                      30

Xaa Xaa Xaa Xaa Xaa Xaa Xaa Xaa Xaa Xaa Xaa Xaa Xaa Xaa Ser
            35                      40                      45

Arg ( 2 ) INFORMATION FOR SEQ ID NO:102:

(i) SEQUENCE CHARACTERISTICS:
  (A) LENGTH: 69 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:102:

GGSGCSCCSG TSTGSAGSGG SAASCCSCGS TGSAGSGGSC CSGGSGGSTT SAASTGSCCS    60

GGCTGCGGG    69

(2) INFORMATION FOR SEQ ID NO:103:

(i) SEQUENCE CHARACTERISTICS:
    (A) LENGTH: 69 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:103:

SGGSCCSTTS TTSCGSGASC CSCCSCGSGC SGGSGTSAAS GTSTTSCASA TSGGSCCSTT    60

CCCGCAGCC    69

ANTIGEN BINDING PEPTIDES (ABTIDES) FROM PEPTIDE LIBRARIES

This application is a continuation-in-part of co-pending U.S. patent application Ser. No. 08/310,192 filed Sep. 21, 1994, the entire contents of which are incorporated herein by reference.

1. FIELD OF THE INVENTION

The present invention relates generally to peptides capable of specific binding to ligands of interest. The present invention also relates to peptides capable of mimicking the specific binding of a receptor to its ligand, an antibody to its antigen, and the like. Such peptides are known as "abtides." Abtides are identified by first and second screening steps of peptide libraries. The first screening step uses an antibody or receptor as a first target ligand and identifies peptide sequences ("mimetopes") which specifically bind to the antibody or receptor. The mimetopes are then incorporated into a second target ligand in a second screening step to identify abtides that bind the mimetope. Abtides mimic the binding specificity of the antibody (to its antigen) or the receptor (to its ligand) that was used as the first target ligand in the first screening step. The invention further relates to the use of abtides in the place of antibodies in assays. The invention also provides abtide compositions for use in therapy and diagnosis of disease.

2. BACKGROUND OF THE INVENTION

2.1. PEPTIDE LIBRARIES

The use of peptide libraries is well known in the art. Such peptide libraries have generally been constructed by one of two approaches. According to one approach, peptides have been chemically synthesized in vitro in several formats. For example, Fodor et al., 1991, Science 251: 767–773, describes use of complex instrumentation, photochemistry and computerized inventory control to synthesize a known array of short peptides on an individual microscopic slide. Houghten et al., 1991, Nature 354: 84–86, describes mixtures of free hexapeptides in which the first and second residues in each peptide were individually and specifically defined. Lam et al., 1991, Nature 354: 82–84, describes a "one bead, one peptide" approach in which a solid phase split synthesis scheme produced a library of peptides in which each bead in the collection had immobilized thereon a single, random sequence of amino acid residues. For the most part, the chemical synthetic systems have been directed to generation of arrays of short length peptides, generally fewer than about 10 amino acids or so, more particularly about 6–8 amino acids. Direct amino acid sequencing, alone or in combination with complex record keeping of the peptide synthesis schemes, is required to use these libraries.

According to a second approach using recombinant DNA techniques, peptides have been expressed in biological systems as either soluble fusion proteins or viral capsid fusion proteins.

A number of peptide libraries according to the second approach have used the M13 phage. M13 is a filamentous bacteriophage that has been a workhorse in molecular biology laboratories for the past 20 years. M13 viral particles consist of six different capsid proteins and one copy of the viral genome, as a single-stranded circular DNA molecule. Once the M13 DNA has been introduced into a host cell such as $E.\ coli$, it is converted into double-stranded, circular DNA. The viral DNA carries a second origin of replication that is used to generate the single-stranded DNA found in the viral particles. During viral morphogenesis, there is an ordered assembly of the single-stranded DNA and the viral proteins, and the viral particles are extruded from cells in a process much like secretion. The M13 virus is neither lysogenic nor lytic like other bacteriophage (e.g., $\lambda$); cells, once infected, chronically release virus. This feature leads to high titers of virus in infected cultures, i.e., $10^{12}$ pfu/ml.

The genome of the M13 phage is ~8000 nucleotides in length and has been completely sequenced. The viral capsid protein, protein III (pIII) is responsible for infection of bacteria. In $E.\ coli$, the pillin protein encoded by the F factor interacts with pIII protein and is responsible for phage uptake. Hence, all $E.\ coli$ hosts for M13 virus are considered male because they carry the F factor. Several investigators have determined from mutational analysis that the 406 amino acid long pIII capsid protein has two domains. The C-terminus anchors the protein to the viral coat, while portions of the N-terminus of pIII are essential for interaction with the $E.\ coli$ pillin protein (Crissman and Smith, 1984, Virology 132: 445–455). Although the N-terminus of the pIII protein has been shown to be necessary for viral infection, the extreme N-terminus of the mature protein does tolerate alterations. In 1985, George Smith published experiments reporting the use of the pIII protein of bacteriophage M13 as an experimental system for expressing a heterologous protein on the viral coat surface (Smith, 1985, Science 228: 1315–1317). It was later recognized, independently by two groups, that the M13 phage pIII gene display system could be a useful one for mapping antibody epitopes. De la Cruz et al., 1988, J. Biol. Chem. 263: 4318–4322 cloned and expressed segments of the cDNA encoding the Plasmodium falciparum surface coat protein into the pIII gene, and recombinant phage were tested for immunoreactivity with a polyclonal antibody. Parmley and Smith, 1988, Gene 73: 305–318 cloned and expressed segments of the $E.\ coli$ $\beta$-galactosidase gene in the pIII gene and identified recombinants carrying the epitope of an anti-$\beta$-galactosidase monoclonal antibody. The latter authors also described a process termed "biopanning", in which mixtures of recombinant phage were incubated with biotinylated monoclonal antibodies, and phage-antibody complexes could be specifically recovered with streptavidin-coated plastic plates.

In 1989, Parmley and Smith, 1989, Adv. Exp. Med. Biol. 251:215–218 suggested that short, synthetic DNA segments cloned into the pIII gene might represent a library of epitopes. These authors reasoned that since linear epitopes were often ~6 amino acids in length, it should be possible to use a random recombinant DNA library to express all possible hexapeptides to isolate epitopes that bind to antibodies.

Scott and Smith, 1990, Science 249:386–390 describe construction and expression of an "epitope library" of hexapeptides on the surface of M13. The library was made by inserting a 33 base pair Bgl I digested oligonucleotide sequence into an Sfi I digested phage fd-tet, i.e., fUSE5 RF. The 33 base pair fragment contains a random or "degenerate" coding sequence $(NNK)_6$ where N represents G, A, T or C and K represents G or T. The authors stated that the library consisted of $2\times10^8$ recombinants expressing $4\times10^7$ different hexapeptides; theoretically, this library expressed 69% of the $6.4\times10^7$ possible peptides ($20^6$). Cwirla et al., 1990, Proc. Natl. Acad. Sci. USA 87: 6378–6382 also described a somewhat similar library of hexapeptides expressed as pIII gene fusions of M13 fd phage. PCT publication WO 91/19818 dated Dec. 26, 1991 by Dower and Cwirla describes a similar library of pentameric to octameric random amino acid sequences.

Devlin et al., 1990, Science, 249:404–406, describes a peptide library of about 15 residues generated using an (NNS) coding scheme for oligonucleotide synthesis in which S is G or C.

Christian and colleagues have described a phage display library, expressing decapeptides (Christian et al., 1992, J. Mol. Biol. 227:711–718). The starting DNA was generated by means of an oligonucleotide comprising the degenerate codons $[NN(G/T)]_{10}$ with a self-complementary 3' terminus. This sequence, in forming a hairpin, creates a self-priming replication site which could be used by T4 DNA polymerase to generate the complementary strand. The double-stranded DNA was cleaved at the Sfi I sites at the 5' terminus and hairpin for cloning into the fUSE5 vector described by Scott and Smith, supra.

Other investigators have used other viral capsid proteins for expression of non-viral DNA on the surface of phage particles. The protein pVIII is a major M13 viral capsid protein and interacts with the single stranded DNA of M13 viral particles at its C-terminus. It is 50 amino acids long and exists in approximately 2,700 copies per particle. The N-terminus of the protein is exposed and will tolerate insertions, although large inserts have been reported to disrupt the assembly of pVIII fusion proteins into viral particles (Cesareni, 1992, FEBS Lett. 307:66–70). To minimize the negative effect of pVIII fusion proteins, a phagemid system has been utilized. Bacterial cells carrying the phagemid are infected with helper phage and secrete viral particles that have a mixture of both wild-type and pVIII fusion capsid molecules. pVIII has also served as a site for expressing peptides on the surface of M13 viral particles. Four and six amino acid sequences corresponding to different segments of the *Plasmodium falciparum* major surface antigen have been cloned and expressed in the comparable gene of the filamentous bacteriophage fd (Greenwood et al., 1991, J. Mol. Biol. 220:821–827).

Lenstra, 1992, J. Immunol. Meth. 152:149–157 described construction of a library by a laborious process encompassing annealing oligonucleotides of about 17 or 23 degenerate bases with an 8 nucleotide long palindromic sequence at their 3' ends. This resulted in the expression of random hexa- or octa-peptides as fusion proteins with the β-galactosidase protein in a bacterial expression vector. The DNA was then converted into a double-stranded form with Klenow DNA polymerase, blunt-end ligated into a vector, and then released as Hind III fragments. These fragments were then cloned into an expression vector at the C-terminus of a truncated β-galactosidase to generate $10^7$ recombinants. Colonies were then lysed, blotted on nitrocellulose filters ($10^4$/filter) and screened for immunoreactivity with several different monoclonal antibodies. A number of clones were isolated by repeated rounds of screening and were sequenced.

Cull et al., 1992, Proc. Natl. Acad. Sci. USA 89:1865–1869 described a system in which random peptides were fused to the carboxy terminus of the lac repressor. The fusion proteins contained an intact lac amino terminus (which is responsible for specific binding of the lac repressor to the DNA sequences constituting the lac operator sites). The nucleotide sequences encoding the fusion protein were cloned into a plasmid containing copies of the lac operator site. Thus, when the fusion protein was expressed in bacteria, it became bound to the operator sites of the plasmid encoding it. This provided a physical linkage between the fusion protein and the gene encoding it. When bacteria containing the plasmid were screened with ligands for which it was desired to isolate binding partners, the fusion proteins comprising peptides that specifically bound to the ligand were isolated, carrying along the genes that encoded those fusion proteins.

A comprehensive review of various types of peptide libraries can be found in Gallop et al., 1994, J. Med. Chem. 37:1233–1251.

2.2. LIGANDS USED TO SCREEN PEPTIDE LIBRARIES

Screening of peptide libraries has generally been confined to the use of a restricted number of ligands. Most commonly, the ligand has been an antibody (Parmley and Smith, 1989, Adv. Exp. Med. Biol. 251:215–218; Scott and Smith, 1990, Science 249:386–390). In many cases, the aim of the screening is to identify peptides from the library that mimic the epitopes to which the antibodies are directed. Thus, given an available antibody, peptide libraries are excellent sources for identifying epitopes or epitope-like molecules of that antibody (Yayon et al., 1993, Proc. Natl. Acad. Sci. USA 90:10643–10647).

While previous studies have succeeded in identifying epitopes and epitope-like molecules from peptide libraries, it has not been realized in the prior art that this approach could be extended by using the identified epitopes in a further round of screening of a peptide library to identify antibody-like molecules.

When it has been desired to obtain antibody-like molecules, the prior art has employed peptide libraries that contain naturally occurring antibody sequences. This has probably been due to the fact that specific binding by antibodies is known to depend upon a complex structure involving various complementarity determining regions (CDRs), often from both heavy and light antibody chains. Short peptides would not be expected to mimic such structures and longer peptides were thought to be unsuitable for display in the most commonly used libraries.

McCafferty et al., 1990, Nature 348:552–554 used PCR to amplify immunoglobulin variable (V) region genes and cloned those genes into phage expression vectors. The authors suggested that phage libraries of V, diversity (D), and joining (J) regions could be screened with antigen. The phage that bound to antigen could then be mutated in the antigen-binding loops of the antibody genes and rescreened. The process could be repeated several times, ultimately giving rise to phage which bind the antigen strongly.

Marks et al., 1991, J. Mol. Biol. 222:581–597 also used PCR to amplify immunoglobulin variable (V) region genes and cloned those genes into phage expression vectors.

Kang et al., 1991, Proc. Natl. Acad. Sci. USA 88:4363–4366 created a phagemid vector that could be used to express the V and constant (C) regions of the heavy and light chains of an antibody specific for an antigen. The heavy and light chain V-C regions were engineered to combine in the periplasm to produce an antibody-like molecule with a functional antigen binding site. Infection of cells harboring this phagemid with helper phage resulted in the incorporation of the antibody-like molecule on the surface of phage that carried the phagemid DNA. This allowed for identification and enrichment of these phage by screening with the antigen. It was suggested that the enriched phage could be subject to mutation and further rounds of screening, leading to the isolation of antibody-like molecules that were capable of even stronger binding to the antigen.

Hoogenboom et al., 1991, Nucleic Acids Res. 19:4133–4137 suggested that naive antibody genes might be cloned into phage display libraries. This would be followed by random mutation of the cloned antibody genes to generate high affinity variants.

In the prior art, peptide libraries have been screened with receptors to identify receptor ligand-like peptides, but peptide libraries have not been considered useful for identifying such ligand-binding peptides as those that mimic receptors.

Bass et al., 1990, Proteins: Struct. Func. Genet. 8:309–314 fused human growth hormone (hGH) to the carboxy terminus of the gene III protein of phage fd. This fusion protein was built into a phagemid vector. When cells carrying the phagemid were infected with a helper phage, about 10% of the phage particles produced displayed the fusion protein on their surfaces. These phage particles were enriched by screening with hGH receptor-coated beads. It was suggested that this system could be used to develop mutants of hGH with altered receptor binding characteristics.

Lowman et al., 1991, Biochemistry 30:10832–10838 used an improved version of the system of Bass et al. described above to select for mutant hGH proteins with exceptionally high affinity for the hGH receptor. The authors randomly mutagenized the hGH-pIII fusion proteins at sites near the vicinity of 12 amino acids of hGH that had previously been identified as being important in receptor binding.

Balass et al., 1993, Proc. Natl. Acad. Sci. USA 90:10638–10642 used a phage display library to isolate linear peptides that mimicked a conformationally dependent epitope of the nicotinic acetylcholine receptor. This was done by screening the library with a monoclonal antibody specific for the conformationally dependent epitope. The monoclonal antibody used was thought to be specific to the acetylcholine receptor's binding site for its natural ligand, acetylcholine.

Citation or identification of any reference herein shall not be construed as an admission that such reference is available as prior art to the present invention.

3. SUMMARY OF THE INVENTION

The present invention relates to abtides. As used herein, the term "abtides" refers to peptides that mimic the binding specificity of a larger molecule such as an antibody or receptor. Abtides specifically bind to a ligand of interest, in which the ligand is a specific binding partner of the larger molecule (e.g. antibody or receptor). To identify the abtides of the present invention, peptide libraries are screened in a two-step process. The first screening step uses an antibody (or antigen-binding derivative thereof) or receptor (or ligand-binding derivative thereof) as a first target ligand. This step identifies peptide sequences termed "epitopes" or "mimetopes" which specifically bind the first target ligand. In the case where an antibody or derivative thereof is used as the first target ligand, a mimetope will often resemble, either functionally in terms of its binding capability and/or structurally in terms of its amino acid sequence, the epitope recognized by the antibody used as the first ligand. An epitope or mimetope is then used as a second target ligand in a second screening step to identify a peptide sequence that specifically binds the epitope or mimetope. Such peptides are known as "abtides." Surprisingly, it was found by the current inventor and is demonstrated herein that abtides possess binding specificities strikingly similar to those possessed by the first target ligands (usually antibodies or receptors) described above.

Abtides are useful since they mimic the binding specificities of antibodies or receptors. Thus, they may be used in many instances where antibodies or receptors may be used. The present invention further relates to the use of abtides in the place of antibodies in assays such as the many types of immunoassays known in the art. Abtides may take the place of antibodies in such assays as, for example, enzyme-linked immunosorbent assays (ELISAs) or sandwich immunoassays. The invention also provides abtide compositions for use in therapy and diagnosis. In a specific example, abtides have been discovered and demonstrated to be useful in place of antibodies in enzyme-linked immunosorbent assays and in in vivo localization to prostate carcinoma in a xenograft model.

The use of abtides has many potential advantages over the use of antibodies or receptors: the smaller size of abtides allows their easier production at lower cost, reduced immunogenicity, and may facilitate their in vivo delivery if such is desired; biological reactions and functions mediated by constant domains of antibodies, and cross-linking of antibodies/receptors and resulting biological effects can be avoided if desired.

4. BRIEF DESCRIPTION OF THE DRAWINGS

The present invention may be understood more fully by reference to the following detailed description of the invention, examples of specific embodiments of the invention and the appended figures in which.

Figure 1:
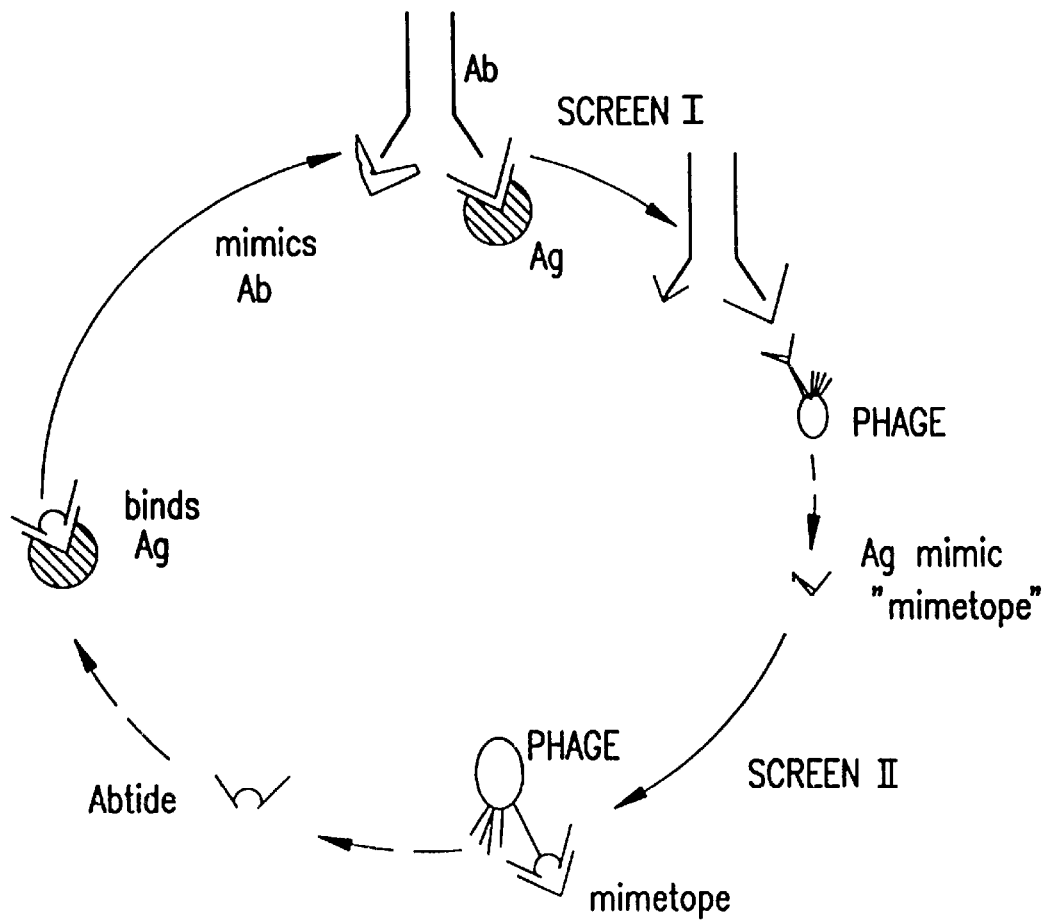
FIG. 1 shows in schematic diagram a general method for identifying an abtide by a two-step screening process. See Section 5.3 for a discussion of this method.

FIG. 3 shows similarities in the amino acid sequences of the CDR2L and CDR3L regions of monoclonal antibody 7E11-C5 and the 7E11-C5 abtides of Table 2. The number of amino acids in the abtides that are similar to the CDRs is indicated in parentheses, along with the percent homology. Dashes indicate gaps which have been added to improve the homology. In the case of clones 13 and 16, the homology with CDR2L was greatest if the sequence of CDR2L was reversed. The sequence shown for clone 14 is SEQ ID NO: 1; the sequence shown for clone 17 is SEQ ID NO: 2; The sequence shown for clone 15 is SEQ ID NO: 3; the sequence shown for clone 13 is SEQ ID NO: 4; the sequence shown for clone 16 is SEQ ID NO: 5; the sequence shown for CDR3L is SEQ ID NO: 6; the sequence shown for CDR2L is SEQ ID NO: 7;the sequence shown for CDR2L(rev) is SEQ ID NO: 8.

Figure 4:
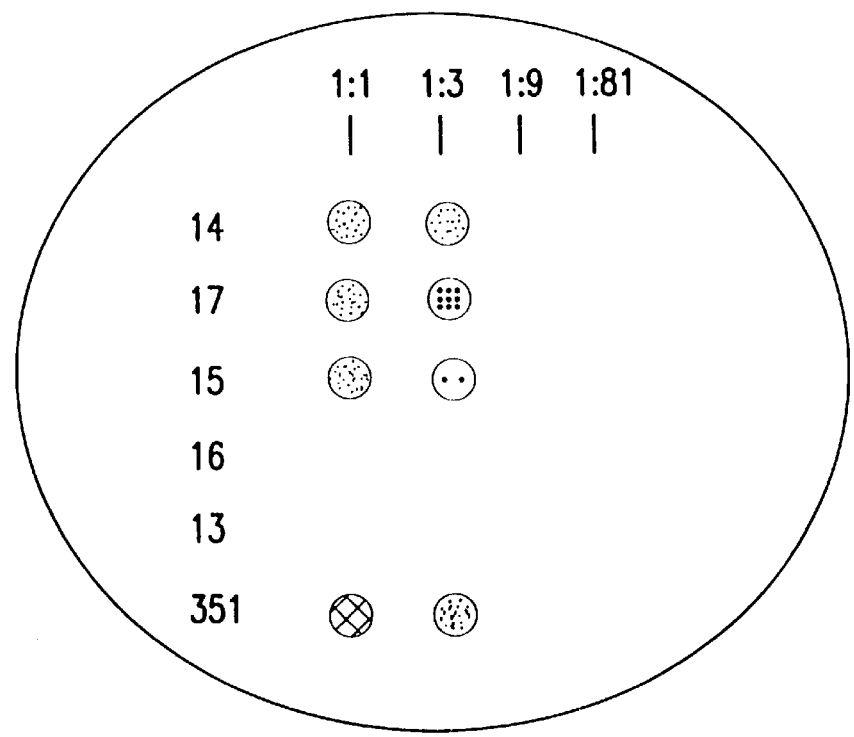

FIG. 4 shows binding of abtides to the 7E11–9.5 mimetope peptide in a dot blot assay as described in Section 6.1.2.1. Numbers along the left side of the figure refer to the 7E11-C5 abtide that was spotted in the indicated position. The number 351 refers to the monoclonal antibody 7E11-C5, used as a positive control. The numbers along the top of the figure refer to the various dilutions of the abtide or the monoclonal antibody that were used.

Figure 5:
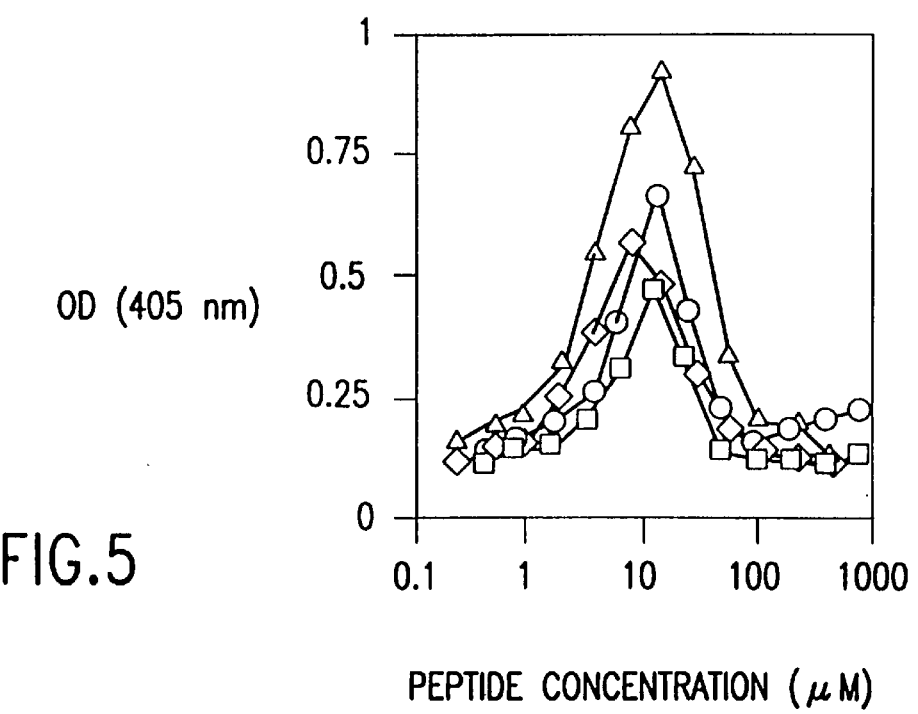

FIG. 5 shows the binding of biotinylated mimetopes to immobilized abtides. □ represents binding of mimetope peptide Biotin-LYANPGMYSRLHSPA-NH$_2$ (SEQ ID NO: 20) to 7E11-C5 abtide clone 14; ○ represents binding of mimetope peptide Biotin-LYANPGMYSRLHSPA-NH$_2$ (SEQ ID NO: 20) to 7E11-C5 abtide clone 17; ◊ represents binding of mimetope peptide Biotin-GMYSRLH-NH$_2$ (a portional SEQ ID NO: 20) to 7E11-C5 abtide clone 14; Δ represents binding of mimetope peptide Biotin-GMYSRLH-NH$_2$ (a portional SEQ ID NO: 20) to 7E11-C5 abtide clone 17. See Section 6.1.2.2 for details.

Figure 6:
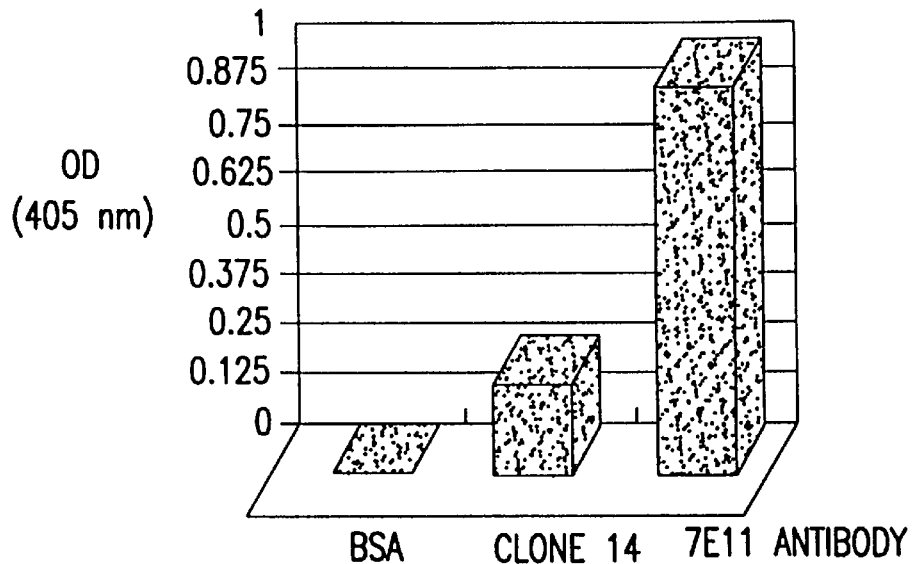

FIG. 6 shows the capture of an antigen from a lysate of LNCaP tumor cells by the monoclonal antibody 7E11-C5 and the 7E11-C5 abtide clone 14. See Section 6.1.3 for details.

Figure 7:
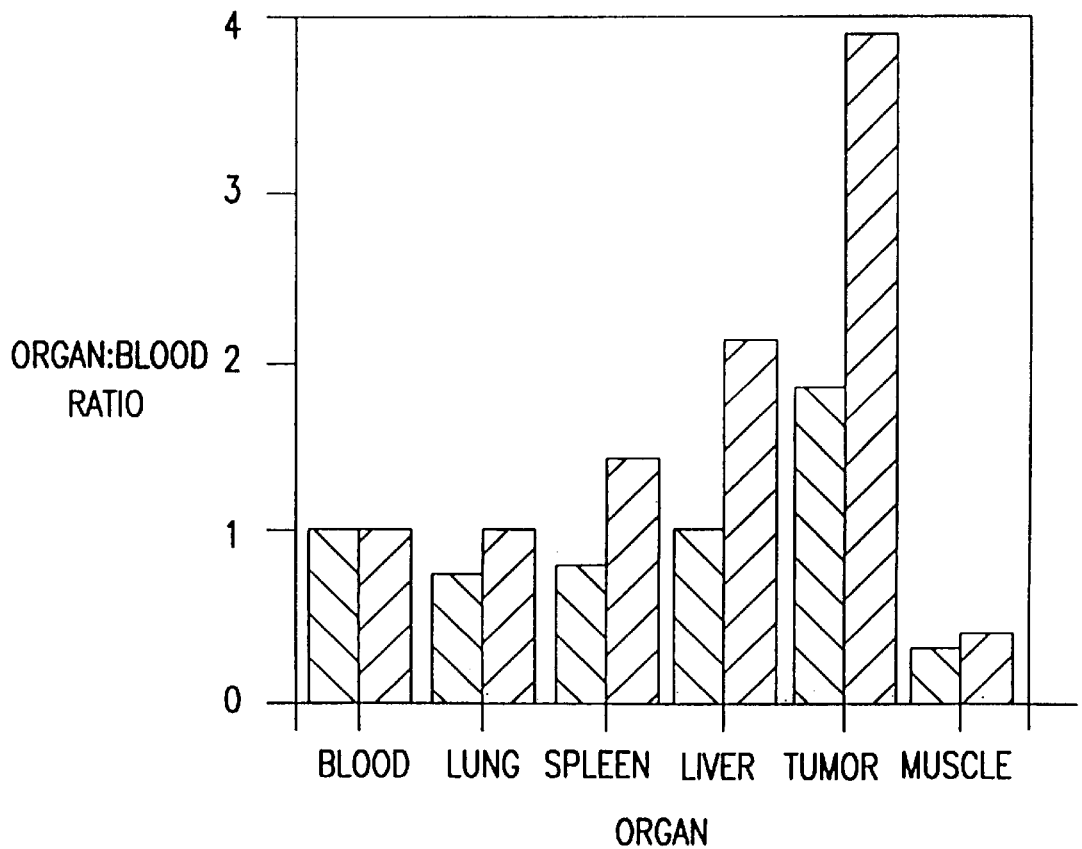

FIG. 7 shows the biodistribution of abtide clone 14-DPTA-$^{111}$In in SCID mice bearing human prostate carcinoma LNCaP xenograft tumors 2 hours ▢, bar on the left for each pair of bars) or 4 hours ▨, bar on the right for each pair of bars) post-injection of 2 μg of peptide, specific activity 32 μCi/μg. See Section 6.1.4 for details.

Figure 8:
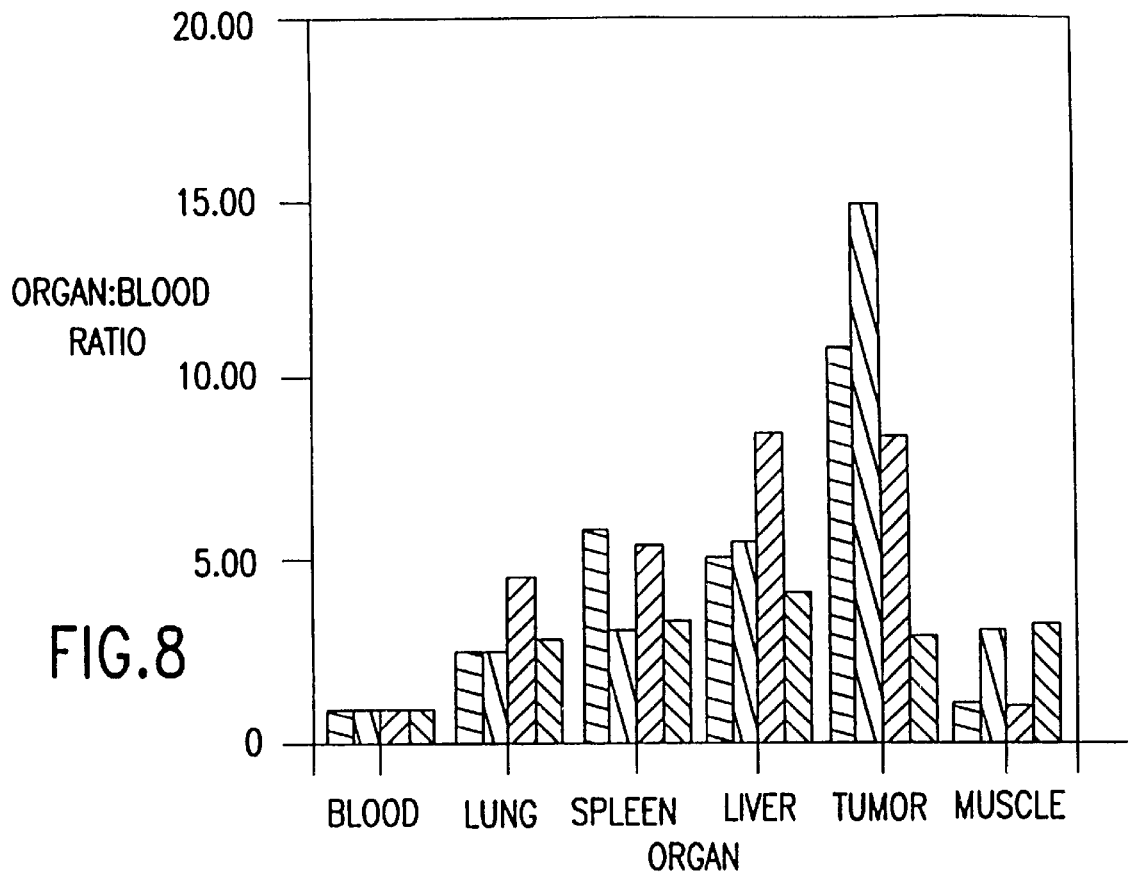

FIG. 8 shows the biodistribution of abtide clone 17-DPTA-[111]-In in four SCID mice bearing human prostate LNCaP carcinoma xenograft tumors 2 hours ▢, leftmost bar for each group of four bars, mouse 1; ▢, second bar from left for each group of four bars, mouse 6) or five hours ▢, third bar from left for each group of four bars, mouse 2; ▨, rightmost bar for each group of four bars, mouse 4) post-injection of 0.02 μg of peptide, specific activity 2.4 μCi/ng. See Section 6.1.4 for details.

Figure 9:
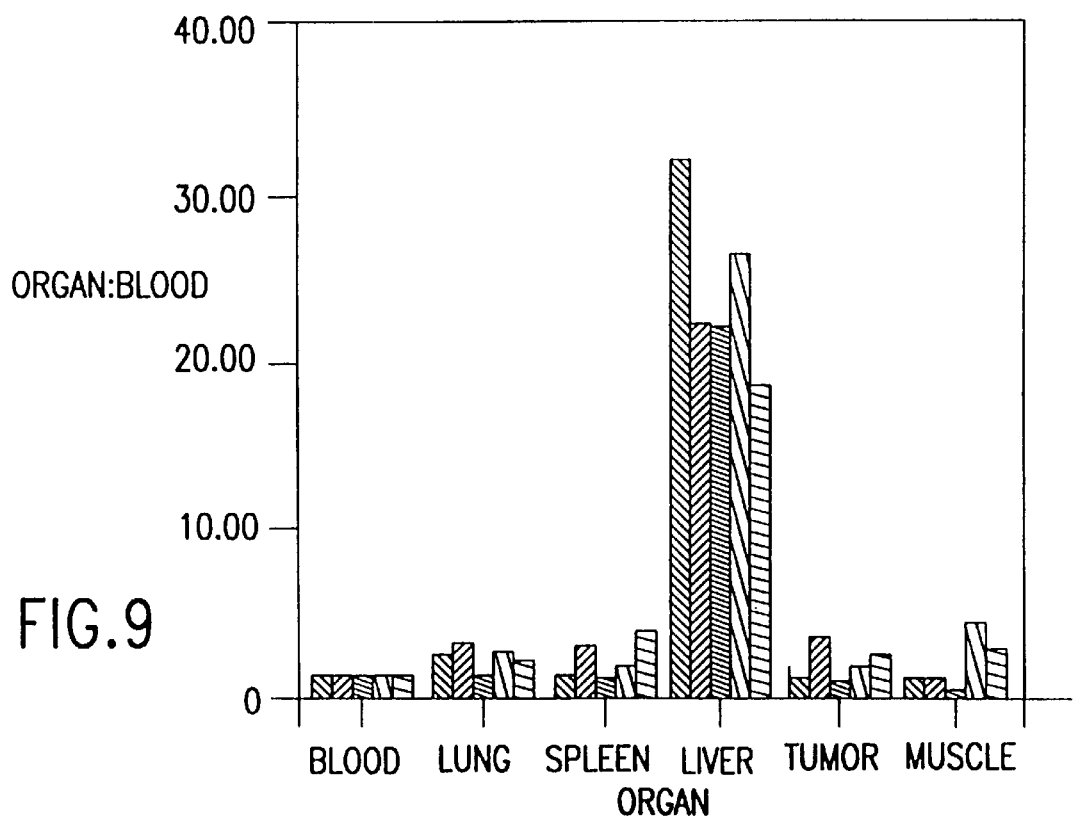

FIG. 9 shows the biodistribution of [111]-In labeled control irrelevant peptide in SCID mice bearing human prostate carcinoma LNCaP xenograft tumors 2 hours ▢, leftmost bar for each group of five bars; ▨, second bar from left for each group of five bars) or 5 hours ▨, third bar from left for each group of five bars; ▨, fourth bar from left for each group of five bars; ▢, rightmost bar for each group of five bars) post-injection of 1.5 μg of peptide, specific activity 30 μCi/μg. See Section 6.1.4 for details.

FIG. 10 schematically illustrates the construction of the R26 TSAR library. The R26 expression library was constructed essentially as described for the TSAR-9 library that is described in PCT publication WO 94/18318, dated Aug. 18, 1994, except for the modifications depicted in FIG. 10. The oligonucleotide assembly process depicted in FIG. 10 results in expression of peptides with the following amino acid sequence:
S(S/R)X$_{12}$πAδX$_{12}$SR (SEQ ID NO: 25), where π=S, P, T or A; and δ=V, A, D, E OR G ctgtgcctcgagB(NNB)$_{12}$Nccgcgg is SEQ ID NO: 87; ctgtgctctaga(VNN)$_{12}$VNccgcgg is SEQ ID NO: 88; tcgagB(NNB)$_{12}$Nccgcgg is SEQ ID NO: 89; ctagt(VNN)$_{12}$VNccgcgg is SEQ ID NO: 90; SHSS(S/R)X$_{12}$πAδX$_{12}$SRPSRT is SEQ ID NO: 91.

FIG. 11 schematically illustrates the construction of the D38 TSAR library. The D38 expression library was constructed essentially as described for the TSAR-9 library that is described in PCT publication WO 94/18318, dated Aug. 18, 1994, except for the modifications depicted in FIG. 11. GTGTGTCTCGAGN(NNB)$_{20}$NACGCCAN is SEQ ID NO: 92; GTTGTGTCTAGA(VNN)$_{15}$VNTGGCGTN is SEQ ID NO: 93; TCGAGN(NNB)$_{20}$NACGCCAN is SEQ ID NO: 94; CTAGA(VNN)$_{15}$VNTGGCGTN is SEQ ID NO: 95; HSS(S/R)X$_{20}$(Y/H/N/D)A(I/M/T/N/K/S/R)X$_{15}$SR is SEQ ID NO: 96.

FIG. 12 schematically illustrates the construction of the DC43 TSAR library. The DC43 expression library was constructed essentially as described for the TSAR-9 library that is described in PCT publication WO 94/18318, dated Aug. 18, 1994, except for the modifications depicted in FIG. 12. GTGTGTCTCGAGN(NNB)$_{20}$GGTTGTGGT is SEQ ID NO: 97; GTTGTGTCTAGA(VNN)$_{20}$ACCACAACC is SEQ ID NO: 98; TCGAGN(NNB)$_{20}$GGTTGTGGT is SEQ ID NO: 99; CTAGA(VNN)$_{20}$ACCACAACC is SEQ ID NO: 100; HSS(S/R)X$_{20}$GCGX$_{20}$SR is SEQ ID NO: 101.

FIG. 13 schematically illustrates the oligonucleotides used to construct the polymorphic epithelial mucin (PEM) abtide saturation mutagenesis TSAR library (See Section 6.2.2). GAPVWRGNPRWRGPGGFKWPGCGNGPM-CNTFTPARGGSRNNGP is SEQ ID NO: 51; ggsgcsccsgt-stgsagsggsaasccscgstg-sagsggsccsggsggsttsaastgsccsGGCTGCGGG is SEQ ID NO: 102; sggsccsttsttscgsgasccsccscgs-gcsggsgtsaasgtsttscasatsggsccsttCCCGCAGCC is SEQ ID NO: 103.

5. DETAILED DESCRIPTION OF THE INVENTION

The present invention relates generally to abtides. As used herein, the term "abtides" refers to peptides that mimic the binding specificity of a larger molecule such as an antibody or receptor. Abtides specifically bind to a ligand of interest, in which the ligand is a specific binding partner of the mimicked larger molecule (e.g. antibody or receptor). To identify the abtides of the present invention, peptide libraries are typically screened in a two-step process (see FIG. 1). The first screening step uses an antibody (or antigen-binding derivative thereof) or receptor (or ligand-binding derivative thereof) as a first target ligand. This step identifies peptide sequences termed "epitopes" or "mimetopes" which specifically bind the first target ligand. If the first screening step uses an antibody and the peptide identified contains the amino acid sequence of the natural antigen that is responsible for the specific binding of the antigen to the antibody, then the identified peptide is said to be an epitope; if the identified peptide does not contain the sequence of the natural antigen, then the identified peptide is said to be a mimetope. In the case where an antibody or derivative thereof is used as the first target ligand, a mimetope will often resemble, either functionally in terms of its binding capability and/or structurally in terms of its amino acid sequence, the epitope recognized by the antibody used as the first ligand.

A mimetope is then used as a second target ligand in a second screening step to identify a peptide sequence that specifically binds the epitope or mimetope. Such peptides are known as "abtides." Abtides possess binding specificities similar to those possessed by the first target ligands (usually antibodies or receptors) described above.

In a specific embodiment, the antibody or derivative thereof used in the first screening step recognizes a tumor antigen, preferably a human tumor antigen, most preferably of a malignant tumor.

The present invention provides a method to successfully screen against very small peptide or protein targets, e.g. 5 to 40 amino acids, preferably 10 to 20 amino acids. To date, screening against such targets has not been successful. The methods of the present invention increase the likelihood that the abtide obtained will bind its target in a complex or structurally dependent fashion.

Abtides are useful since they mimic the binding specificities of antibodies or receptors. Thus, they may be used in many instances where antibodies or receptors may be used. The present invention further relates to the use of abtides in the place of antibodies in assays such as the many types of immunoassays known in the art. Abtides may take the place of antibodies in such assays as, for example, enzyme-linked immunosorbent assays (ELISAs) or sandwich immunoassays. The invention also provides abtide compositions for use in therapy and diagnosis of disease. In a specific example, abtides have been produced and demonstrated to be useful in place of antibodies in enzyme-linked immunosorbent assays and in in vivo localization to prostate carcinoma in xenograft models.

The use of abtides has many potential advantages over the use of antibodies or receptors: the smaller size of abtides allows their easier production at lower cost, reduced immunogenicity, and facilitates their in vivo delivery if such is desired; biological reactions and functions mediated by constant domains of antibodies, and cross-linking of antibodies/receptors and resulting biological effects can be avoided if desired.

5.1. PEPTIDE LIBRARIES FOR USE IN IDENTIFYING ABTIDES

The abtides of the present invention can be identified from a chemically synthesized peptide library or a biologically expressed peptide library. If a biological peptide expression library is used, the nucleic acid which encodes the peptide which binds to the ligand of choice can be recovered, and then sequenced to determine its nucleotide sequence and hence deduce the amino acid sequence that mediates binding. Alternatively, the amino acid sequence of an appropriate binding domain can be determined by direct determination of the amino acid sequence of a peptide selected from a peptide library containing chemically synthesized peptides. In a less preferred aspect, direct amino acid sequencing of a binding peptide selected from a biological peptide expression library can also be performed.

In a preferred embodiment of the present invention, the abtides are advantageously identified from random peptide libraries. Typically, random peptide libraries will be encoded by synthetic oligonucleotides with a plurality of variant nucleotide positions having the potential to encode all 20 naturally occurring amino acids. The sequence of amino acids encoded by the variant nucleotides is unpredictable and substantially random. The terms "unpredicted", "unpredictable" and "substantially random" are used interchangeably with respect to the amino acids encoded and are intended to mean that the variant nucleotides at any given position are such that it cannot be predicted which of the 20 naturally occurring amino acids will appear at that position. These variant nucleotides are the product of random chemical synthesis. The biological random peptide libraries envisioned for use include those in which a bias has been introduced into the random sequence, e.g., to disfavor stop codon usage.

5.1.1. CHEMICALLY SYNTHESIZED PEPTIDE LIBRARIES

The peptide libraries used in the present invention may be libraries that are chemically synthesized in vitro. Examples of such libraries are given in Fodor et al., 1991, Science 251:767–773, which describes the synthesis of a known array of short peptides on an individual microscopic slide; Houghten et al., 1991, Nature 354:84–86, which describes mixtures of free hexapeptides in which the first and second residues in each peptide were individually and specifically defined. Lam et al., 1991, Nature 354:82–84, which describes a split synthesis scheme; Medynski, 1994, Bio/Technology 12:709–710, describes split synthesis and T-bag synthesis methods as well. See also Gallop et al., 1994, J. Medicinal Chemistry 37:1233–1251.

PCT publication WO 91/05058, dated Apr. 18, 1991, is directed to random libraries containing semi-random nucleotide sequences. The semi-random nucleotide sequences are transcribed in vitro under conditions such that polysomes are produced. The polysomes are screened for binding to a substance of interest. Those polysomes that bind to the substance of interest are recovered. The RNA from those polysomes is used to construct cDNA, which is expressed to produce polypeptides.

Screening to identify peptides which bind to a ligand of choice can be carried out by methods well known in the art.

In a specific embodiment, the total number of unpredictable amino acids in the peptides of the chemical library used for screening is greater than or equal to 5 and less than or equal to 25; in other embodiments the total is in the range of 5–15 or 5–10 amino acids, preferably contiguous amino acids.

While a binding domain can be identified from chemically synthesized peptide libraries, such a domain would be small (i.e. less than 10 amino acids, and most probably 5–6 amino acids, in length). Therefore, use of a chemically synthesized peptide library is less preferred for the second screening step involved in isolating abtides than is use in the second screening step of biological peptide libraries containing unpredictable sequences of greater length, described below.

5.1.2. BIOLOGICAL PEPTIDE LIBRARIES

In another embodiment, biological peptide libraries are used to identify abtides. Many suitable biological peptide libraries are known in the art and can be used.

According to this second approach, involving recombinant DNA techniques, peptides have been expressed in biological systems as either soluble fusion proteins or viral capsid fusion proteins.

A number of peptide libraries according to this approach have used the M13 phage. Although the N-terminus of the viral capsid protein, protein III (pIII), has been shown to be necessary for viral infection, the extreme N-terminus of the mature protein does tolerate alterations such as insertions. Accordingly, various peptide libraries, in which the diverse peptides are expressed as pIII fusion proteins, are known in the art; these libraries can be used to identify abtides. Examples of such libraries are described below.

Scott and Smith, 1990, Science 249:386–390 describe construction and expression of an "epitope library" of hexapeptides on the surface of M13. The library was made by inserting a 33 base pair Bgl I digested oligonucleotide sequence into an Sfi I digested phage fd-tet, i.e., fUSE5 RF. The 33 base pair fragment contains a random or "degenerate" coding sequence $(NNK)_6$ where N represents G, A, T or C and K represents G or T. The authors stated that the library consisted of $2 \times 10^8$ recombinants expressing $4 \times 10^7$ different hexapeptides; theoretically, this library expressed 69% of the $6.4 \times 10^7$ possible peptides ($20^6$). Cwirla et al., 1990, Proc. Natl. Acad. Sci. USA 87: 6378–6382 also described a somewhat similar library of hexapeptides expressed as pIII gene fusions of M13 fd phage. PCT publication WO 91/19818 dated Dec. 26, 1991 by Dower and Cwirla describes a similar library of pentameric to octameric random amino acid sequences.

Devlin et al., 1990, Science, 249:404–406, describes a peptide library of about 15 residues generated using an (NNS) coding scheme for oligonucleotide synthesis in which S is G or C.

Christian and colleagues have described a phage display library, expressing decapeptides (Christian et al., 1992, J. Mol. Biol. 227:711–718). The starting DNA was generated by means of an oligonucleotide comprising the degenerate codons [NN(G/T)]$_{10}$ with a self-complementary 3' terminus. This sequence, in forming a hairpin, creates a self-priming replication site which could be used by T4 DNA polymerase to generate the complementary strand. The double-stranded DNA was cleaved at the SfiI sites at the 5° terminus and hairpin for cloning into the fUSES vector described by Scott and Smith, supra.

Lenstra, 1992, J. Immunol. Meth. 152:149–157 describes construction of a library by a laborious process encompassing annealing oligonucleotides of about 17 or 23 degenerate bases with an 8 nucleotide long palindromic sequence at their 3' ends. This resulted in the expression of random hexa- or octa-peptides as fusion proteins with the β-galactosidase protein in a bacterial expression vector. The DNA was then converted into a double-stranded form with Klenow DNA polymerase, blunt-end ligated into a vector, and then released as Hind III fragments. These fragments were then cloned into an expression vector at the sequence encoding the C-terminus of a truncated β-galactosidase to generate $10^7$ recombinants.

Other biological peptide libraries which can be used include those described in U.S. Pat. No. 5,270,170 dated Dec. 14, 1993 and PCT Publication No. WO 91/19818 dated Dec. 26, 1991. Also suitable are those in U.S. Pat. No. 5,096,815, U.S. Pat. No. 5,198,346, and U.S. Pat. No. 5,223,409, all to Ladner et al.

The biological peptide libraries discussed above are meant to be illustrative and not limiting. It will be recognized by one of skill in the art that many other biological peptide libraries disclosed in various publications may be suitable for use in the practice of the present invention.

The protein pVIII is a major M13 viral capsid protein, which can also serve as a site for expressing peptides on the surface of M13 viral particles, in the construction of random peptide libraries.

While it would be understood by one skilled in the art that as few as 5 amino acids can constitute a binding domain, the average functional domain within a natural protein is considered to be about 40 amino acids. Thus, the random peptide libraries from which the abtides of the present invention are preferably identified encode peptides having in the range of 5 to 200 total variant amino acids. Although it is contemplated that biologically expressed random peptide libraries displaying short random inserts (i.e. less than 20 amino acids in length) could be used to identify abtides of the invention, the most preferred biologically expressed random peptide libraries for use in the invention are those in which the displayed peptide has 20 or greater unpredictable amino acids i.e. preferably in the range of 20 to 100, and most preferably 20 to 50 amino acids, as exemplified by the TSAR libraries described in PCT publication WO 91/12328, dated Aug. 22, 1991, and PCT publication WO 94/18318, dated Aug. 18, 1994.

To identify abtides, particularly in the second screening step, the invention preferably uses libraries of greater complexity than are commonly employed in the art. The conventional teaching in the random peptide library art is that the length of inserted oligonucleotides should be kept short, encoding preferably fewer than 15 and most preferably about 6–8 amino acids. However, not only can libraries encoding more than about 20 amino acids be constructed, but such libraries can be advantageously screened to identify peptides having binding specificity for a variety of ligands. Such libraries with longer length inserts are exemplified by the TSAR libraries, described in PCT publication WO 91/12328, dated Aug. 22, 1991, and PCT publication WO 94/18318, dated Aug. 18, 1994.

These PCT publications disclose that the use of libraries composed of longer length oligonucleotides has many advantages.

Libraries composed of longer length oligonucleotides afford the ability to identify peptides in which a short sequence of amino acids is common to or shared by a number of peptides binding a given ligand, i.e., library members having shared binding motifs. The use of longer length libraries also affords the ability to identify peptides which do not have any shared sequences with other peptides but which nevertheless have binding specificity for the same ligand.

When screened by the method of the present invention, libraries having large inserted oligonucleotide sequences provide the opportunity to identify or map binding sites which encompass not only a few contiguous amino acid residues, i.e., simple binding sites, but also those which encompass discontinuous amino acids, i.e., complex binding sites, and may afford the complex binding characteristic of antibodies and receptor-like molecules.

Additionally, the large size of the inserted synthesized oligonucleotides of certain libraries provides the opportunity for the development of secondary and/or tertiary structure in the potential binding peptides and in sequences flanking the actual binding site in the binding domain. Secondary and tertiary structure often significantly affect the ability of a sequence to mediate binding, as well as the strength and specificity of any binding which occurs. Such complex structural effects are not possible when only small length oligonucleotides are used in libraries. It may be that secondary and tertiary structures are especially important in the identification of abtides since abtides mimic the binding of large molecules such as antibodies. It is well known that the antigen binding properties of antibodies depend in most instances upon several different regions of the heavy chain (complementarity determining regions) and upon regions contributed by the light chain as well.

Therefore, it is contemplated that the most preferred binding domains for identifying the abtides of the present invention will be those from biologically expressed random peptide libraries in which the displayed peptide is 20 or greater amino acids in length. Examples of such random peptide libraries are the TSAR libraries, described in in PCT publication WO 91/12328, dated Aug. 22, 1991, and PCT publication WO 94/18318, dated Aug. 18, 1994.

In one embodiment, the library utilized in the present invention is a linear, non-constrained library. As would be understood by one in the art having considered the present disclosure, in another specific embodiment, "constrained", "structured" or "semi-rigid" random peptide libraries could also be used in the present methods to identify abtides. Typically, these libraries express peptides that are substantially random but contain a small percentage of fixed residues within or flanking the random sequences that have the result of conferring structure or some degree of conformational rigidity to the peptide. In a semirigid peptide library, the plurality of synthetic oligonucleotides express peptides that are each able to adopt only one or a small number of different conformations that are constrained by the positioning of codons encoding certain structure conferring amino acids in or flanking the synthesized variant or unpredicted oligonucleotides. Unlike linear, unconstrained libraries in which the plurality of proteins expressed potentially adopt thousands of short-lived different conformations, in a semi-rigid peptide library, the plurality of proteins expressed can adopt only a single or a small number of conformations.

Such libraries are exemplified by the TSAR-13 and TSAR-14 libraries described in PCT publication WO 94/18318, dated Aug. 18, 1994; by a library of random 6 amino acid sequences, each flanked by invariant cysteine residues (O'Neil et al., 1992, Proteins 14:509–515); and by those libraries disclosed in PCT Publication No. WO 94/11496, dated May 26, 1994 (Huse).

In a preferred embodiment, a biological peptide library that is a random peptide "TSAR" library is screened to identify an abtide. TSARs is an acronym for "Totally Synthetic Affinity Reagents" as described in PCT publication WO 91/12328, dated Aug. 22, 1991, and PCT publication WO 94/18318, dated Aug. 18, 1994. TSAR libraries, their construction and use, and specific examples of TSAR libraries, are described in detail in those PCT publications. Nucleic acids encoding TSARs or a TSAR portion which mediates binding to the ligand used for screening can be used to identify the abtides of the present invention.

A TSAR may be a heterofunctional fusion protein, said fusion protein comprising (a) a binding domain encoded by an oligonucleotide comprising unpredictable nucleotides in which the unpredictable nucleotides are arranged in one or more contiguous sequences, wherein the total number of unpredictable nucleotides is greater than or equal to about 60 and less than or equal to about 600, and optionally, (b) an effector domain encoded by an oligonucleotide sequence which is a protein or peptide that enhances expression or detection of the binding domain.

Alternatively, a TSAR may be a heterofunctional fusion protein as described above but in which the contiguous sequences are flanked by invariant residues designed to encode amino acids that confer a desired structure to the binding domain of the expressed heterofunctional fusion protein.

In addition to TSAR libraries, other libraries for use in the present invention may be those wherein the library is a library of recombinant vectors that express a plurality of heterofunctional fusion proteins, said fusion proteins comprising a binding domain encoded by an oligonucleotide comprising unpredictable nucleotides in which the unpredictable nucleotides are arranged in one or more contiguous sequences, wherein the total number of unpredictable nucleotides is greater than or equal to about 15 and less than or equal to about 600.

5.2. ABTIDES

An abtide is typically a peptide that mimics, with respect to binding specificity, and possibly other characteristics (e.g., binding affinity, sequence, etc.) a large molecule such as an antibody or receptor. However, an abtide is generally much smaller than an antibody or receptor. An abtide is generally a peptide of about 5 to 200 amino acids. Preferably, an abtide is a peptide of about 10 to 100 amino acids. Most preferably, an abtide is a peptide of about 20 to 50 amino acids. In addition to the amino acid sequences which are responsible for the abtide's specific binding properties, an abtide may be linked to additional amino acid sequences or additional non-amino acid sequences. Such additional sequences may aid in the identification or isolation of the abtide. Or, they may aid in the biodistribution, stability, or diagnostic or therapeutic effectiveness of the abtide when the abtide is used diagnostically or therapeutically.

The abtides may be linked to a variety of non-peptide moieties. Such moieties might include toxins; drugs; polysaccharides; nucleotides; oligonucleotides; labels such as radioactive substances (e.g. $^{111}$In, $^{125}$I, $^{131}$I, $^{99m}$Tc, $^{212}$B, $^{90}$Y, $^{186}$Rh); biotin; fluorescent tags; imaging reagents (e.g. those described in U.S. Pat. No. 4,741,900 and U.S. Pat. No. 5,326,856); hydrocarbon linkers (e.g., an alkyl group or derivative thereof) conjugated to a moiety providing for attachment to a solid substratum, or to a moiety providing for easy separation (e.g., a hapten recognized by an antibody bound to a magnetic bead), etc. Linkage of the peptide to the non-peptide moiety may be by any of several well-known methods in the art.

In addition, in an embodiment in which an abtide has a free amino- or carboxy- terminus, such termini can be modified by known methods, e.g., to provide greater resistance to degradation, greater cell permeability, greater solubility, etc., e.g., by acetylation, biotinylation, fatty acylation, etc. at the amino-terminus; amidation at the carboxy-terminus; or the abtide can be stabilized by inclusion of D amino acids, nonnatural amino acids or glycosyl amino acids, etc.

The abtides of the invention are preferably made by commonly known methods of chemical synthesis, e.g., as described by way of example in Section 5.6 and its subsections.

Alternatively, abtides (or portions thereof) can be obtained by recombinant expression of a nucleic acid encoding the desired abtide in an appropriate host, by well-known methods.

Occasionally, it may happen that not all of the amino acids in the identified peptide will be necessary for the binding function of an abtide. Where it is desired to decrease the size of the abtide, methods can be used to identify portions of the determined synthetic amino acid or nucleotide sequences which respectively mediate binding, or encode the sequences which mediate binding, as described in Section 5.4 below.

5.3. SCREENING OF PEPTIDE LIBRARIES TO IDENTIFY ABTIDES

The process of identifying abtides from a peptide library comprises two distinct screening steps. The first step is designed to identify epitopes or ligands with binding specificity for the larger molecule of interest, e.g. antigen mimics, receptor-ligand mimics, and the like. In that first step, a peptide library is screened with a ligand that possesses a specific, often complex, binding site of interest. Those peptides in the library that are specific binding partners of the ligand bind to the ligand and are readily recoverable because of this specific binding. An example of a ligand suitable for use in this first screening step would be an antibody, inherently possessing an antigen binding site, or an antigen-binding derivative thereof. Another example would be a receptor e.g. the epidermal growth factor receptor or the platelet derived growth factor receptor. These particular receptors possess specific binding sites for epidermal growth factor and platelet derived growth factor, respectively. Other receptors are known in the art and are also potential ligands, for example, the estrogen receptor, the various acetylcholine receptors, the human growth hormone receptor, etc.

Molecules comprising those peptide sequences in the library that are identified by the first screening step will be referred to herein as epitopes or mimetopes. For example, in the case where the first ligand is an antibody, the peptides in the library that are identified as specific binding partners of the antibody would be known as antigen epitopes or mimetopes.

The peptides that are isolated in the first screening step are then preferably analyzed, as, for example, by DNA sequencing of the binding domain of the phage that encode the peptides if the library used was a phage library. The DNA sequence of the binding domain encodes the amino acid sequence of the epitope or mimetope peptide. Due to the known relationship between DNA sequences and their encoded amino acid sequences, obtaining the DNA sequence of the epitope or mimetope allows the determination of the amino acid sequence of the epitope or mimetope. Alternatively, if the library used was a chemical library, direct amino acid sequencing of the peptide epitope or mimetope can be carried out by well known methods in the art.

In a specific embodiment, sequences of different peptide mimetopes identified in the first screening step can be compared to determine a consensus mimetope sequence.

Once the amino acid sequence of the epitope or mimetope is known (or a portion thereof, which mediates binding), a molecule, preferably a peptide, is produced comprising that amino acid sequence which mediates binding. This peptide may be synthesized chemically, or, alternatively, may be produced by methods involving recombinant DNA. This peptide may contain only the amino acids of the epitope or mimetope or, preferably, it may contain additional amino acids or non-amino acid moieties to aid in identifying or recovering the epitope or mimetope peptide and any new peptide binders found in the subsequent screening step discussed below.

In the second screening step, the epitope or mimetope that was identified in the first screening step is used as a ligand for the second screening step. The second screening step identifies peptides with binding specificity for the epitope or mimetope and that surprisingly mimic the binding specificity of the antibody or receptor that was used as ligand in the first screening step. In other words, the second screening step yields peptides with antibody or receptor-like binding activity for antigens or receptor ligands that are known as abtides.

FIG. 1 is a schematic representation of an exemplary two-step screening process used to identify abtides.

In a particular embodiment of the invention, it may be that the epitope to which an antibody specifically binds is known. For example, the monoclonal antibody SM-3 that specifically binds the polymorphic epithelial mucin (PEM) found on human breast carcinoma cells has been shown to be specific for the epitope defined by the amino acid sequence VTSAPDTRPAPGSTAPPAHGVTSAPDTR (SEQ ID NO: 9) (Burchell et al., 1989, Int. J. Cancer 44:691–696). In such cases, the first screening step described above may be dispensed with. A peptide comprising the sequence of the epitope for which the antibody is specific can be synthesized and used in the second screening step described above in order to identify abtides of the antibody.

It may also be that the portion of a "receptor-ligand" (i.e., a ligand which specifically binds to a receptor) to which a receptor specifically binds is known. For example, it has been shown that granulocyte/macrophage colony stimulating factor (GM-CSF) binds to the GM-CSF receptor through amino acids 88–121 (HCPPTPETSCATQTITFESFKENLKDFLLVIPFDC [SEQ ID NO: 22]) of GM-CSF. It should be possible to synthesize a peptide corresponding to the portion of the receptor-ligand that has been shown to be responsible for specific binding to the receptor and to use such a peptide in the second screening step of the methods of the present invention in order to identify an abtide of the receptor.

In an embodiment, a molecule comprises a peptide or a binding portion thereof which binds to a ligand of interest, which peptide is identified by a method comprising: screening a random peptide library with a ligand of interest, said ligand of interest being a peptide having a length of between 5 and 40 amino acids, to identify a peptide that specifically binds to the ligand of interest, in which the ligand of interest is also specifically bound by an antibody or a receptor.

In another embodiment, a molecule comprises a peptide which binds to a substance of interest, which peptide is identified by a method comprising: screening a random peptide library with a ligand, said ligand being a peptide of 36 amino acids or fewer, in which the ligand is an epitope of an antigen that is specifically bound by an antibody or in which the ligand represents the portion of a receptor-ligand that is responsible for the specific binding of the receptor to the receptor-ligand.

As used in the present invention, a ligand is a substance for which it is desired to isolate a specific binding partner from a peptide library. A ligand can function as a lock, i.e., a large polypeptide or protein analogous to a lock into which a smaller specific binding partner fits as a key; or a ligand can function as a key which fits into and specifically binds a larger binding partner or lock. In this invention, an epitope or mimetope is typically a peptide that acts as a key; it is identified by screening a peptide library for peptides that fit into and bind the specific binding site of a larger molecule which acts as a lock, e.g. antibody or receptor. If the larger molecule is an antibody and the peptide identified contains the portion of the amino acid sequence of the natural antigen that is responsible for the specific binding of the antigen to the antibody, then the identified peptide is said to be an epitope; if the identified peptide does not contain the sequence of the natural antigen, then the identified peptide is said to be a mimetope.

In a specific embodiment, a mimetope is identified by screening a peptide library with an antibody or antibody fragment. Mimetopes thus identified functionally mimic the antigen to which the antibody binds in that the mimetopes also specifically bind with the antibody. In some cases, if the antigen is a protein or polypeptide, the mimetopes may share amino acid sequence motifs with the antigen. In another embodiment, a mimetope is identified by screening a peptide library with a receptor or receptor fragment. Mimetopes thus identified functionally mimic the natural ligand of the receptor.

The peptide libraries that are used in the first and second screening steps may be the same or different. In one embodiment, a peptide library containing small random inserts (from about 6 to about 15 amino acids) is used in the first screening step.

In the second screening step, it may be desirable to use a larger peptide library. Such larger libraries preferably express peptides of about 20 to 200 random amino acids. Examples of such larger libraries are the TSAR libraries described in PCT publication WO 91/12328, dated Aug. 22, 1991, and in PCT Publication WO 94/18318, dated Aug. 18, 1994.

Biological or chemically synthesized peptide libraries can be used in either the first or second screenings. The peptide libraries used in the present invention may have a plurality of residues that are random, i.e. residues for which the amino acid occupying that residue cannot be predicted in advance. Such libraries are said to be random peptide libraries.

A preferred method for identifying abtides comprises screening a library of recombinant vectors that express a plurality of heterofunctional fusion proteins, said fusion proteins comprising (a) a binding domain encoded by an oligonucleotide comprising unpredictable nucleotides in which the unpredictable nucleotides are arranged in one or more contiguous sequences, wherein the total number of unpredictable nucleotides is greater than or equal to about 15 and less than or equal to about 600, and optionally, (b) an effector domain encoded by an oligonucleotide sequence which is a protein or peptide that enhances expression or detection of the binding domain. Screening is done by contacting the plurality of heterofunctional fusion proteins with a ligand under conditions conducive to ligand binding and then isolating the fusion proteins which bind to the ligand. The methods of the invention further preferably comprise determining the nucleotide sequence encoding the binding domain of the heterofunctional fusion protein identified to determine the DNA sequence that encodes the binding domain and simultaneously to deduce the amino acid sequence of the mimetope used in the second screen. Nucleotide sequence analysis can be carried out by any method known in the art, including but not limited to the method of Maxam and Gilbert (1980, Meth. Enzymol. 65:499–560), the Sanger dideoxy method (Sanger et al., 1977, Proc. Natl, Acad. Sci. U.S.A. 74:5463), the use of "SEQUENASE™," T7 DNA polymerase (Tabor and Richardson, U.S. Pat. No. 4,795,699; U.S. Biochemical Corp.), or TAQ™ polymerase, or use of an automated DNA sequenator (e.g., Applied Biosystems, Foster City, Calif.).

Alternatively, the libraries used to screen for mimetopes and abtides of the invention have unpredictable nucleotides arranged in one or more contiguous sequences that are flanked by invariant residues designed to encode amino acids that confer a desired structure to the binding domain of the expressed heterofunctional fusion protein.

Once a suitable peptide library has been constructed (or otherwise obtained), the library is screened to identify peptides having binding affinity for a ligand of choice. Screening the libraries can be accomplished by any of a variety of methods known to those of skill in the art. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223, 409, and U.S. Pat. No. 5,198,346, all to Ladner et al.; and Rebar and Pabo, 1993, Science 263:671–673. See also PCT publication WO 94/18318, dated Aug. 18, 1994.

If the libraries are expressed as fusion proteins with a cell surface molecule, then screening is advantageously achieved by contacting the vectors with an immobilized target ligand and harvesting those vectors that bind to said ligand. Such useful screening methods, designated "panning" techniques are described in Fowlkes et al., 1992, BioTechniques 13:422–427. In panning methods useful to screen the libraries, the target ligand can be immobilized on plates, beads, such as magnetic beads, sepharose, etc., or on beads used in columns. In particular embodiments, the immobilized target ligand can be "tagged", e.g., using such as biotin, 2-fluorochrome, e.g. for FACS sorting.

In one embodiment, presented by way of example but not limitation, screening a library of phage expressing random peptides on phage and phagemid vectors can be achieved by using magnetic beads as described in PCT publication WO 94/18318, dated Aug. 18, 1994.

Alternatively, as yet another non-limiting example, screening a library of phage expressing random peptides can be achieved by panning using microtiter plates. In a preferred method for recovering the phage bound to the wells of the microtiter plates, a pH change is used.

By way of another example, the libraries expressing random peptides as a surface protein of either a vector or a host cell, e.g., phage or bacterial cell, can be screened by passing a solution of the library over a column of a ligand immobilized to a solid matrix, such as sepharose, silica, etc., and recovering those phage that bind to the column after extensive washing and elution.

By way of yet another example, weak binding library members can be isolated based on retarded chromatographic properties. According to one mode of this embodiment for screening, fractions are collected as they come off the column, saving the trailing fractions (i.e., those members that are retarded in mobility relative to the peak fraction are saved). These members are then concentrated and passed over the column a second time, again saving the retarded fractions. Through successive rounds of chromatography, it is possible to isolate those that have some affinity, albeit weak, to the immobilized ligand. These library members are retarded in their mobility because of the millions of possible ligand interactions as the member passes down the column. In addition, this methodology selects those members that have modest affinity to the target, and which also have a rapid dissociation time.

If desired, the oligonucleotides encoding the binding domain selected in this manner can be mutagenized, expressed and rechromatographed (or screened by another method) to discover improved binding activity. In particular, saturation mutagenesis can be carried out using synthetic oligonucleotides synthesized from "doped" nucleotide reservoirs. The doping is carried out such that the original peptide sequence is represented only once in $10^6$ unique clones of the mutagenized oligonucleotide. The assembled oligonucleotides are cloned into a parental TSAR vector. Preferably, the vector is m663 (Fowlkes et al., 1992, BioTechniques 13:422–427). m663 is able to make blue plaques when grown in E. coli stain JM101 or DH5αF'. A library of greater than $10^6$ is preferred; however a library of $10^5$ is sufficient to isolate TSAR phage displaying peptide domains with increased selectivity for binding to the target ligand.

According to another alternative method, screening a library of can be achieved using a method comprising an "enrichment" step and a filter lift step as follows.

Random peptides from an expressed library capable of binding to a given ligand ("positives") are initially enriched by one or two cycles of panning or affinity chromatography, as described above. The goal is to enrich the positives to a frequency of about $>1/10^5$. Following enrichment, a filter lift assay is conducted. For example, approximately $1-2\times10^5$ phage, enriched for binders, are added to 500 µl of log phase E. coli and plated on a large LB-agarose plate with 0.7% agarose in broth. The agarose is allowed to solidify, and a nitrocellulose filter (e.g., 0.45µ) is placed on the agarose surface. A series of registration marks is made with a sterile needle to allow re-alignment of the filter and plate following development as described below. Phage plaques are allowed to develop by overnight incubation at 37° C. (the presence of the filter does not inhibit this process). The filter is then removed from the plate with phage from each individual plaque adhered in situ. The filter is then exposed to a solution of BSA or other blocking agent for 1–2 hours to prevent non-specific binding of the ligand (or "probe").

The probe itself is labeled, for example, either by biotinylation (using commercial NHS-biotin) or direct enzyme labeling, e.g., with horse radish peroxidase (HRP) or alkaline phosphatase. Probes labeled in this manner are indefinitely stable and can be re-used several times. The blocked filter is exposed to a solution of probe for several hours to allow the probe to bind in situ to any phage on the filter displaying a peptide with significant affinity to the probe. The filter is then washed to remove unbound probe, and then developed by exposure to enzyme substrate solution (in the case of directly labeled probe) or further exposed to a solution of enzyme-labeled avidin (in the case of biotinylated probe). In a preferred method, an HRP-labeled probe is detected by ECL western blotting methods (Amersham, Arlington Heights, Ill.), which involves using luminol in the presence of phenol to yield enhanced chemiluminescence detectable by brief exposure of film by autoradiography, in which the exposed areas of film correspond to positive plaques on the original plate. Where an enzyme substrate is used, positive phage plaques are identified by localized deposition of colored enzymatic cleavage product on the filter which corresponds to plaques on the original plate. The developed filter or film, as the case may be, is simply realigned with the plate using the registration marks, and the "positive" plaques are cored from the agarose to recover the phage. Because of the high density of plaques on the original plate, it is usually impossible to isolate a single plaque from the plate on the first pass. Accordingly, phage recovered from the initial core are re-plated at low density and the process is repeated to allow isolation of individual plaques and hence single clones of phage.

Successful screening experiments are optimally conducted using 3 rounds of serial screening. The recovered cells are then plated at a low density to yield isolated colonies for individual analysis. The individual colonies are selected and used to inoculate LB culture medium containing ampicillin. After overnight culture at 37° C., the cultures are then spun down by centrifugation. Individual cell aliquots are then retested for binding to the target ligand attached to the beads. Binding to other beads, having attached thereto a non-relevant ligand, can be used as a negative control.

One important aspect of screening the libraries is that of elution. For clarity of explanation, the following is discussed in terms of TSAR expression by phage; however, it is readily understood that such discussion is applicable to any system where the random peptide is expressed on a surface fusion molecule. It is conceivable that the conditions that disrupt the peptide-target interactions during recovery of the phage are specific for every given peptide sequence from a plurality of proteins expressed on phage. For example, certain interactions may be disrupted by acid pH's but not by basic pH's, and vice versa. Thus, it may be desirable to test a variety of elution conditions (including but not limited to pH 2–3, pH 12–13, excess target in competition, detergents, mild protein denaturants, urea, varying temperature, light, presence or absence of metal ions, chelators, etc.) and compare the primary structures of the TSAR proteins expressed on the phage recovered for each set of conditions to determine the appropriate elution conditions for each ligand/TSAR combination. Some of these elution conditions may be incompatible with phage infection because they are bactericidal and will need to be removed by dialysis (i.e., dialysis bag, Centricon/Amicon microconcentrators). The ability of different expressed proteins to be eluted under different conditions may not only be due to the denaturation of the specific peptide region involved in binding to the target but also may be due to conformational changes in the flanking regions. These flanking sequences may also be denatured in combination with the actual binding sequence; these flanking regions may also change their secondary or tertiary structure in response to exposure to the elution conditions (i.e., pH 2–3, pH 12–13, excess target in competition, detergents, mild protein denaturants, urea, heat, cold, light, metal ions, chelators, etc.) which in turn leads to the conformational deformation of the peptide responsible for binding to the target.

According to another alternative method in which the TSARs contain a linker region between the binding domain and the effector domain, particular TSAR libraries can be prepared and screened by: (1) engineering a vector, preferably a phage vector, so that a DNA sequence encodes a segment of Factor Xa (or Factor Xa protease cleavable peptide) and is present adjacent to the gene encoding the effector domain, e.g., the pIII coat protein gene; (2) construct and assemble the double stranded synthetic oligonucleotides as described above and insert into the engineered vector; (3) express the plurality of vectors in a suitable host to form a library of vectors; (4) screen for binding to an immobilized ligand; (5) wash away excess phage; and (6) treat the immobilized phage with Factor Xa protease. The particle will be uncoupled from the peptide-ligand complex and can then be used to infect bacteria to regenerate the particle with its full-length pIII molecule for additional rounds of screening. This alternative embodiment advantageously allows the use of universally effective elution conditions and thus allows identification of phage expressing TSARs that otherwise might not be recovered using other known methods for elution. To illustrate, using this embodiment, exceptionally tight binding TSARs could be recovered. If desired, the oligonucleotides encoding the binding domain selected in this manner can be mutagenized, expressed and rechromatographed (or screened by another method) to discover improved binding activity. In particular, saturation mutagenesis can be carried out using synthetic oligonucleotides synthesized from "doped" nucleotide reservoirs. The doping is carried out such that the original peptide sequence is represented only once in $10^6$ unique clones of the mutagenized oligonucleotide. The assembled oligonucleotides are cloned into a parental TSAR vector. Preferably, the vector is m663 (Fowlkes et al., 1992, BioTechniques 13:422–427). m663 is able to make blue plaques when grown in E. coli stain JM101 or DH5αF'. A library of greater than $10^6$ is preferred; however a library of $10^5$ is sufficient to isolate TSAR phage displaying peptide domains with increased selectivity for binding to the target ligand.

For the examples in Section 6 herein, a TSAR library is utilized; however, to those skilled in the art, it will be apparent that other peptide libraries may be used. An example of a TSAR library is the TSAR-9 library disclosed in Kay et al., 1993, Gene 128:59–65. TSAR-9 constructs display a peptide of about 38 amino acids in length having 36 totally random positions.

5.3.1. ANTIBODIES AND DERIVATIVES THEREOF FOR USE IN SCREENING

Antibodies can be produced which recognize an antigen of interest. Such antibodies can be polyclonal or monoclonal. Such antibodies may be used as ligands in the first screening step of the present invention.

Various procedures known in the art may be used for the production of polyclonal antibodies to an antigen of interest. For the production of antibody, various host animals can be immunized by injection with an antigen of interest or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

A monoclonal antibody to an antigen of interest can be prepared by using any technique which provides for the production of antibody molecules by continuous cell lines in culture. These include but are not limited to the hybridoma technique originally described by Kohler and Milstein (1975, Nature 256:495–497), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77–96).

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

A molecular clone of an antibody to an antigen of interest can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype or antigen binding region of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the 2 Fab or Fab fragments which can be generated by treating the antibody molecule with papain and a reducing agent.

5.4. IDENTIFICATION OF SYNTHETIC SEQUENCES WHICH MEDIATE BINDING

When a peptide from a peptide library has been identified as an abtide or mimetope for a particular target ligand of interest according to the method of the invention (in either the first or second screening step), it may be useful to determine what region(s) of the expressed peptide sequence is (are) responsible for binding to the target ligand. Such analysis can be conducted at two different levels, i.e., the nucleotide sequence and amino acid sequence levels.

By molecular biological techniques it is possible to verify and further analyze a ligand binding peptide at the level of the oligonucleotides. First, the inserted oligonucleotides can be cleaved using appropriate restriction enzymes and religated into the original expression vector and the expression product of such vector screened for ligand binding to identify the oligonucleotides that encode the binding region of the abtide or mimetope. Second, the oligonucleotides can be transferred into another vector, e.g., from phage to phagemid. The newly expressed fusion proteins should acquire the same binding activity if the domain is necessary and sufficient for binding to the ligand. This last approach also assesses whether or not flanking amino acid residues encoded by the original vector influence peptide binding in any fashion. Third, the oligonucleotides can be synthesized, based on the nucleotide sequence determined for the phage in the library that encodes the binding peptide, amplified by cloning or PCR amplification using internal and flanking primers, cleaved into two pieces and cloned as two half-binding domain fragments. In the foregoing manner, the inserted oligonucleotides are subdivided into two equal halves. If the peptide domain important for binding is small, then one recombinant clone would demonstrate binding and the other would not. If neither have binding, then either both are important or the essential portion of the domain spans the middle (which can be tested by expressing just the central region).

Alternatively, by synthesizing peptides corresponding to the deduced sequence of the abtide or mimetope, the binding domains can be analyzed. First, the entire peptide should be synthesized and assessed for binding to the target ligand to verify that the peptide is necessary and sufficient for binding. Second, short peptide fragments, for example, overlapping 10-mers, can be synthesized, based on the amino acid sequence of the random peptide binding domain, and tested to identify those binding the ligand.

In addition, in certain instances, linear motifs (consensus motifs) may become apparent after comparing the primary structures of different binding peptides from the library having binding affinity for a target ligand. The contribution of these motifs to binding can be verified with synthesized peptides in competition experiments (i.e., determine the concentration of peptide capable of inhibiting 50% of the binding of the phage to its target; $IC_{50}$). Conversely, the motif or any region suspected to be important for binding can be removed from or mutated within the DNA encoding the random peptide insert and the altered displayed peptide can be retested for binding.

Furthermore, once the binding domain of a peptide has been identified, the binding characteristics of that peptide can be modified by varying the binding domain sequence to produce a related family of peptides with differing properties for a specific ligand.

Moreover, in a method of directed evolution, the identified peptides can be improved by additional rounds of random mutagenesis, selection, and amplification of the nucleotide sequences encoding the binding domains. Mutagenesis can be accomplished by creating and cloning a new set of oligonucleotides that differ slightly from the parent sequence, e.g., by 1–10%. Selection and amplification are achieved as described above. By way of example, to verify that the isolated peptides have improved binding characteristics, mutants and the parent phage, differing in their lacZ expression, can be processed together during the screening experiments. Alteration of the original blue-white color ratios during the course of the screening experiment will serve as a visual means to assess the successful selection of enhanced binders. This process can go through numerous cycles.

5.5. USES OF ABTIDES

5.5.1. ASSAYS USING ABTIDES

The abtides of the present invention possess binding specificities that are similar to those of the ligands (e.g. antibodies, receptors) that are used in the first screening step of the process by which the abtides are identified. Consequently, the abtides may be used in many of the same instances where the ligand of the first screening step might be used. For example, if the ligand used in the first screening step is an antibody, the abtide that is identified after the second screening step will bind specifically to the same antigen to which the antibody specifically binds. Therefore, the abtide may be used as a substitute for the antibody in many of the reactions or assays that the antibody could be used in. For example, the abtide could be used in immunoassays known in the art, e.g., those designed to detect or measure the amount of the antigen. Of course, such immunoassays may have to be suitably modified. For example, many immunoassays make use of a step in which a second antibody, labeled with a radioactive moiety or an enzyme such as alkaline phosphatase, specifically binds to the first antibody. Such a second antibody would not be expected to specifically bind to the abtide. However, it would be well within the competence of one of ordinary skill in the art to fabricate another labelling moiety, perhaps a third antibody, that was able to specifically bind to the abtide, or to label the abtide with a detectable marker prior to use.

The immunoassays which can be used include but are not limited to competitive and non-competitive assay systems using techniques such as western blots, radioimmunoassays, ELISA (enzyme linked immunosorbent assays), "sandwich" immunoassays, dot immunoblot assays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, immunoaffinity chromatography, and flow dipstick assays to name but a few. For examples of exemplary procedures which can be used in immunoassays, see generally Kricka, 1985, Clinical and Biochemical Analysis 17:1–15; Armbruster, 1993, Clin. Chem. 39/2:181–195; Birnbaum et al., 1992, Anal. Biochem. 206:168–171; Miyai, 1985, Adv. Clin. Chem. 24:61–110; and references cited therein.

The samples to be assayed in the immunoassays can be any sample that may contain the antigen or ligand desired to be assayed. For example, these samples can be body fluids such as plasma, blood, serum, saliva, cerebrospinal fluid, synovial fluid, etc.

The detectable label to be used in the immunoassays can be any detectable label known in the art. Such labels include radioisotopes, fluorescent dyes, enzymes (for example horseradish peroxidase or alkaline phosphatase), chemiluminescent molecules, metal atoms, or phosphorescent dyes, colored particles, metal and dye colloids.

5.5.1.1. SANDWICH ELISA

In a particular embodiment, the abtides can be used in a sandwich enzyme immunoassay. One description of such an embodiment, presented by way of example and not limitation, follows: A molecule comprising an abtide is affixed to a solid substratum. The molecule comprising the abtide may be linked to a substance that will provide for greater attachment of the molecule to the substratum. The sample to be assayed is contacted with the molecule comprising the abtide that is bound to the substratum. The substances in the sample that are specific binding partners of the abtide (analyte) will bind to the abtide, and non-binding sample components are removed by washing. An enzyme-conjugated monoclonal antibody directed against the analyte is added. This enzyme-conjugated monoclonal antibody binds to the part of the analyte it is specific for and completes the sandwich. After removal of unbound enzyme-conjugated monoclonal antibody by washing, a substrate solution is added to the wells. A colored product is formed in proportion to the amount of analyte present in the sample. The reaction may be terminated by addition of stop solution and absorbance is measured spectrophotometrically. The following illustrates these steps in more detail.

(a) Polystyrene microtiter wells (Flow Laboratory) are coated overnight at room temperature with 100 $\mu$l of a solution of a molecule comprising an abtide at a concentration of 1 mg/ml in phosphate buffered saline (PBS).

(b) Coating solution is discarded and wells are blocked for 1–2 hours at room temperature with 300 $\mu$l of 1% bovine serum albumin (BSA) in phosphate-buffered saline (PBS) with 0.05% of "Tween™" 20 (polyoxyethylenes orbitan monolawrate).

(c) 150 $\mu$l of sample (suspected of containing an analyte the presence or amount of which it is desired to measure) diluted in 1% BSA-PBS is added per well. Wells are incubated 1 hour at room temperature.

(d) Wells are washed 4 times with PBS-"TWEEN™" buffer.

(e) 100 $\mu$l of horseradish peroxidase conjugated monoclonal antibody specific for the analyte in 1% BSA-PBS is added per well. The concentration of the monoclonal antibody can be from about 10 ng/ml to 10 mg/ml. Wells are incubated 1 hour at room temperature.

(f) Wells are washed 6 times with PBS -"TWEEN™" buffer.

(g) 100 $\mu$l of ABTS® Boehringer Mannheim (2,2'-Azino-di-[3-ethylbenzthiazdine sulfonate (6)] crystallized diammonium salt working solution is added per well. ABTS™ stock solution is prepared at 15 mg/ml in dH$_2$O. To make the working solution, 200 $\mu$l of this ABTS™ stock is diluted into 10 ml of citrate phosphate buffer (17 mm citric acid, 65 mm dibasic sodium phosphate) and 10 $\mu$l 30% H$_2$O$_2$.

(h) The absorbance of each well is measured at 405 nm in a microtiter plate reader (Dynatech MR600, Dynatech Corp., Alexandria, Va.).

5.5.2. PHARMACEUTICAL COMPOSITIONS

The invention provides methods of treatment by administration to a subject of an effective amount of a pharmaceutical (therapeutic or diagnostic) composition comprising an abtide. Such an abtide envisioned for therapeutic or diagnostic use is referred to hereinafter as a "Therapeutic" or "Therapeutic of the invention." Such therapeutics are abtides that specifically bind to a molecule in vivo, to exert a therapeutic or diagnostic effect. In a preferred aspect, the Therapeutic is substantially purified. The subject is preferably an animal, including but not limited to animals such as cows, pigs, horses, chickens, cats, dogs, etc., and is preferably a mammal, and most preferably human.

Formulations and methods of administration that can be employed are known in the art and can be selected from among those described hereinbelow.

Various delivery systems are known and can be used to administer a Therapeutic of the invention , e.g., encapsulation in liposomes, microparticles, microcapsules, recombinant cells containing the Therapeutic, receptor-mediated endocytosis (see, e.g., Wu and Wu, 1987, J. Biol. Chem. 262:4429–4432), etc. Methods of introduction include but are not limited to intradermal, intramuscular, intraperitoneal, intravenous, subcutaneous, intranasal, epidural, and oral routes as well as transdermal and subcutaneous time-release implants. The Therapeutics may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. In a specific embodiment, it may be desirable to utilize liposomes targeted via abtides to specific identifiable cell surface antigens.

In a specific embodiment, it may be desirable to administer the Therapeutics of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The present invention provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.5.3. IN VIVO DIAGNOSTIC AND THERAPEUTIC USES OF ABTIDES

Another area where abtides can be used in place of antibodies is in the imaging, detection, or treatment of disease. Current diagnostic and therapeutic methods make use of antibodies to target imaging agents or therapeutic substances, e.g. to tumors. Since abtides possess the same specificity of binding as antibodies, abtides can be used in place of antibodies in such diagnostic and therapeutic methods.

Abtides. may be linked to chelators such as those described in U.S. Pat. No. 4,741,900 or U.S. Pat. No. 5,326,856. The abtide-chelator complex may then be radiolabeled to provide an imaging agent for diagnosis or treatment of disease. The abtide may also be used in the methods that are disclosed in co-pending U.S. patent application Ser. No. 08/127,351, now U.S. Pat. No. 5,449,761, for creating a radiolabeled peptide for use in imaging or radiotherapy. This application contains a review of methods of using peptides in imaging agents.

In in vivo diagnostic applications, specific tissues or even specific cellular disorders may be imaged by administration of a sufficient amount of a labeled abtide of the instant invention.

A wide variety of metal ions suitable for in vivo tissue imaging have been tested and utilized clinically. For imaging with radioisotopes, the following characteristics are generally desirable: (a) low radiation dose to the patient; (b) high photon yield which permits a nuclear medicine procedure to be performed in a short time period; (c) ability to be produced in sufficient quantities; (d) acceptable cost; (e) simple preparation for administration; and (f) no requirement that the patient be sequestered subsequently. These characteristics generally translate into the following: (a) the radiation exposure to the most critical organ is less than 5 rad; (b) a single image can be obtained within several hours after infusion; (c) the radioisotope does not decay by emission of a particle; (d) the isotope can be readily detected; and (e) the half-life is less than four days (Lamb and Kramer, "Commercial Production of Radioisotopes for Nuclear Medicine", *In Radiotracers For Medical Applications*, Vol. 1, Rayudu (Ed.), CRC Press, Inc., Boca Raton, pp. 17–62). Preferably, the metal is technetium-99m.

By way of illustration, the targets that one may image include any solid neoplasm, certain organs such a lymph nodes, parathyroids, spleen and kidney, sites of inflammation or infection (e.g., macrophages at such sites), myocardial infarction or thromboses (neoantigenic determinants on fibrin or platelets), and the like evident to one of ordinary skill in the art. Furthermore, the neoplastic tissue may be present in bone, internal organs, connective tissue, or skin.

As is also apparent to one of ordinary skill in the art, one may use the present invention in in vivo therapeutics (e.g., using radiotherapeutic metal complexes), especially after having diagnosed a diseased condition via the in vivo diagnostic method described above, or in in vitro diagnostic application (e.g., using a radiometal or a fluorescent metal complex).

Accordingly, a method of obtaining an image of an internal region of a subject is contemplated in the instant invention which comprises administering to a subject an effective amount of an abtide composition containing a metal in which the metal is radioactive, and recording the scintigraphic image obtained from the decay of the radioactive metal. Likewise, a method is contemplated of enhancing an MR image of an internal region of a subject which comprises administering to a subject an effective amount of an abtide composition containing a metal in which the metal is paramagnetic, and recording the MR image of an internal region of the subject.

Other methods include a method of enhancing a sonographic image of an internal region of a subject comprising administering to a subject an effective amount of an abtide composition containing a metal and recording the sonographic image of an internal region of the subject. In this latter application, the metal is preferably any non-toxic heavy metal ion. A method of enhancing an X-ray image of an internal region of a subject is also provided which comprises administering to a subject an abtide composition containing a metal, and recording the X-ray image of an internal region of the subject. A radioactive, non-toxic heavy metal ion is preferred.

The use of abtides in place of antibodies in such methods has certain advantages. Because abtides are peptides rather than large proteins such as antibodies, the kinetics of their distribution in the body and clearance from the bloodstream differ from that of large proteins such as antibodies. For example, as demonstrated in Section 6.1.4, abtides can be used for in vivo imaging of disease states in about 2 to 5 hours. Current methods of tumor imaging using antibodies require approximately 24 to 48 hours.

Because abtides are peptides, they are cleared from the blood faster than antibodies. This means that there will be less background signal in the bloodstream when using abtides to image disease states than there is when using antibodies.

Peptides most likely will provoke less of an immune response in patients than do large proteins such as antibodies. This consideration is especially important when diagnosis or treatment is required to be done repeatedly or over a long period of time.

Abtides, because they are generally small proteins, can remain soluble in physiological fluids under conditions where antibodies cannot.

Abtides, again because they are generally peptides, can be produced synthetically or by recombinant methods and therefore may be less costly to produce than antibodies.

Abtides may be used individually. Alternatively, abtides may be used as compositions of abtides in which the peptide sequences of the abtides differ.

5.6. SYNTHESIS OF PEPTIDES
5.6.1. PROCEDURE FOR SOLID PHASE SYNTHESIS

Abtide or mimetope peptides may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394–1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3,-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenylmethoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the "FASTMOC™" protocol. The following side chain protected Fmoc amino acid derivatives are used: FmocArg(Pmc)OH; FmocAsn (Mbh) OH; FmocAsp ($^t$Bu) OH; FmocCys (Acm) OH; FmocGlu ($^t$Bu) OH; FmocGln (Mbh) OH; FmocHis (Tr) OH; FmocLys (Boc) OH; FmocSer ($^t$Bu) OH; FmocThr ($^t$Bu) OH; FmocTyr ($^t$Bu) OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using ca. 20% piperidine in NMP. At the end of each synthesis the amount of peptide present is assayed by ultraviolet spectroscopy. A sample of dry peptide resin (ca. 3–10 mg) is weighed, then 20% piperidine in DMA (10 mL) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol g$^{-1}$) can be calculated according to the equation:

$$\text{substitution} = \frac{A \times v}{7800 \times w} \times 1000$$

where A is the absorbance at 301 nm, v is the volume of 20% piperidine in DMA (in mL), 7800 is the extinction coefficient (in mol$^{-1}$dm$^3$cm$^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, CH$_2$Cl$_2$ and finally diethyl ether.

5.6.2. CLEAVAGE AND DEPROTECTION

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoracetic acid (TFA). A total volume of ca. 50 mL of these reagents are used per gram of peptide-resin. The following ratio is used: TFA:EtSMe:EDT:PhSme (10:0.5:0.5:0.5). The mixture is stirred for 3 h at room temperature under an atmosphere of $N_2$. The mixture is filtered and the resin washed with TFA (2×3 mL). The combined filtrate is evaporated in vacuo, and anhydrous diethyl ether added to the yellow/orange residue. The resulting white precipitate is isolated by filtration. See King et al., 1990, Int. J. Peptide Protein Res. 36:255–266 regarding various cleavage methods.

5.6.3. PURIFICATION OF THE PEPTIDES

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

5.6.4. CONJUGATION OF PEPTIDES TO OTHER MOLECULES

The abtides of the present invention may be linked to other molecules (e.g., a detectable label, a molecule facilitating adsorption to a solid substratum, or a toxin, according to various embodiments of the invention) by methods that are well known in the art. Such methods include the use of homobifunctional and heterobifunctional cross-linking molecules.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., 1984, Science 223:1304–1306.

Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. Some examples of heterobifunctional reagents containing reactive disulfide bonds include N-succinimidyl 3-(2-pyridyl-dithio)propionate (Carlsson et al., 1978, Biochem J. 173:723–737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio) propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

Additional information regarding how to make and use these as well as other polyfunctional reagents may be obtained from the following publications or others available in the art:

Carlsson et al., 1978, Biochem. J. 173:723–737.
Cumber et al., 1985, Methods in Enzymology 112:207–224.
Jue et al., 1978, Biochem 17:5399–5405.
Sun et al., 1974, Biochem. 13:2334–2340.
Blattler et al., 1985, Biochem. 24:1517–152.
Liu et al., 1979, Biochem. 18:690–697.
Youle and Neville, 1980, Proc. Natl. Acad. Sci. USA 77:5483–5486.
Lerner et al., 1981, Proc. Natl. Acad. Sci. USA 78:3403–3407.
Jung and Moroi, 1983, Biochem. Biophys. Acta 761:162.
Caulfield et al., 1984, Biochem. 81:7772–7776.
Staros, 1982, Biochem. 21:3950–3955.
Yoshitake et al., 1979, Eur. J. Biochem. 101:395–399.
Yoshitake et al., 1982, J. Biochem. 92:1413–1424.
Pilch and Czech, 1979, J. Biol. Chem. 254:3375–3381.
Novick et al., 1987, J. Biol. Chem. 262:8483–8487.
Lomant and Fairbanks, 1976, J. Mol. Biol. 104:243–261.
Hamada and Tsuruo, 1987, Anal. Biochem. 160:483–488.
Hashida et al., 1984, J. Applied Biochem. 6:56–63.

Additionally, methods of cross-linking are reviewed by Means and Feeney, 1990, Bioconjugate Chem. 1:2–12.

5.6.4.1. BIOTINYLATION OF PEPTIDES

Methods of biotinylating peptides are well known in the art. Any convenient method may be employed in the practice of the invention. For example, the following procedure was used:

(1) dissolve 10 mg of peptide in 100 µL of 0.1% acetic acid;
(2) add 900 µL of PBS;
(3) add 3.3 mg of biotin-LC-NHS (Pierce, Rockford, Ill.);
(4) incubate for 30 minutes at room temperature;
(5) purify over a Superose 12 column (Pharmacia, Piscataway, N.J.).

6. EXAMPLES

6.1. ABTIDES MIMICKING THE BINDING SPECIFICITY OF MONOCLONAL ANTIBODY 7E11-C5

6.1.1. IDENTIFICATION AND ISOLATION OF ABTIDES MIMICKING THE BINDING SPECIFICITY OF MONOCLONAL ANTIBODY 7E11-C5

7E11-C5 is a murine IgG1 monoclonal antibody specific for an antigen of a human prostate carcinoma, LNCaP. 7E11-C5 binds strongly to malignant prostatic epithelium but only weakly to normal prostatic epithelium. It does not bind to non-prostatic tumors or to most normal organs. See Horoszewicz et al., 1987, Anticancer Res. 7:927–936. 7E11-C5 is also described in U.S. Pat. No. 5,162,504 issued Nov. 10, 1992. Hybridomas producing monoclonal antibody 7E11-C5 were grown as ascites in mice and 7E11-C5 was purified from ascites fluid by Protein A affinity chromatography to over 90% purity as judged by sodium dodecylsulfate polyacrylamide gel electrophoresis.

In order to identify abtides mimicking binding specificity of monoclonal antibody 7E11-C5, monoclonal antibody 7E11-C5 was used as the target ligand in a first screening of the TSAR-9 library (see Kay et al., 1993, Gene 128:59–65 and PCT publication WO 94/18318, dated Aug. 18, 1994). The following screening procedure was used. First, 7E11-C5 was bound to a well of a microtiter plate. 7E11-C5 at a concentration of 11.2 mg/mL in phosphate buffered saline (PBS), pH 6.0, was diluted to 100 µg per mL in 0.1× PBS pH 7.2. One hundred microliters (100 µL) of this dilution was added to one well of a microtiter plate, and allowed to incubate for 1–6 hours at room temperature or overnight at 4° C. After incubation, the well was washed at least 4 times with a blocking buffer which consisted of either 1% bovine serum albumin (BSA) in PBS, 1% non-fat dry milk (NFDM) in PBS, or 0.1% "TWEEN™" in either 1% BSA in PBS or 1% NFDM in PBS. Two hundred microliters of the blocking buffer was then added to the well and allowed to incubate for at least an hour at room temperature.

Next, an aliquot of the TSAR-9 library was added to the well containing bound 7E11-C5. An aliquot of the library containing $10^{10}$ phage particles was added to the well and allowed to incubate for at least 1 hour at room temperature. This resulted in the binding to the plate of those phage containing binding domains that bind to 7E11-C5. After an hour, the well was washed extensively with either 1% bovine serum albumin (BSA) in PBS, 1% non-fat dry milk (NFDM) in PBS, or 0.1% "TWEEN™" in either 1% BSA in PBS or 1% NFDM in PBS.

After washing, phage bound to the 7E11-C5 antibody in the well were eluted by adding 100 μL of an acid solution of 0.2M glycine-HCl, pH 2.0. After incubation from 15 minutes to 1 hour, the acid solution containing eluted phage was transferred to a 1.5 mL microfuge tube, and an equal volume of 0.2M Tris-HCl, pH 7.5 added to neutralize the acid solution. In some cases, the neutralized phage solution was immediately added to a second well containing bound 7E11-C5 antibody, and the binding and elution procedure repeated.

If it was desired that the level of enrichment be monitored during the above steps, an irrelevant phage that does not bind 7E11-C5 but that expresses the β-galactosidase gene was added to the aliquot from the TSAR-9 library. This phage gives rise to blue plaques when plated in the presence of X-Gal and IPTG. Following a screening step, the eluted phage were plated in X-gal and IPTG. An aliquot of unscreened phage were plated as well. The ratio of white to blue plaques was measured for both phage samples. The increase in the proportion of white plaques (from the TSAR-9 phage that bind to 7E11-C5) to blue plaques (from the irrelevant phage) indicated the degree to which the screening process enriched the population of phage for those phage that bind 7E11-C5.

If it was desired that the specificity of binding be monitored during the above screening steps, screening was done against an irrelevant target (either BSA, mouse IgG, or plastic) in addition to being done against 7E11-C5. The enrichment of white plaques over blue plaques when panning was done against 7E11-C5 rather than an irrelevant target indicated the level of specificity of binding.

After screening, the phage were amplified by adding an aliquot of the eluted phage to a solution containing LB broth and competent DH5αF' E. coli cells (GIBCO BRL, Gaithersburg, Md.). Typically a 2–5 μL aliquot of the phage solution was added to 125 μL of LB broth containing a 1:50 dilution of DH5αF' E.Coli cells (about 1×10⁹ cells/ml). 3.3 mL of top agar was added to this solution, and the mixture was plated out onto a Petri dish containing agar. Often the phage were titered by making several serial 1:10 dilutions, and plating out the dilution as described above. After incubation overnight at 37° C., the plates were evaluated for growth of plaques, and counted if desired. The plates were eluted by adding 3–5 mL of 100 mM NaCl, 10 mM MgCl₂, 10 mM Tris-HCl, pH 7.5 (SM buffer) to each plate and incubating for 1–5 hours with gentle rocking. The solution was then removed from the plate, centrifuged, and either stored, amplified further, or analyzed.

In some cases, the phage were amplified in solution by adding 1–5 μL of the phage solution to 1–5 mL of LB broth containing a 1:50 or 1:100 dilution of competent DH5αF' E. coli cells (about 1×10⁹ cells/ml. After incubation for either 6 hours or overnight, the solution was centrifuged and the supernatant collected. In some cases, the phage particles were precipitated with polyethylene glycol (PEG) by adding a ⅕ volume of PEG to the clarified phage solution, and incubating for 1 hour on ice. After centrifugation, the phage were usually reconstituted with 100 μL of SM buffer.

Using the above procedures, nine different phage were isolated that expressed peptides containing binding domains that were capable of binding monoclonal antibody 7E11-C5. Molecules comprising these binding domains are thus mimetopes of the antigen recognized by the monoclonal antibody 7E11-C5. The binding domains of the peptides expressed by the nine phage were sequenced according to standard methods of DNA sequencing ("SEQUENASE™", U.S. Biochemical Corp., Cleveland, Ohio). The determination of those DNA sequences allowed the determination of the amino acid sequences of these mimetopes. These sequences are shown in Table 1. Examination of these amino acid sequences showed that they shared a common motif of MYxxLH (SEQ ID NO. 10).

TABLE 1

| | | | |
|---|---|---|---|
| SCVSHMLDTSRVYTAYANPG | MYSRLH | SPAVRPLTQSSA | (SEQ ID No.: 11) |
| SVQFKSISSRSMDDVVKDPGPKPA | MYNRLH | SKNPFTLS | (SEQ ID No.: 12) |
| YFDHTYSGPVVKNGGLVSPGVLS | MYNRLH | SDGGPSLAS | (SEQ ID No.: 13) |
| TVAT | MHDRLH | SAPGSGNLPGSYDIKPIFKAQSGALHST | (SEQ ID No.: 14) |
| IDMPQTAST | MYNMLH | RNEPGGRKLSPPANDMPPALLKR | (SEQ ID No.: 15) |
| RLGNHVWREGGG | MYQQLH | HNFP | (SEQ ID No.: 16) |
| RDSAVENPSVGGEIP | MYRYLH | QR | (SEQ ID No.: 17) |
| PVQKEYGFGMSGAS | MIRLIR | ETP | (SEQ ID No.: 18) |
| QKGGPGLLLYGGDS | MYITLH | EPG | (SEQ ID No.: 19) |
| | MYxxLH | | (SEQ ID No.: 10) |
| LYANPGMYSRLHSPA | | | (SEQ ID No.: 20) |

In order to use the mimetopes to identify abtides, peptides corresponding to the mimetope sequences were synthesized, and then dissolved in either water or PBS to give a final concentration of 5 μg/mL. Specifically, a peptide called 7E11-9.5, with the sequence LYANPGMYSRLHSPA (SEQ ID NO: 20) and a peptide with the sequence GMYSRLHSPA (SEQ ID NO: 21) were synthesized.

Figure 2:
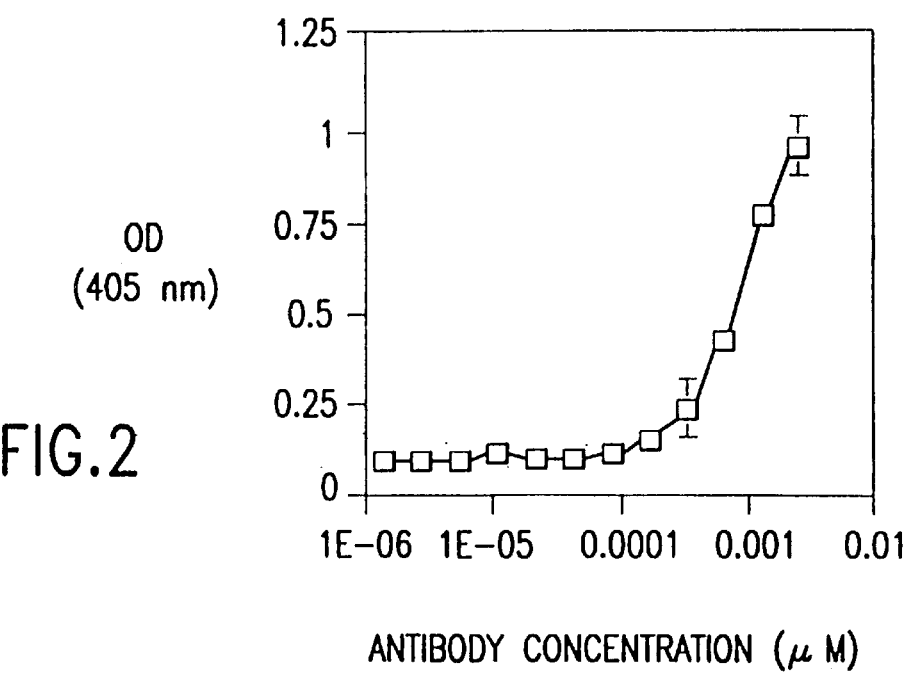
FIG. 2 shows the binding of biotinylated monoclonal antibody 7E11-C5 to immobilized mimetope peptide 7E11–9.5. See Section 6.1.2.2 for details.

First the mimetope peptide 7E11-9.5 was tested for its ability to bind to the monoclonal antibody 7E11-C5. Ninety-six well plates (Immunlon 4, Dynatech, Alexandria, Va.) were coated with 50 μL of a 5 μg/mL solution of the mimetope peptide 7E11-9.5 and incubated overnight at room temperature. Following incubation, the wells were washed 4 times with 1% BSA in PBS. Biotinylated monoclonal antibody 7E11-C5 was serially diluted with PBS beginning with a concentration of 29 μg/mL and various amounts of the monoclonal antibody were added to the wells that had been coated with the mimetope peptide. After incubating for 1 hour at room temperature, the wells were washed four times with 1% BSA in PBS and 2 times with PBS. Then, 100 μL of a 1:2000 dilution of Extravidin-Alkaline Phosphatase (4,250 units/mL) (Sigma, St. Louis, Mo.) in PBS was added to each well. After an hour, the plate was again washed 4 times with PBS and 100 μL of a 1 mg/mL solution of the enzyme substrate p-nitrophenyl phosphate was added to each well. Color was allowed to develop for 15 minutes to 1 hour and absorbance was read at 405 nm. FIG. 2 shows the results. It can be seen from FIG. 2 that monoclonal antibody 7E11-C5 binds to the synthesized mimetope 7E11-9.5 in a concentration dependent manner.

Next, the mimetope peptide was used to isolate abtides from a peptide library. Fifty to one hundred microliters of the solution of this peptide was used to coat the wells of a 96-well plate, the wells were blocked with 0.5% BSA in PBS, and the wells were used for screening. An aliquot of the TSAR-9 random phage library (containing approximately $3 \times 10^{10}$ phage particles) was used as in the initial screening, and 4 rounds of screening were performed. After the first two rounds, the phage were amplified. Two more rounds of screening were then performed. By this procedure, phage from the TSAR-9 library that expressed peptides capable of binding to the 7E11-9.5 mimetope peptide were identified and isolated. The peptides containing the binding domains of these phage are abtides and were discovered to mimic the binding specificities of monoclonal antibody 7E11-C5. These abtides are termed "7E11-C5 abtides."

Phage encoding the 7E11-C5 abtides were subjected to DNA sequencing of the nucleotide sequences encoding their binding peptides in order to obtain the DNA and amino acid sequences of the 7E11-C5 abtides. Table 2 shows the amino acid sequence of five of the 7E11-C5 abtides that had relatively high affinity for the mimetope.

TABLE 2

| Clone | Sequence |
|---|---|
| 14 | GIINANDPLPFWFMSPYTPGPAPIDINASRALVSNESG |
| 17 | DLSRNLDPGRFLLYNAYVPGFTPTFISLTAEHLSSPKG |
| 15 | CGRAYCLSGNYNIFGALFPGVSTPYADVGHDDAQSWRR |
| 13 | RCSPIWGISYPFGLLSSNPGVCHSSDAETNIRNDILTT |
| 16 | GHSNYCFVSTLGMPIVGFPSINARGLIHYGGSDPRLAA |

The amino acid sequence shown in Table 2 for clone 14 is SEQ ID NO: 1. The amino acid sequence shown in Table 2 for clone 17 is SEQ ID NO: 2. The amino acid sequence shown in Table 2 for clone 15 is SEQ ID NO: 3. The amino acid sequence shown in Table 2 for clone 13 is SEQ ID NO: 4. The amino acid sequence shown in Table 2 for clone 16 is SEQ ID NO: 5.

It was of interest to determine whether there might be some structural basis for the similarity in binding characteristics between the monoclonal antibody 7E11-C5 and the 7E11-C5 abtides. The amino acid sequences of the complementarity determining regions (CDRs) of the monoclonal antibody 7E11-C5 were determined by sequencing cDNA clones of the genes encoding the variable regions of the antibody. These CDRs are responsible for the specific binding of monoclonal antibody 7E11-C5 to its antigen. FIG. 3 presents a comparison of the amino acid sequences of the abtides of Table 2 and portions of the amino acid sequences of some of the CDRs of monoclonal antibody 7E11-C5. Surprisingly, it can be seen that there are similarities in the sequences of these abtides and the sequences of the CDRs of the monoclonal antibody.

6.1.2. CHARACTERIZATION OF 7E11-C5 ABTIDES

7E11-C5 abtides were tested for their ability to bind to the 7E11-C5 mimetopes that were used as target ligands in the second screening step above. The DNA sequences of the regions of the phage DNA encoding the abtides were determined. This allowed the determination of the amino acid sequences of the abtides. Based upon these determined amino acid sequences, synthetic peptides corresponding to these sequences were made. These synthetic peptides (7E11-C5 abtides) were 38 amino acids in length.

6.1.2.1. DOT BLOTS USING 7E11-C5 ABTIDES

In some cases, these abtides were used in a dot blot experiment. In those cases, 1 μL of a 1 mg/mL solution of the 38-residue abtides was spotted onto nitrocellulose (0.2 μm or 0.45 μm, Schleicher & Schuell, Keene, N.H.) strips or circles. After drying (about ½ hour), the nitrocellulose was blocked for 1 hour in a solution of 1% BSA in PBS. The nitrocellulose was then allowed to incubate in approximately 5 mL of a solution of 0.1 mg/mL of a biotinylated 7E11-9.5 mimetope peptide (biotin-LYANPGMYSRLHSPA) (SEQ ID NO: 20). This mimetope peptide was one of those described in Section 6.1.1 above that were synthesized based upon the nine peptides that were identified in the screening of Section 6.1.1 above. After an hour, the nitrocellulose was washed approximately 5 times with a solution of 1 BSA in PBS. A 1:2000 dilution of Extravidin-Alkaline Phosphatase (4,250 units/mL) (Sigma, St. Louis, Mo.) in PBS was then added and allowed to incubate for 1 hour, after which the nitrocellulose was again washed extensively. Finally, a solution of 5-bromo-4-chloro-3-indolyl phosphate (0.15 mg/mL) and nitro blue tetrazolium (0.3 mg/mL) (Sigma, St Louis, Mo.) (BCIP/NBT) was added as an enzyme substrate. Color was allowed to develop and the absorbance at 405 nm was read.

An example of such a dot blot assay is shown in FIG. 4. In FIG. 4, the 7E11-C5 abtides known as clone 14, clone 17, clone 15, clone 16, and clone 13 were tested for their ability to bind the biotinylated 7E11-9.5 mimetope peptide. Also tested, as a positive control, was the monoclonal antibody 7E11-C5. 7E11-C5 was spotted onto the region marked 351 in FIG. 4. Inspection of FIG. 4 shows that at least three of the abtides (clone 14, clone 17, and clone 15) bound the mimetope. This shows that these abtides are capable of mimicking the specific binding exhibited by the monoclonal antibody 7E11-C5.

6.1.2.2. 7E11-C5 ABTIDES IN PLACE OF ANTIBODIES IN IMMUNOASSAYS

The ability of abtides synthesized having the amino acid sequence encoded by the random inserts of the phage that bound the 7E11-9.5 mimetope was further evaluated by ELISA assay methods.

The 7E11-C5 abtides clone 14 and clone 17 (See Table 2) were each dissolved in 0.1× PBS to give a solution of 5 μg/mL. Fifty microliters of each of these solutions was used to coat the wells of a 96-well microtiter plate (Immulon 4, Dynatech, Alexandria, Va.) by overnight incubation at 4° C. Following this incubation, the abtide solutions were removed and the wells were blocked with 200 μL μl of a solution of 1% BSA in PBS. Mimetope peptides 7E11-9.5 (LYANPGMYSRLHSPA [SEQ IN NO: 20]) and GMYSRLHSPA (SEQ ID NO: 21) were biotinylated as described in Section 5.6.4.1 and dissolved in H₂O to give 1 mg/mL solutions. Serial 1:2 dilutions were made of these solutions and these dilutions were added to the wells of the microtiter plate containing the bound abtides. After incubation for 1 hour at room temperature, the wells were washed four times with 1% BSA in PBS. Then a 1:2000 dilution of Extravidin- Alkaline Phosphatase (4,250 units/mL) (Sigma, St. Louis, Mo.) in PBS was added to each well and incubated for 1 hour at room temperature. Following incubation, the wells were washed four times with 1% BSA in PBS and then twice in PBS. One hundred microliters of a 1 mg/mL solution of p-nitrophenyl phosphate in diethanol amine (DEA) buffer (both from Kirkegaard & Perry Laboratories, Gaithersburg, Md.) was then added and, after incubation for 15–30 minutes at room temperature, the absorbance of the solutions in the wells was read at 405 nm. The results are shown in FIG. 5.

FIG. 5 shows that, except for the non-linear effect at high concentrations of mimetope, there is a good correlation between the amount of mimetope added to the wells and the absorbance at 405 nm. The use of antibodies in assays such as enzyme-linked immunosorbent assays (ELISAs) to measure the concentration of a substance is well known in the art. The ability of antibodies to specifically bind their antigens is crucial to the success of such assays. Since abtides also specifically bind to antigens, it was of interest to determine if abtides can be used in place of antibodies in immunoassays such as ELISA-like assays to measure the concentration of a substance. The results of FIG. 5 show that the abtides of the present invention can be used in assays in much the same way that antibodies can be used in immunoassays such as ELISAs.

6.1.2.3. BIOTINYLATION OF ANTIBODIES

Methods of biotinylating antibodies are well known in the art. Any convenient method may be employed in the practice of the invention. For example, the following procedure was used:

(1) dissolve 10 mg of antibody in 1 mL of PBS;

(2) add 0.44 mg of biotin-LC-NHS (Pierce, Rockford, Ill.);

(3) incubate for 30 minutes at room temperature;

(4) purify over a Superose 12 column (Pharmacia, Piscataway, N.J.).

6.1.3. 7E11-C5 ABTIDES AND MONOCLONAL ANTIBODY 7E11-C5 RECOGNIZE AN LNCaP ANTIGEN

The monoclonal antibody 7E11-C5 recognizes a prostate specific mucin antigen of the human prostate cancer cell line LNCaP (Horoszewicz et al., 1987, Anticancer Res. 7:927–936). To determine if 7E11-C5 abtides recognize and bind the native antigen, the following experiment was done.

A sandwich assay using the LNCaP antigen was performed. The wells of a microtiter plate were coated with either monoclonal antibody 7E11-C5, the clone 14 7E11-C5 abtide, or, as a negative control, BSA. Coating and washing was as for the assay described in Section 6.1.2.2. One hundred microliters of a lysate of LNCaP cells was added to the wells. The LNCaP lysate was prepared as described in PCT publication WO 94/18318, dated Aug. 18, 1994. Following capture of the lysate on the plate, 100 μL of a 5μg/mL solution of biotinylated 7E11-C5 monoclonal antibody was added to each well. Following incubation and washing as in Section 6.1.2.2, a 1:2000 dilution of Extravidin-Alkaline Phosphatase (4,250 units/mL) (Sigma, St. Louis, Mo.) in PBS was added to each well and incubated for 1 hour at room temperature. Following incubation, the wells were washed four times with 1% BSA in PBS and then twice in PBS. One hundred microliters of a 1 mg/mL solution of p-nitrophenyl phosphate in diethanol amine (DEA) buffer (both from Kirkegaard & Perry Laboratories, Gaithersburg, Md.) was then added and, after incubation at room temperature for 15–30 minutes, the absorbance of the solutions in the wells was read at 405 nm.

The results are shown in FIG. 6. FIG. 6 shows that the 7E11-C5 abtide is capable of recognizing the native 7E11-C5 antigen in LNCaP lysates. This was a surprising discovery and would not have been predicted by those skilled in the art. It was generally felt that screening a library with a mimetope could yield a binder to that mimetope. Whether such a binder could also bind the native epitope that the mimetope mimics was unknown. The mimetope could have represented the epitope in a loose fashion, e.g. its primary sequence could be slightly modified; its secondary structure or factors influencing the presentation of the mimetope could be different from those presenting the native epitope. In such a case, the binder to the mimetope would not be specific for the native epitope. The foregoing is presented as possible explanation and not as a limitation of the present invention.

6.1.4. USE OF 7E11-C5 ABTIDES IN BIODISTRIBUTION STUDIES

The 7E11 abtides described in Section 6.1 and its subsections above were used in biodistribution studies to assess their ability to target human prostate carcinoma LNCaP xenograft tumors that had been transplanted into mice.

Male SCID mice (C.B-17/Icr Tac—SCID mice) were purchased from Fox Chase (Philadelphia, Pa.) or Taconic Farms (Germantown, N.Y.), were housed in sterilized cages with filter bonnets, and were given autoclaved laboratory rodent chow (Purina, St. Louis, Mo.), and filtered tap water ad libitum.

$1 \times 10^7$ cells of the human prostate tumor line LNCaP (Horoszewicz et al., 1987, Anticancer Res. 7:927–936) were injected subcutaneously (s.c.) into the left rear flank of the mice. The cells were growing in exponential phase before harvesting and had been resuspended in 0.2 mL of sterile saline. Tumors were grown in the mice for 2–3 months before abtides were injected into the mice.

For biodistribution studies, abtides were modified at their amino termini with the chelator diethylene-triamine-pentaacetic acid anhydride (DTPA-A) (Sigma, St. Louis, Mo.). Approximately 2 mg of each abtide was initially dissolved in an appropriate volume of 0.1% acetic acid and then 1 mL of 0.1M sodium bicarbonate, pH 8.0, was added. Two mg of DTPA-A was suspended in 100 μL of dimethylsulfoxide (DMSO), and 10 μL of the abtide solution added to this DTPA-A suspension. After 5 min incubation at room temperature, the suspension was filtered through a 0.2 μm "ACRODISC™" polyvinylidene difluoride (PVDF) sample filter "ACRODISC™", Gelman Sciences, Inc., Ann Arbor, Mich.), and purified using a Superose-12 FPLC column (Pharmacia, Piscataway, N.J.) with PBS as the running buffer. Modified peptides were stored frozen at –20° C. or –70° C.

Abtides modified with DTPA were labeled with $^{111}InCl_2$ as follows. 0.1 to 0.5 mCi of $^{111}InCl_2$ (Amersham, Chicago, Ill.) were first neutralized by adding an equal volume of 0.1M NaOAc, and then added to 100 to 200 μg of the DTPA-A-modified abtide. After incubation for one half hour, the labeled peptide was purified using a Superose-12 FPLC column (Pharmacia, Piscataway, N.J.) with PBS as the running buffer. Labeled fractions were collected in a fraction collector. Tubes containing the labeled peptide were pooled and used to prepare syringes for injection into mice.

In one experiment, abtide clone 14-DPTA-$^{111}$In (see Table 2) was injected intravenously (i.v.) into two groups of mice bearing measurable LNCaP xenografts. About 0.2 mL of a 10 μg/mL solution of the radioactively labeled abtide in sterile saline was used. The specific activity of the abtide was about 32 μCi/μg. Thus, the total injected dose of radioactivity was about $120-140 \times 10^6$ cpm.

The first group of mice was sacrificed 2 hours after injection of the abtide and tissues were dissected for analysis. The second group was sacrificed 4 hours after injection. Dissected tissues were weighed and the amount of $^{111}$In in them was determined by gamma counting. The cpm per gram of each tissue was calculated by dividing the cpm of $^{111}$In found in the tissue by the weight in grams of the tissue. The data are presented as the ratio of the cpm/g in each organ to the cpm/g in blood (organ to blood ratio). This gave the ratios that are shown in Table 3 and FIG. 7.

TABLE 3

BIODISTRIBUTION OF ABTIDE CLONE 14-DPTA-$^{111}$In IN LNCaP XENOGRAFT BEARING MICE

| Tissue[c] | Group 1[a] | | Group 2[b] | |
|---|---|---|---|---|
| | AVG | s.e.m. | AVG | s.e.m. |
| Blood | 1.00 | 0.00 | 1.00 | 0.00 |
| Lung | 0.81 | 0.04 | 1.06 | 0.26 |
| Spleen | 0.83 | 0.16 | 1.42 | 0.74 |
| Liver | 0.95 | 0.04 | 2.12 | 0.69 |
| Kidney-R | 55.85 | 10.22 | 171.73 | 77.97 |
| Kidney-L | 53.03 | 11.97 | 182.79 | 86.38 |
| Tumor | 1.85 | 0.80 | 3.91 | 2.85 |
| Muscle | 0.33 | 0.03 | 0.42 | 0.01 |
| Testes-R | 0.54 | 0.02 | 0.94 | 0.25 |
| Testes-L | 0.68 | 0.24 | 0.88 | 0.24 |

[a]Group 1: sacrificed at 2 hours; n = 2.
[b]Group 2: sacrificed at 4 hours; n =2.
[c]Value shown is the organ to blood ratio.

Table 3 and FIG. 7 show that, with the exception of kidney, the highest organ to blood ratio is found in the tumor, both at 2 hours and at 4 hours post-injection of abtide. This result shows that abtides with the binding specificity of antibodies, e.g. that are specific for tumor antigens, can be used to localize to those tumors.

No unusual localization was seen to any non-tumor tissue or organ except kidney. The ratio for kidney is extremely high due to the well known tendency of injected peptides to localize to the kidneys prior to being cleared from the body.

In another experiment, abtide clone 17-DPTA-$^{111}$In (see Table 2) was injected intravenously into four SCID mice bearing measurable LNCaP xenografts. Administration of xenografts was as above. About 0.2 mL of a 0.1 μg/mL solution of the radioactively labeled clone 17 abtide in sterile saline was injected. The specific activity of the abtide was about 2.4 μCi/ng. Thus, the total injected dose of radioactivity was about 100–110×10$^6$ cpm.

In this experiment, mice were sacrificed at either 2 or 5 hours post-injection with labeled abtide. Again, as above, the data are presented as organ to blood ratios. As shown in Table 4 and FIG. 8, abtide clone 17-DPTA-$^{111}$In localized to LNCaP xenograft tumors in mice.

TABLE 4

BIODISTRIBUTION OF ABTIDE CLONE 17-DPTA-$^{111}$In IN LNCaP XENOGRAFT BEARING MICE

| TISSUE[a] | GROUP 1 MOUSE # | | GROUP 2 MOUSE # | |
|---|---|---|---|---|
| | 1 | 6 | 2 | 3 |
| BLOOD | 1.00 | 1.00 | 1.00 | 1.00 |
| LUNG | 2.52 | 2.57 | 4.33 | 2.47 |
| SPLEEN | 5.82 | 3.00 | 5.53 | 3.70 |
| LIVER-S | 5.42 | 5.58 | 8.37 | 4.03 |
| KIDNEY-R | 235.63 | 234.88 | 321.09 | 106.74 |
| KIDNEY-L | 563.71 | 220.69 | 424.64 | 104.09 |
| TUMOR-S | 10.60 | 15.01 | 8.36 | 2.90 |
| MUSCLE | 0.93 | 2.96 | 1.16 | 3.04 |
| TESTES-R | 2.71 | 2.19 | 2.31 | 3.15 |
| TESTES-L | 1.64 | 1.14 | 5.36 | 3.41 |

[a]Value shown is the organ to blood ratio.

Table 4 and FIG. 8, like Table 3 and FIG. 7, show that the injected abtide localized to the tumor. This indicates that abtides can be useful in the localization of tumors.

In contrast to the results of the two experiments described above, in which radioactively labeled abtides were shown to localize to tumors, when the same experiments were done with a radioactively labeled control (non-abtide) peptide (the tripeptide GYK-DPTA), no specific localization to tumors was observed. This can be seen in FIG. 9, which shows the biodistribution results for experiments using the $^{111}$In-labeled control peptide.

The radiolabeled peptide conjugate GYK-DPTA-$^{111}$In was injectd intravenously into 5 SCID mice bearing measurable LNCaP xenografts. Mice were dissected 2 hours (n=2) and 5 hours (n=3) after injection of 1.5 μg of control peptide having a specific activity of 30 μCi/μg. The organ to blood ratios are presented in Table 5 and FIG. 9. As shown, the control peptide did not selectively localize to the tumor. While the tumor to blood ratio in one mouse was 3.26, the control peptide distributed equally well to other organs (e.g. lung 3.52, spleen 3.27, liver 21.70, etc.). These results show that there was non-specific uptake of the control peptide in these organs. While abtide clone 14-DPTA-$^{111}$In demonstrated a tumor to blood ratio of only 1.85 at 2 hours (which appears lower than that obtained with the control peptide), clone 14-DPTA-$^{111}$In demonstrated specific localization to the tumor as the organ to blood ratios in the other organs were much lower (e.g. lung 0.81, spleen 0.83, liver 0.95, etc.).

TABLE 5

BIODISTRIBUTION OF GYK-DPTA-$^{111}$In IN LNCaP XENOGRAFT BEARING MICE

| ORGAN/BLOOD | GROUP 1 MOUSE # | | GROUP 2 MOUSE # | | |
|---|---|---|---|---|---|
| | 1 | 2 | 3 | 4 | 5 |
| BLOOD | 1.00 | 1.00 | 1.00 | 1.00 | 1.00 |
| LUNG | 2.96 | 3.52 | 0.95 | 2.84 | 2.39 |
| SPLEEN | 1.74 | 3.27 | 0.97 | 2.21 | 4.04 |
| LIVER-S | 31.79 | 21.70 | 21.56 | 25.38 | 17.78 |
| KIDNEY-R | 563.87 | 406.27 | 273.82 | 509.53 | 269.30 |
| KIDNEY-L | 584.69 | 417.98 | 297.65 | 433.97 | 280.50 |
| TUMOR-S | 1.14 | 3.26 | 0.86 | 1.68 | 1.87 |
| MUSCLE | 1.04 | 1.02 | 0.29 | 4.34 | 2.51 |
| TESTES-R | 603.01 | 58.49 | 0.82 | 2.05 | 2.25 |
| TESTES-L | 44.65 | 2.08 | 0.93 | 2.11 | 2.32 |

6.2. ABTIDES BINDING TO A BREAST CANCER ANTIGEN

6.2.1. IDENTIFICATION AND ISOLATION OF ABTIDES BINDING TO POLYMORPHIC EPITHELIAL MUCIN (PEM)

The monoclonal antibody SM-3 that specifically binds the polymorphic epithelial mucin (PEM) tumor antigen found on human breast cancer cells has been shown to be specific for the epitope defined by the amino acid sequence VTSAP-DTRPAPGSTAPPAHGVTSAPDTR (SEQ ID NO: 9) (Bruchell et al., 1989, Int. J. Cancer 44:691–696). A peptide comprising this sequence was synthesized and used to isolate abtides from TSAR peptide libraries by methods analogous to those described above. In these experiments, the specific TSAR libraries used were R26, D38 and DC43.

See FIGS. 10–12 for description of these libraries. Phage bound to PEM were eluted by either standard acid elution methods, stringent acid elution methods where phage were incubated with the PEM peptide for only 10 minutes prior to washing and elution, or were eluted using excess PEM peptide. Phage from each library were isolated that express peptides capable of binding to PEM. The amino acid sequences of PEM binding phage are shown in Table 6.

TABLE 6

Sequences of PEM Binding Phage

Acid Eluted
R26 Library
A15     SFMDYFFHTPEPKPAGYPNAYTDPKHPA (SEQ ID NO: 26)
A54     SSSIFDYAPFSWGSAGLSNSSINVFERS (SEQ ID NO: 27)
A5      SASLWDALGGWTTSAVPSYPRPHQTPGR (SEQ ID NO: 28)
A39     SLGLPWIDVFGRSSAEPWPFGRTNLPRS (SEQ ID NO: 29)
A16     SVHGAFLDSFFPWAADGPHGRGRL-TSF (SEQ ID NO:30)
DC43 Library
MA-8    EEKQGGRWSTMMPRPWCHEGGCGFLYYDAMTKPKTPPIMRTAA (SEQ ID NO: 31)
MA-21   LPRPFDDASWKLRAVKESPDGCGFGSPLLFPPYSGLPTFSSCD (SEQ ID NO: 32)
V22      GSFESARGVTCIGNHSIGAHGCGPLRSYASFNRGSGRRH (SEQ ID NO: 33)
D38 Library
MA-32   DQIGSRPQTTSRSISGSWWENAKTLWQQDYAFSAPNAA (SEQ ID NO: 34)
V23      LSDAWGNFTTSYRDSAGFPSHAMTTSQGGKRNHASRFP (SEQ ID NO: 35)
V21      VQLDDTSPRASGQETSQSEYDARPLLSKFAIPRPWSR (SEQ ID NO: 36)
V1       IDSSKNRISGTGYLSFPHIRHANRRHMADDSNLAPGPS (SEQ ID NO: 37)
Acid Eluted: "Stringent"
DC43 Library
V44      WSIGTHTGPEGKFRIPCDRSGCGGTTLTHGGLNSSPTGQHERP (SEQ ID NO:38)
V39      DPCEDGYWLSSVGRAGASIRGCGAIRRSSRTLTAEYSTRASNH (SEQ ID NO: 39)
V10      GSKRSCWGTTISNYFRPVPEGCGSASSINPNTNTGRLPSLHRQ (SEQ ID NO: 40)
V7       SSASSGCLGRAEHLDLDSVWGCGSQADMSRRYSPWYGRPRTGV (SEQ ID NO: 41)
V4       NVMWSSSKAGIRDCSQVPPGGCGPVNRHRASPPLTPFRHGSIR (SEQ ID NO: 42)
D38 Library
V45      PLTSGSSSEYRNRDDCPVYKYATNCPRLNFSPSRYSPF (SEQ ID NO: 43)
V32      GDAYGGIFSRPRQGLADSYIHASYTGKHFFRGPRPPPTR (SEQ ID NO: 44)
V27      STCIGAEGEWKSFHNFLQCRDATSTSSSTLDPTALRFG (SEQ ID NO: 45)
V40      YSATLWDQFGSRQVELWSNRHASSALPFASRASVLGSR (SEQ ID NO: 46)
Peptide Eluted
R26 Library
P24      ILGWPFLTGLGDSTVHPRGRKGTDPS (SEQ ID NO: 47)
P49      SIPSFSMWLNQLGSAALPSKGNSQDRSD (SEQ ID NO: 48)
P26      SRDDIFTGGPLVLFRGSKTSNHDVHSMR (SEQ ID NO: 49)
P6       RAELVNWYEWFHVTAEAETPVINSHNMT (SEQ ID NO: 50)
DC43 Library
MP-1     GAPVWRGNPRWRGPGGFKWPGCGNGPMCNTFTPARGGSRNNGP (SEQ ID NO: 51)
MP-2     GSASSCFPNFTARGVTVGFFGCGSPAHPAAPRVLNPATDFPAP (SEQ ID NO: 52)
MP-22    VFRRTARSSRPIGATVFPWYGCGNSNDETLPHHDSPPSFFLGA )SEQ ID NO: 53)
MA-13    NTCWTDLFWHGLPGGDLPRDGCGLPSELTTHSRERRDASEN (SEQ ID NO: 54)
D38 Library
MP-20    IDWNWLERGQHNRGYLHSFPDAKSQPTRGPRVAPNGND (SEQ ID NO: 55)
MP-30    GRGSDMREHWPWSMPLILDQHANDPSPRAQSHYYSHPF (SEQ ID NO: 56)

6.2.2. SATURATION MUTAGENESIS OF MP-1 AND IDENTIFICATION OF ADDITIONAL PEM BINDING ABTIDES

A saturation mutagenesis library based on one of the PEM abtides, MP-1, was constructed. Nucleotide sequences encoding the MP-1 abtide were synthesized using a doping scheme similar to that described in Section 5.3 whereby each nucleotide was contaminated with 9% of each of the other 3 nucleotides (e.g. G=73% G, 9% A, 9% T, 9% C). The resulting mutagenic oligonucleotides were used to construct a library by TSAR library methods described above (see FIG. 13).

The resulting library was screened to identify phage expressing abtides capable of binding to PEM. The binding of isolated phage to PEM was confirmed by an ELISA assay. Phage that were shown to bind to PEM as well as phage that did not bind to PEM were sequenced to determine the amino acid sequences of the expressed abtides. Table 7 shows the amino acid sequences of these positive and negative binding phage.

TABLE 7

Sequence Comparison: MP-1 Binding Motif

Positive Binding Sequences

| | | |
|---|---|---|
| MP1 | GAPVWRGNPRWRGPGGFKWPGCGNGPMCNTFTPARGGSRNNGP | (SEQ ID NO: 51) |
| E4 | VSTGWSGTPRWCAPGGKQGSGCGNGPRWTTLTPDLGGTRKYGP | (SEQ ID NO: 57) |
| E7 | GAPLWCEKLSGTGSGGFKWPGCGSGPTYNTFTPARVGSDNKWP | (SEQ ID NO: 58) |
| E16 | GPPVWSAKSRWTGTGVLNWPGCGKVPSCSTYTPSRDRSRKSDP | (SEQ ID NO: 59) |
| E21 | GSALLTSKGCVRGPGGLMRPGCGNDRLGKSSTYAHGGWIKTGP | (SEQ ID NO: 60) |
| E33 | GSPVWSGDNRWRGSSPLKRPGCGNGAKCNTLKDNRKDSRKTKH | (SEQ ID NO: 61) |
| E44 | GPLLPGEAAVHGARGLMRSGCGNGPTWNRLTAACRDSRNKGP | (SEQ ID NO: 62) |
| E65 | GSPVWMGSTRWTGHGWFRSQGCGNVPRTNSCAPAGKDSQNKGP | (SEQ ID NO: 63) |
| E73 | GAPVWRGNRWCSDNGELERPGCGYGPRFNILPPGRGNSRKPSP | (SEQ ID NO: 64) |
| E84 | GSSGWKVKHRCGGPGTLQRPGCGNLPLGHTFPPTRGGSHMEGA | (SEQ ID NO: 65) |
| E85 | GPRSWMGQPRGSDAGSCKWAGCGDAPMWRASTPGHGGPPNRGS | (SEQ ID NO: 66) |
| E88 | EALVCRGKPPWSGPAGLLWQGCGTGPVSRTFTSAQGRSRNKTS | (SEQ ID NO: 67) |
| E90 | GAPVVGDILWCSGARGAKWPGCGKGPTNKTFSHSRGGTQKSGL | (SEQ ID NO: 68) |
| E22 | GAPVSRCKPACGGFWGVNWPGCGNASMCKTFTNGHGVSSDNGH | (SEQ ID NO: 69) |
| E29 | GAHGYKNGSTCTGLGGWRCRGCGKGAMCNNPSPAGGAYHNQGP | (SEQ ID NO: 70) |
| E62 | GPQGSEHQCCSGHWGLKFPGCGNGPICNNFTALRGASRKNGP | (SEQ ID NO: 71) |
| E64 | GEPVWCRHSGGRVQGGLDWLGCGDGPLRYTVTPARGGPSKHGP | (SEQ ID NO: 72) |
| E66 | GLSLVRGDSWGSGAGGWKRHGCGHGPMYNPQTPARGGSCTRNT | (SEQ ID NO: 73) |
| E67 | VSRAWSGKPRLMGSHGLNCPGCGKGHSGIMFIPDPAGSANTPP | (SEQ ID NO: 74) |
| E68 | CAPMWSGKPPWCVGGGVKFRGCGNRPDCNIITPRLVESRDKAL | (SEQ ID NO: 75) |
| E70 | ADPVCSRKPDGGGLRGLRWPGCGKGPILYNVTAARGGSRNNGP | (SEQ ID NO: 76) |

TABLE 7-continued

Sequence Comparison: MP-1 Binding Motif

Negative Binding Sequences

| MPI | GAPVWRGNPRWRGPGGFKWPGCGNGPMCNTFTPARGGSRNNGP | (SEQ ID NO: 51) |
|---|---|---|
| E3 | GTRVPPGFALRGGRDGLSWAGCGKAPISKTYTSARGRSRKKGS | (SEQ ID NO: 77) |
| E15 | RSAVSEGKPREIVPGGCMWPGCGNGRKSNTLTHGPEQFQEIEP | (SEQ ID NO: 78) |
| E24 | SSGVGNGKPRSWAPDALNGGCGNIQFANTITPDRGGSCNQTL | (SEQ ID NO: 79) |
| E27 | GSSVCGGQPSGRGFGGLPGPGCGNGPTSNTLTSARGGFPNKGL | (SEQ ID NO: 80) |
| E37 | GAPLWQGDPADEVLGGSMIPGCGIGALSQTFTPTPGGSRKNVT | (SEQ ID NO: 81) |
| E43 | AGRELRQDEGEGGAGADVARLREGPICSTFTPARGGSCPSGL | (SEQ ID NO: 82) |
| E49 | QARVSMAISCRSGPSDLMHQGCGYGPRCNPDTTDSGGSHTNTP | (SEQ ID NO: 83) |
| E60 | GDPECRGKPRGRWTGSLACTGCGNGPNSKICTRARGVSRNKGP | (SEQ ID NO: 84) |
| E72 | STPGCSGYSGSGDPRCLTCTACGNGHTRKTLTPAHGRSTHKEP | (SEQ ID NO: 85) |
| E34 | GQPECRITSGCCGTDGNKWLGCGKVDMCNTLNPAVGCHGTNGS | (SEQ ID NO: 86) |
| E83 | REPVVGGKPWCRGPGGLRWRGCGKSQFDKIITLSRDNRRDKRP | (SEQ ID NO: 23) |

When the sequences shown in Table 7 are compared (see particularly the amino acid residues marked in boldface type), it is possible to determine the influence of particular amino acid residues at specific positions in the sequence on a peptide's ability to bind to PEM. Abtides that bind to PEM can be characterized by the formula:

$R_1R_2R_3R_4R_5R_6R_7R_8R_9R_{10}R_{11}R_{12}R_{13}R_{14}R_{15}R_{16}R_{17}R_{18}R_{19}R_{20}R_{21}R_{22}R_{23}$ $R_{24}R_{25}R_{26}R_{27}R_{28}R_{29}R_{30}R_{31}R_{32}R_{33}R_{34}R_{35}R_{36}R_{37}R_{38}R_{39}R_{40}R_{41}R_{42}R_{43}$ (SEQ ID NO: 24)

where:
$R_1$=G, C, E, or V, preferably G;
$R_2$=A, S, P, or L, preferably A;
$R_3$=P, T, H, or L, preferably P;
$R_4$=L, M, Q, G, A, or S;
$R_5$=W or Y, preferably W;
$R_6$=S, C, K or T, preferably S;
$R_7$=E, S, C, D, V, or R;
$R_8$=N, H, K, S, or E;
$R_9$=L, H, R, N, Q, T, or G;
$R_{10}$=W, P, R, T, or D, preferably W;
$R_{11}$=W, C, V, L, or G, preferably W;
$R_{12}$=S, T, M, or H, preferably S or T;
$R_{13}$=G;
$R_{14}$=S, A, G, N, Q, or H, preferably S;
$R_{15}$=W, H, G, A, or R;
$R_{16}$=G, T, E, P, V, or W, preferably G;
$R_{17}$=V, F, W, K, or A;
$R_{18}$=K, Q, D, E, R, or L, preferably K;
$R_{19}$=R, F, or S, preferably R;
$R_{20}$=P, S, I or H, preferably P;
$R_{21}$=G;
$R_{22}$=C;
$R_{23}$=G;
$R_{24}$=D, S, T, N, or H;
$R_{25}$=G, D, L, or R;
$R_{26}$=P or S, preferably P;
$R_{27}$=M, S, D, I, L, or R;
$R_{28}$=G, W, C, L, F, Y, or T, preferably G or W;
$R_{29}$=S, N, V, F, H, or R;
$R_{30}$=N, A, S, M, or R, preferably N;
$R_{31}$=F, Q, P, or V, preferably F;
$R_{32}$=S. V, I, K, A, or S;
$R_{33}$=P, A, N, or Y, preferably P;
$R_{34}$=G, N, or L;
$R_{35}$=K, R, C, Q or L, preferably K or R;
$R_{36}$=V, K, R, or A;
$R_{37}$=G, D, A, or E, preferably G;
$R_{38}$=S, T, P, Y or W; preferably S;
$R_{39}$=R, I, L, P, A or S;
$R_{40}$=N, K, or M, preferably N or K;
$R_{41}$=S, R, T, E, Q, P, Y or H;
$R_{42}$=G, A, S, D, N, P, Y, or K, preferably G;
$R_{43}$=P, H or A.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A peptide in which the amino acid sequence of said peptide consists of the sequence selected from the group consisting of:

GIINANDPLPFWFMSPYTPGPAPIDI-NASRALVSNESG (SEQ ID NO: 1),

CGRAYCLSGNYNIFGALFPGVSTPYAD-VGHDDAQSWRR (SEQ ID NO: 3),

DLSRNLDFGRFLLYNAYVPGFTPTFISL-TAEHLSSPKG (SEQ ID NO: 2),

RCSPIWGISYPFGLLSSNPGVCHSSDA-ETNIRNDILTT (SEQ ID NO: 4), and

GHSNYCFVSTLGMPIVGFPSINARGLI-HYGGSDPRLAA (SEQ ID NO: 5).

2. A composition comprising the peptide of claim 1; and a carrier.

* * * * *